US011110070B2

(12) United States Patent
Brachman et al.

(10) Patent No.: US 11,110,070 B2
(45) Date of Patent: Sep. 7, 2021

(54) PHARMACOLOGICAL PROPHYLACTICS AGAINST STRESS-INDUCED AFFECTIVE DISORDERS AND THEIR ASSOCIATED SYMPTOMS

(71) Applicant: The Trustees of Columbia University in the City of New York, New York, NY (US)

(72) Inventors: Rebecca Anne Brachman, Westfield, NJ (US); Christine Ann Denny, New York, NY (US); René Hen, Tenafly, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/776,880

(22) PCT Filed: Nov. 17, 2016

(86) PCT No.: PCT/US2016/062562
§ 371 (c)(1),
(2) Date: May 17, 2018

(87) PCT Pub. No.: WO2017/087691
PCT Pub. Date: May 26, 2017

(65) Prior Publication Data
US 2018/0325844 A1 Nov. 15, 2018

Related U.S. Application Data

(60) Provisional application No. 62/256,506, filed on Nov. 17, 2015.

(51) Int. Cl.
| | | |
|---|---|---|
| *A61K 31/135* | (2006.01) | |
| *A61P 25/22* | (2006.01) | |
| *A61P 25/24* | (2006.01) | |
| *A61K 9/00* | (2006.01) | |
| *A61K 31/138* | (2006.01) | |
| *A61K 31/401* | (2006.01) | |
| *A61K 31/42* | (2006.01) | |
| *A61K 31/4245* | (2006.01) | |
| *A61K 31/428* | (2006.01) | |
| *A61K 31/4525* | (2006.01) | |
| *A61K 31/453* | (2006.01) | |
| *A61K 31/513* | (2006.01) | |
| *A61K 31/517* | (2006.01) | |
| *A61K 31/53* | (2006.01) | |
| *A61K 33/00* | (2006.01) | |
| *A61K 31/198* | (2006.01) | |
| *A61K 45/06* | (2006.01) | |
| *A61K 31/445* | (2006.01) | |

(52) U.S. Cl.
CPC .......... *A61K 31/138* (2013.01); *A61K 9/0019* (2013.01); *A61K 9/0043* (2013.01); *A61K 9/0053* (2013.01); *A61K 31/135* (2013.01); *A61K 31/198* (2013.01); *A61K 31/401* (2013.01); *A61K 31/42* (2013.01); *A61K 31/428* (2013.01); *A61K 31/4245* (2013.01); *A61K 31/445* (2013.01); *A61K 31/453* (2013.01); *A61K 31/4525* (2013.01); *A61K 31/513* (2013.01); *A61K 31/517* (2013.01); *A61K 31/53* (2013.01); *A61K 33/00* (2013.01); *A61K 45/06* (2013.01); *A61P 25/22* (2018.01); *A61P 25/24* (2018.01); *A61K 2300/00* (2013.01)

(58) Field of Classification Search
CPC .. A61K 31/135; A61K 31/138; A61K 31/198; A61K 31/401; A61K 31/42; A61K 31/4245; A61K 31/428; A61K 31/445; A61K 31/4525; A61K 31/453; A61K 31/513; A61K 31/517; A61K 31/53; A61K 33/00; A61K 45/06; A61K 9/0019; A61K 9/0043; A61K 9/0053; A61P 25/22; A61P 25/25
See application file for complete search history.

(56) References Cited

U.S. PATENT DOCUMENTS

| | | |
|---|---|---|
| 3,254,124 A | 5/1966 | Stevens |
| 8,785,500 B2 | 7/2014 | Charney et al. |
| 2009/0105222 A1 | 4/2009 | Kranzler et al. |
| 2013/0236573 A1 | 9/2013 | Singh et al. |
| 2014/0057988 A1* | 2/2014 | Weg ..................... A61K 31/135 514/647 |

FOREIGN PATENT DOCUMENTS

| | | |
|---|---|---|
| WO | 2003020275 | 3/2003 |
| WO | 2008118785 | 10/2008 |
| WO | 2013056229 | 4/2013 |
| WO | WO 2013/056229 A1 | 4/2013 |
| WO | 2013149102 | 10/2013 |
| WO | 2014020155 | 2/2014 |
| WO | WO 2014/045023 A1 | 3/2014 |
| WO | 2014171826 | 10/2014 |
| WO | WO 2014/169272 A1 | 10/2014 |
| WO | 2015037248 | 3/2015 |

OTHER PUBLICATIONS

Brachman et al, Ketamine as a prophylactic against stress-induced depressive-like behavior, Biol Psychiatry. 2016, 79 (9): 776-786.
Murrough et al, Antidepressant Efficacy of Ketamine in Treatment-Resistant Major Depression: A two-site randomized controlled trial, Am. J. Psychiatry, 2013, vol. 170, Issue 10, pp. 1134-1142.
(Continued)

Primary Examiner — Kara R McMillian
(74) Attorney, Agent, or Firm — Leason Ellis LLP

(57) ABSTRACT

Methods for prophylactically treating a stress-induced affective disorder or stress-induced psychopathology in a subject are provided. Also provided are methods for inducing and/or enhancing stress resilience in a subject. In certain embodiments, an effective amount, of an antagonist of the glutamate N-methyl-D-aspartate (NMDA) receptor, such as ketamine, or a pharmaceutically acceptable salt or derivative thereof, is administered to a subject prior to a stressor.

9 Claims, 21 Drawing Sheets

(56) References Cited

OTHER PUBLICATIONS

E.D. Ballard et al., Improvement in suicidal ideation after ketamine infusion: Relationship to reductions in depression and anxiety, J. Psychiatry Research vol. 58 pp. 161-166 Nov. 2014.
Zarate et al, Ketamine for depression: evidence, challenges and promise, World Psychiatry. 2015;14(3):348-50.
Rasmussen et al, Serial infusions of low-dose ketamine for major depression, J Psychopharmacol. 2013; 27(5):444-50.
Reardon, Rave drug holds promise for treating depression fast, Nature, 517, 130-131 (2015).
ClinicalTrials.gov, Rapid Antidepressant Effects of Ketamine in Major Depression, National Institute of Mental Health (NIMH), Identifier: NCT00088699 [retrieved from https://clinicaltrials.gov/ct2/show/NCT00088699; First Posted: Aug. 2, 2004; Results First Posted: Oct. 12, 2018] [retrieved on Dec. 6, 2018].
Rachel Yarmolinsky, Could a Dose of Ketamine Prevent Psychiatric Disorders Such As PTSD?, Columbia University Department of Psychiatry, Jul. 2, 2015 [retrieved from https://www.columbiapsychiatry.org/news/could-dose-ketamine-prevent-psychiatric-disorders-such-ptsd].
Brent Miles as told to Troy Farah, I Used Ketamine to Treat My Depression, Vice, Jan. 15, 2015 [retrieved from https://www.vice.com/en_us/article/4w7eyd/i-used-ketamine-to-treat-my-depression-122].
Matt McMillen, Ketamine: The Future of Depression Treatment? WedMD.com, Depression Health Center, Sep. 23, 2014 [retrieved from https://www.webmd.com/depression/news/20140923/ketamine-depression#1].
Brachman et al., A single injection of ketamine confers robust, long-term protection against stress-induced depressive-like behaviors, Society for Neuroscience conference, Presentation Abstract on Nov. 17, 2014.
World Health Organization. List of Essential Medicines. Adults: 19th Edition. Apr. 2015.
International Search Report and Written Opinion dated Feb. 3, 2017 corresponding to International Patent Application No. PCT/US16/62562, 16 pages.
Womble, AL, "Effects of Ketamine on Major Depressive Disorder in a Patient with Posttraumatic Stress Disorder," AANA Journal, Apr. 2013, vol. 81, No. 2, pp. 118-119.
Domino, EF, "Taming the Ketamine Tiger," Anesthesiology, 2010, vol. 113, pp. 678-686.
Donahue RJ, Muschamp JW, Russo SJ, Nestler EJ, Carlezon WA Jr (2014): Effects of striatal deltaFosB overexpression and ketamine on social defeat stress-induced anhedonia in mice. Biol Psychiatry 76:550-558.
Denny CA, Kheirbek MA, Alba EL, Tanaka KF, Brachman RA, Laughman KB, et al. (2014): Hippocampal memory traces are differentially modulated by experience, time, and adult neurogenesis. Neuron 83: 189-201.
David DJ, Samuels BA, Rainer Q,Wang JW, Marsteller D, Mendez I, et al. (2009): Neurogenesis-dependent and -independent effects of fluoxetine in an animal model of anxiety/depression. Neuron 62:479-493.
Hammack SE, Cooper MA, Lezak KR (2012): Overlapping neurobiology of learned helplessness and conditioned defeat: Implications for PTSD and mood disorders. Neuropharmacology 62:565-575.
Maier SF, Seligman MEP (1976): Learned helplessness: Theory and evidence. J Exp Psychol 105:3-46.
Muller JM, Morelli E, Ansorge M, Gingrich JA (2011): Serotonin transporter deficient mice are vulnerable to escape deficits following inescapable shocks. Genes Brain Behav 10:166-175.

Dulawa SC, Holick KA, Gundersen B, Hen R (2004): Effects of chronic fluoxetine in animal models of anxiety and depression. Neuropsychopharmacology 29:1321-1330.
Autry AE, Adachi M, Nosyreva E, Na ES, Los MF, Cheng PF, et al. (2011): NMDA receptor blockade at rest triggers rapid behavioural antidepressant responses. Nature 475:91-95.
Caddy C, Giaroli G, White TP, Shergill SS, Tracy DK (2014): Ketamine as the prototype glutamatergic antidepressant: Pharmacodynamic actions, and a systematic review and meta-analysis of efficacy. Ther Adv Psychopharmacol 4:75-99.
Mendez-David I, David DJ, Darcet F, Wu MV, Kerdine-Romer S, Gardier AM et al. (2014): Rapid anxiolytic effects of a 5-HT(4) receptor agonist are mediated by a neurogenesis-independent mechanism. Neuropsychopharmacology 39 (6):1366-1378.
Rainer Q, Xia L, Guilloux JP, Gabriel C, Mocaer E, Hen R, et al. (2011): Beneficial behavioural and neurogenic effects of agomelatine in a model of depression/anxiety. Int J Neuropsychopharmacol 15(3):321-335.
Muller JM, Morelli E, Ansorge M, Gingrich JA. (2011): Serotonin transporter deficient mice are vulnerable to escape deficits following inescapable shocks. Gene Brain Behav 10(2):166-175.
Richardson-Jones JW, Craige CP, Guiard BP, Stephen A, Metzger KL, Kung HF, et al. (2010): 5-HT1A Autoreceptor Levels Determine Vulnerability to Stress and Response to Antidepressants. Neuron 65(1): 40-52.
Amat J, Dolzani SD, Tilden S, Christianson JP, Kubala KH, Bartholomay K, et al. (2016): Previous ketamine produces an enduring blockage of neurochemical and behavioral effects of uncontrollable stress. J Neurosci 36:153-161.
Brachman, RA, McGowan JC, Perusini JN, Lim SC, Plam TH, Faye C, et al. (2016): Ketamine as a prophylactic against stress-induced depressive-like behavior. Biol Psychiatry 79:776-786.
Denny CA, Burghardt NS, Schachter DM, Hen R, Drew MR (2012): 4- to 6-week-old adult-born hippocampal neurons influence novelty-evoked exploration and contextual fear conditioning. Hippocampus 22:1188-1201.
Drew MR, Denny CA, Hen R (2010): Arrest of adult hippocampal neurogenesis in mice impairs single- but not multiple-trial contextual fear conditioning. Behav Neurosci 124:446-454.
Feder A, Parides MK, Murrough JW, Perez AM, Morgan JE, Sazena S. et al. (2014): Efficacy of intravenous ketamine for treatment of chronic posttraumatic stress disorder. JAMA Psychiatry 71:681-688.
McGhee LL, Maani CV, Garza TH, DeSocio PA, Gaylord KM, Black IH (2009): The effect of propranolol on posttraumatic stress disorder in burned service members. J Burn Care Res 30:92-97.
Schiller D, Monfils MH, Raio CM, Johnson DC, LeDoux JE, Phelps EA (2010): Preventing the return of fear in humans using reconsolidation update mechanisms. Nature 463:49-53.
Trouch S, Sasaki JM, Tu T, Reijmers LG (2013): Fear extinction causes target-specific remodeling of perisomatic inhibitory synapses. Neuron 80:1054-1065.
Nikiforuk Agnieszka et al: "Ketamine prevents stress-induced cognitive inflexibility in rats", Psychoneuroendocrinology, 2013, vol. 40, pp. 119-122.
Parise Eric M et al: "Repeated Ketamine Exposure Induces an Enduring Resilient Phenotype in Adolescent and Adult Rats", Biological Psychiatry, 2013, vol. 74, No. 10, pp. 750-759.
Feder Adriana et al: "Efficacy of Intravenous Ketamine for Treatment of Chronic Posttraumatic Stress Disorder A Randomized Clinical Trial", JAMA Psychi, 2014, vol. 71, No. 6, pp. 681-688.
Supplementary European Search Report in corresponding European Application EP 16867149.3, dated Nov. 6, 2019.

\* cited by examiner

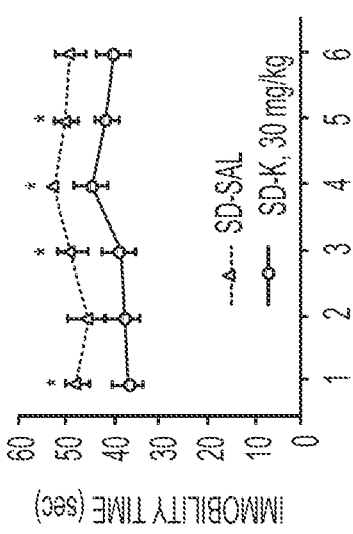
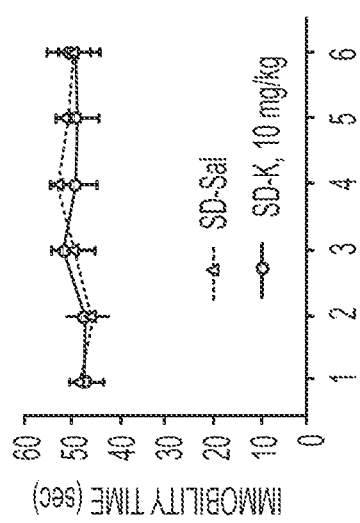
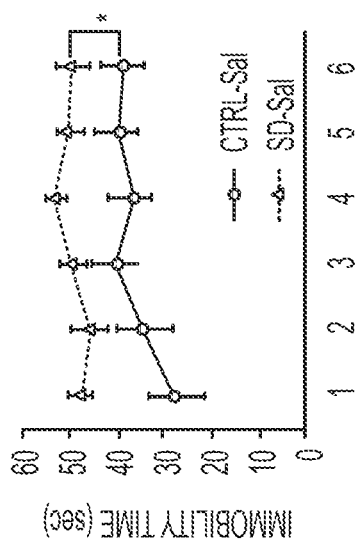
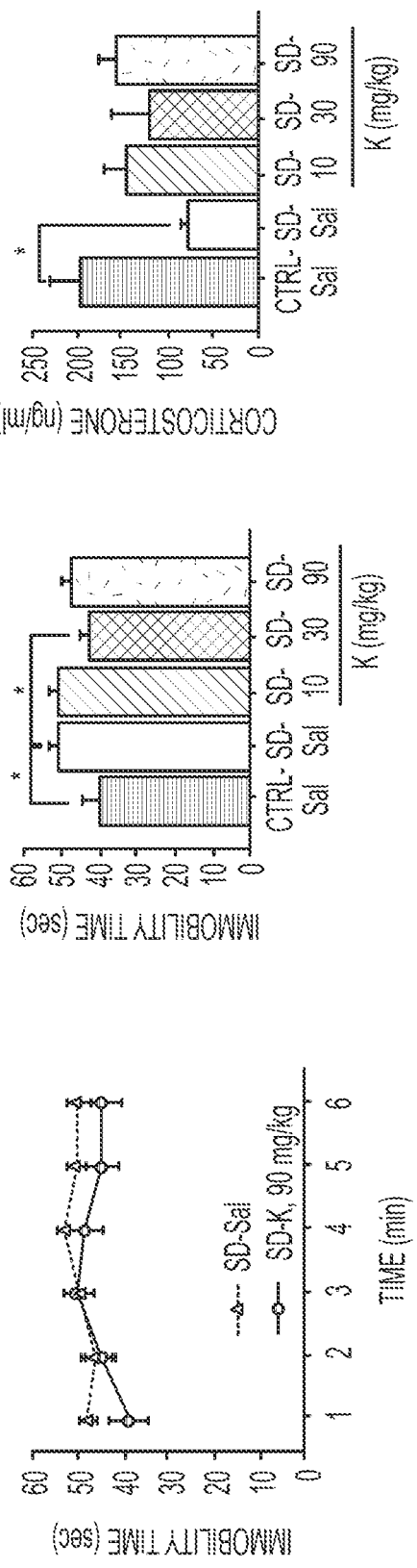
FIG. 2A  FIG. 2B  FIG. 2C  FIG. 2D  FIG. 2E  FIG. 2F

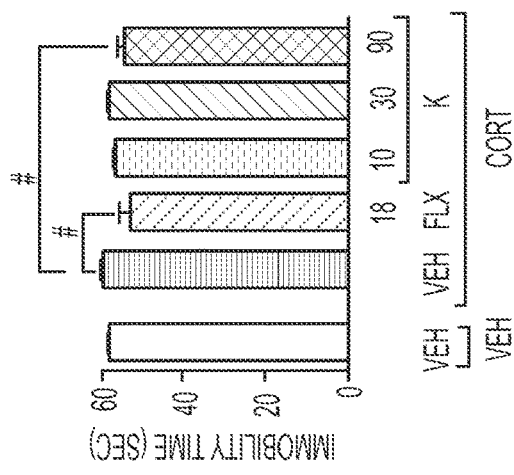
FIG. 4A
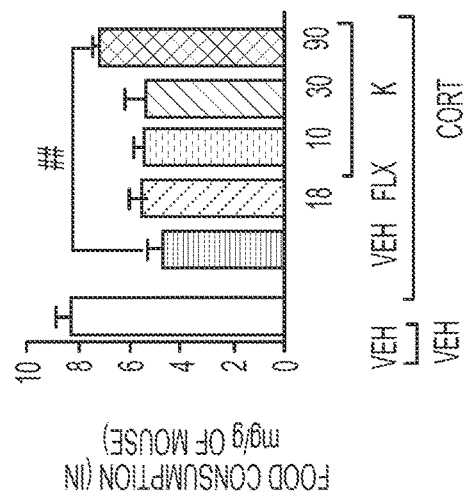
FIG. 4B
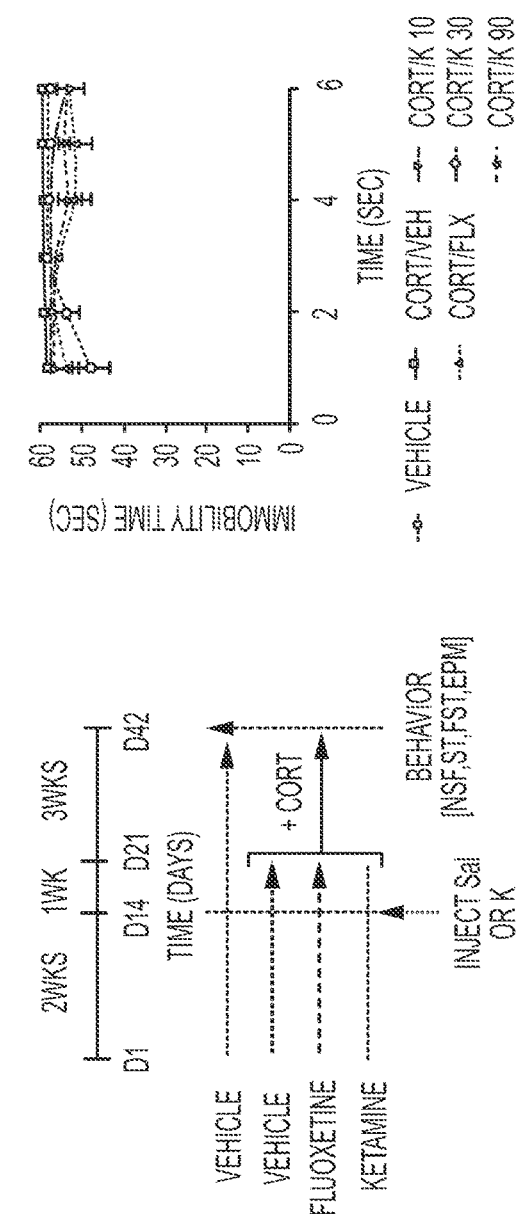
FIG. 4C
FIG. 4D
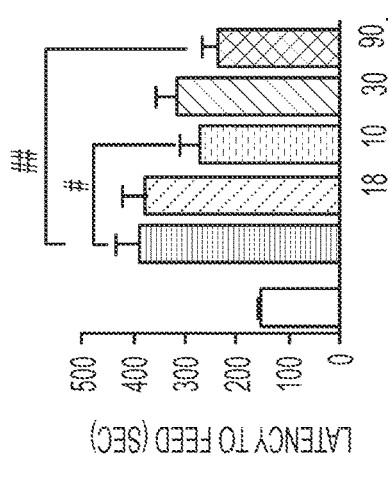
FIG. 4E
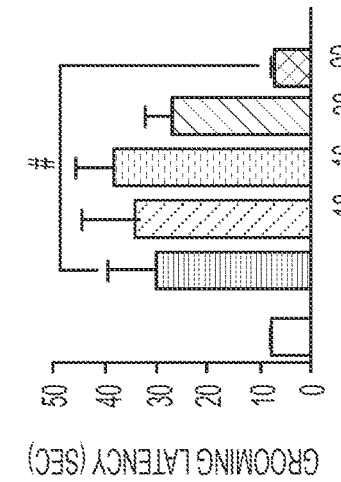
FIG. 4F

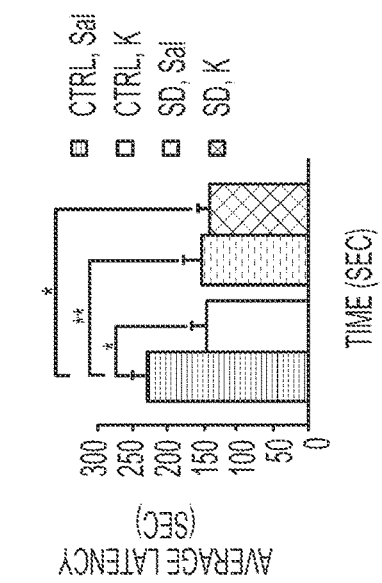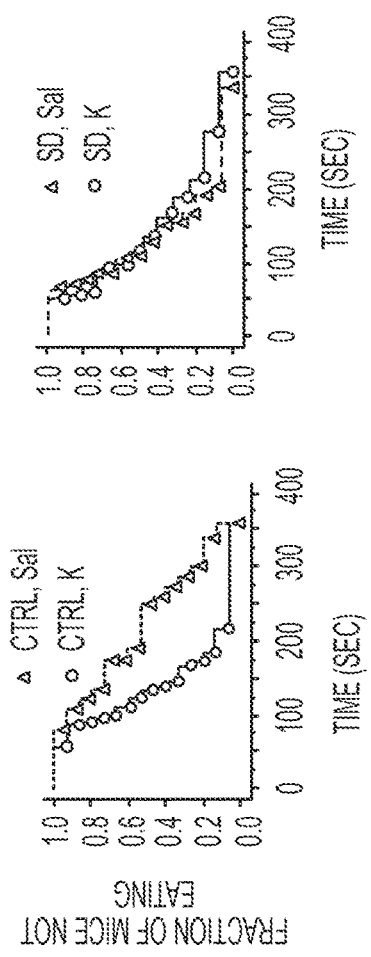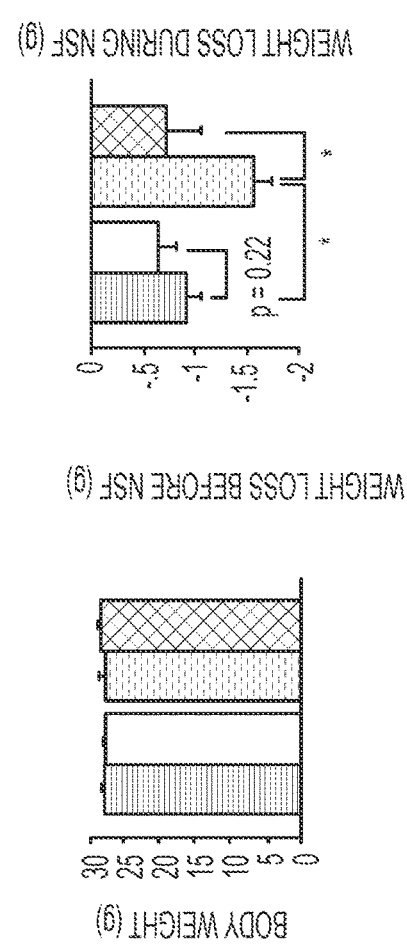
FIG. 6A FIG. 6B
FIG. 6C FIG. 6D FIG. 6E FIG. 6F

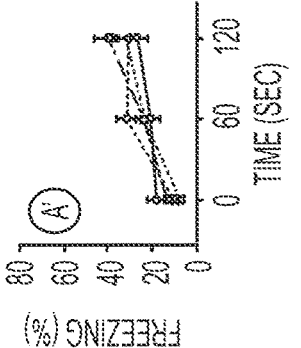
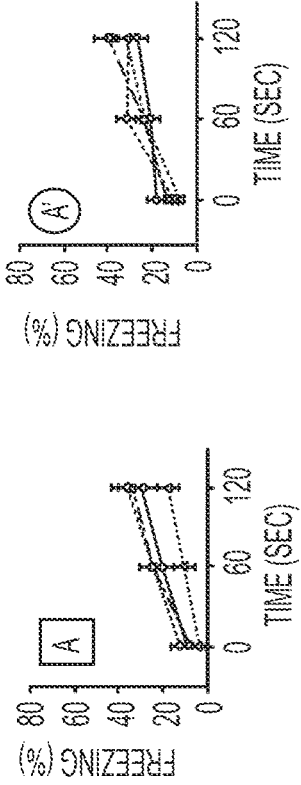
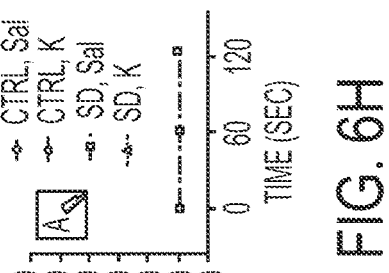
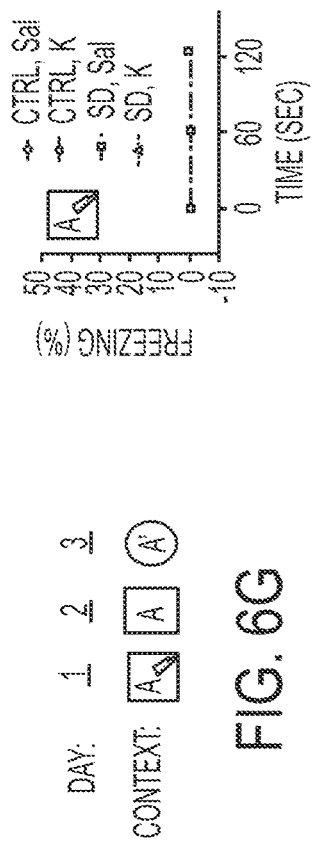
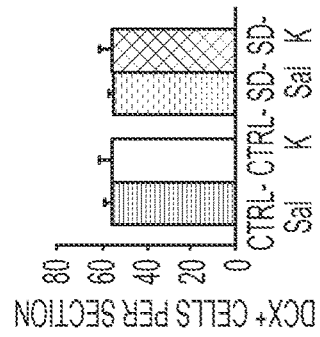
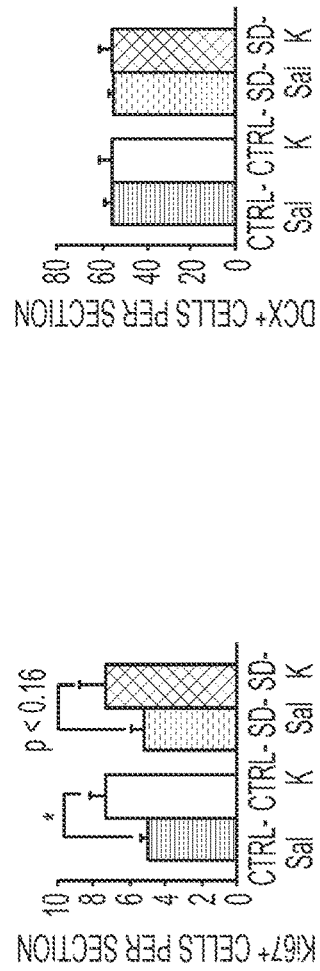

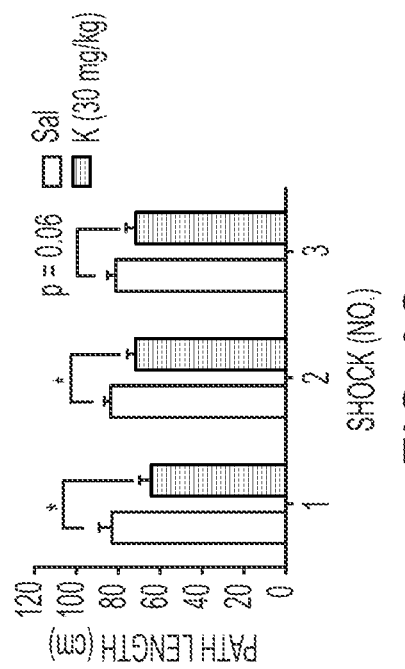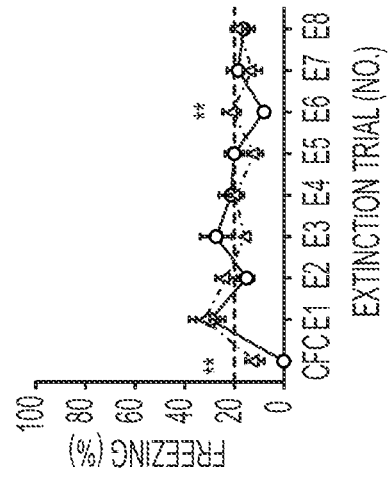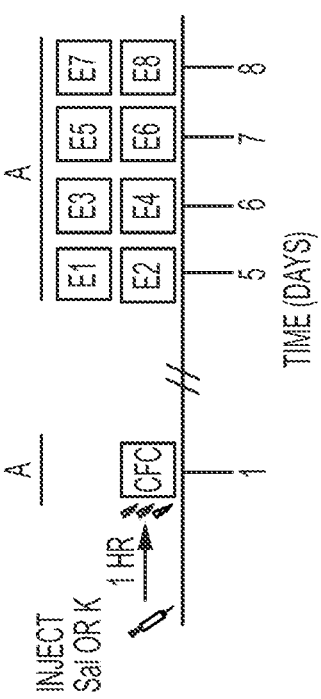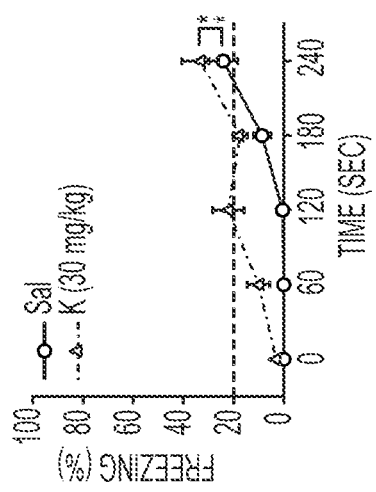
FIG. 9A
FIG. 9B
FIG. 9C
FIG. 9D

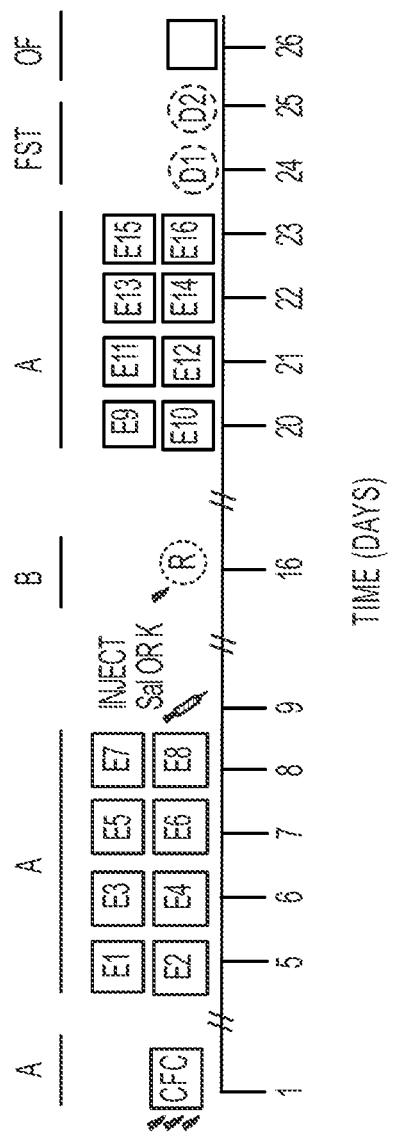
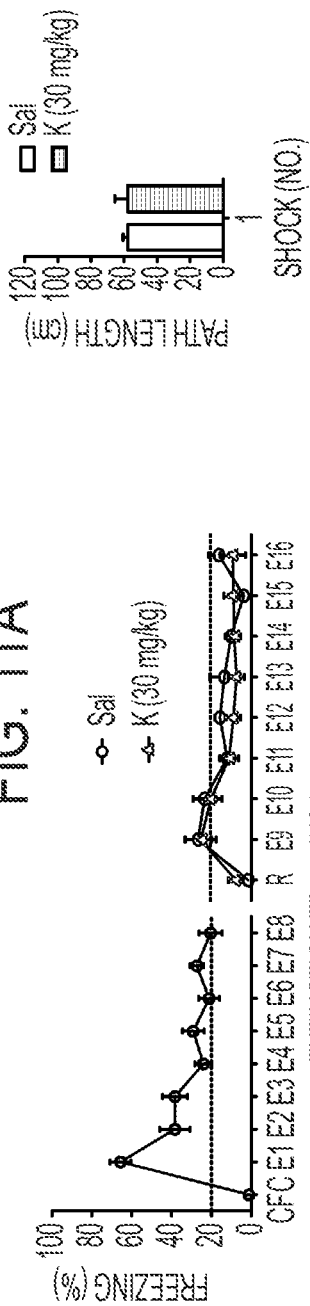
FIG. 11A
FIG. 11B
FIG. 11C

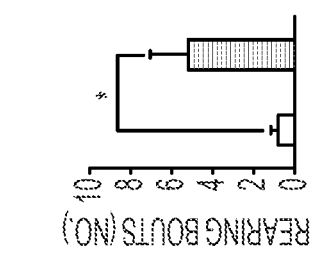
FIG. 11F
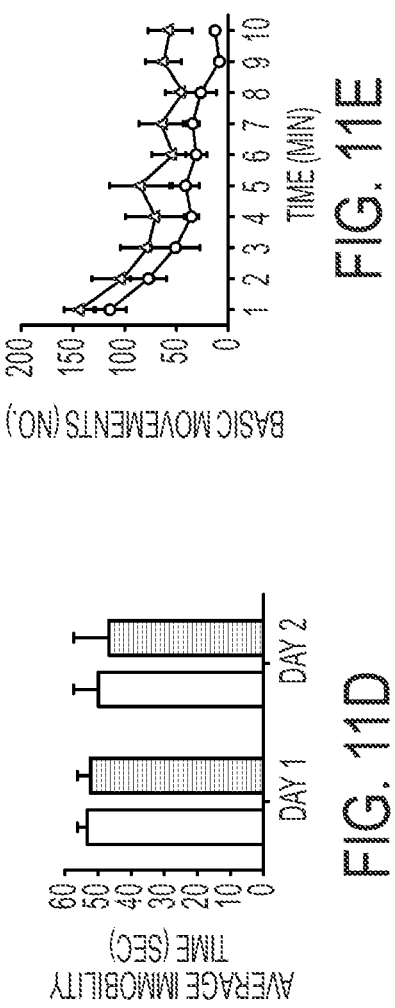
FIG. 11E
FIG. 11D
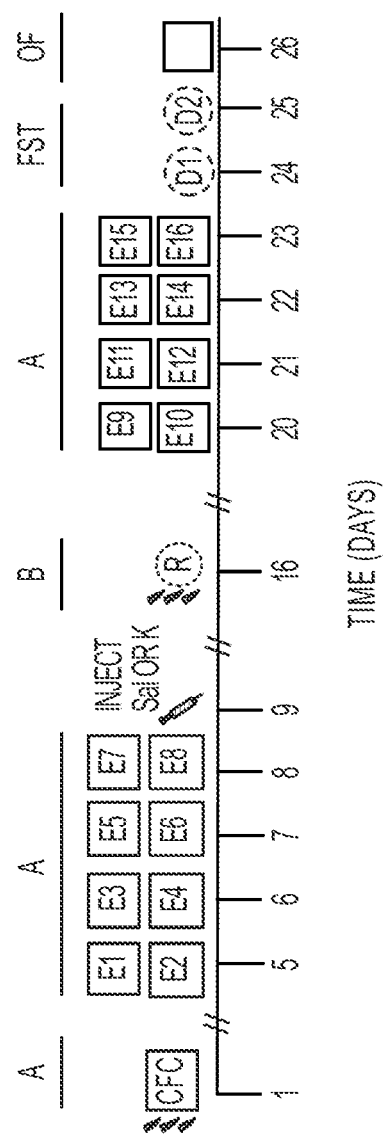
FIG. 11G

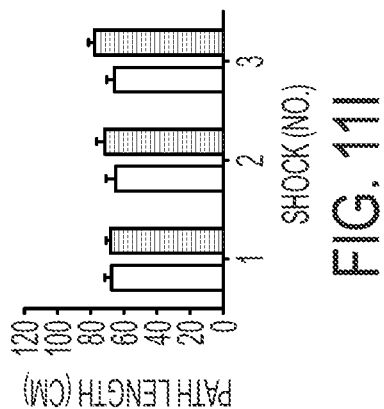
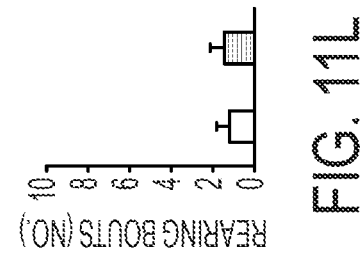
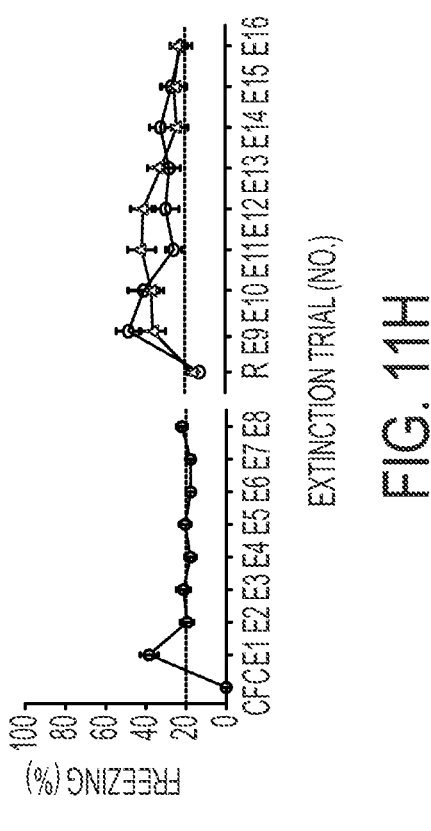
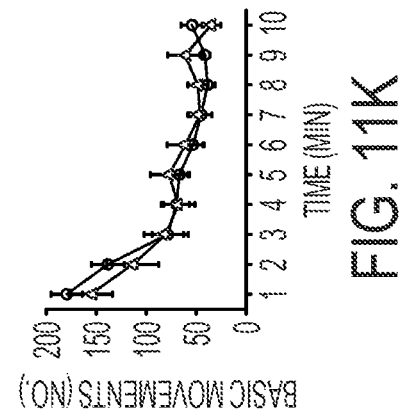
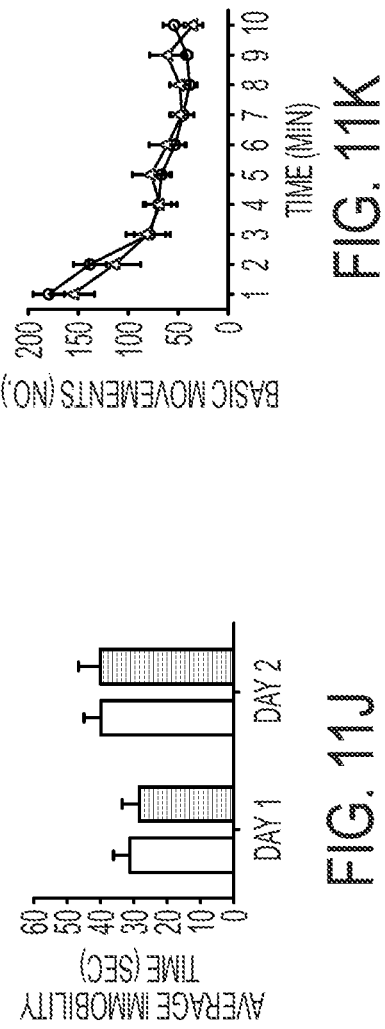

PHARMACOLOGICAL PROPHYLACTICS AGAINST STRESS-INDUCED AFFECTIVE DISORDERS AND THEIR ASSOCIATED SYMPTOMS

CROSS-REFERENCE TO RELATED PATENT APPLICATIONS

This is a U.S. National Phase Application under 35 U.S.C. § 371 of International Patent Application No. PCT/US2016/062562, filed Nov. 17, 2016, and claims priority to U.S. Provisional Application No. 62/256,506, filed Nov. 17, 2015, which is incorporated by reference in its entirety. The International Application was published on May 26, 2017 as International Publication No. WO 2017/087691 A1.

STATEMENT OF GOVERNMENT SUPPORT

This invention was made with government support under HD007430, MH068542, AG043688, MH015174, and OD017908 awarded by the National Institutes of Health. The government has certain rights in the invention.

FIELD OF THE INVENTION

The present invention relates to ketamine compositions and their use in methods of treatment or prevention of stress-induced affective disorders such as post-traumatic stress disorder (PTSD). In certain aspects, a ketamine composition can be administered prior to a stressor.

BACKGROUND OF THE INVENTION

Stress commonly precipitates psychiatric illness, particularly in vulnerable populations. For example, one in five soldiers returns from combat with posttraumatic stress disorder or combat-associated major depressive disorder (MDD) (1). Perhaps more surprising is that many soldiers do not develop psychopathology. While there has been extensive research on factors promoting susceptibility to psychiatric illnesses, few studies have examined what makes individuals resistant or stress resilient. Until recently, the sparse research on stress resilience has been predicated on the assumption that it is a passive property—more or less the absence of the risk factors that make individuals susceptible to stress-induced pathology (2). Recent work in animal models suggests that stress resilience is mediated through active processes and often distinct, parallel mechanisms to those of susceptibility (3-5). The idea that increasing stress resilience could protect against the development of psychiatric disorders is appealing, but treatments to increase resilience are still in their infancy.

Current interventions are all behavioral, with psychotherapy and exercise being the best available tools to increase resilience (6-8). Rodent studies further support a role for exercise and enriched environment in stress resilience (9-11).

Traditionally, affective disorders have been treated from a symptom-suppression approach. Existing drugs aim to mitigate the impact of these chronic diseases, but do not cure or prevent the disease itself. There are no known cures. Antidepressants are typically used to treat existing depressive symptoms, but chronic antidepressant treatment may also protect against subsequent depressive episodes (17-21). This is known as "tertiary prevention" or "tertiary prophylaxis," Tertiary preventions suppress symptoms and mitigate the impact of a chronic disease, but do not treat the underlying disease. Maintenance treatment in MDD patients is often referred to as prophylaxis against the development of additional depressive episodes (22), but this should not be confused with "primary prevention" or "primary prophylaxis," which aims to prevent the disease before it ever occurs. No antidepressants have yet been shown to be primary prophylactics. Whether these tertiary prophylactic antidepressants, which can decrease the incidence of symptomatic episodes in disordered individuals, are also able to work as primary prophylaxis and prevent de novo psychiatric disorders remains to be tested. Importantly, classical antidepressant efficacy is neither sufficient for, nor necessarily predictive of, primary prophylactic efficacy.

Post-traumatic stress disorder (PTSD) is an illness characterized by persistent, vivid re-experiencing of a traumatic event, hyperarousal, and avoidance of stimuli associated with the trauma (Charney et al., 1993). The National Center for PTSD reports that 7-8% of the United States population will experience PTSD at some point in their lives, and about 8 million adults suffer from the disorder each year (National Center for PTSD, 2015). PTSD is often comorbid with other prevalent psychiatric illnesses such as major depressive disorder (MDD) (28%) and substance use (73%) (Brady et al., 2000).

Currently, clinicians rely on several methods to reduce the symptomology of PTSD including pharmacology, psychotherapy, or a combination of both methods. A first-line approach to the pharmacological treatment of PTSD involves the use of selective serotonin reuptake inhibitors (SSRIs) (Pradhan et al., 2016). However. Stein and colleagues found that only 59% of individuals receiving SSRIs for PTSD responded to treatment after 14 weeks of treatment (Stein et al., 2006). Other pharmacotherapies include benzodiazepines and antiadrenergic agents, but these drugs are largely ineffective (Henry et al., 2007). These studies suggest that there is a critical need for improvements in drug therapy for PTSD. Alternatively, psychiatrists use cognitive behavioral therapy (CBT), which involves fear extinction through safe exposure to trauma-related cues (Golub et al., 2009). Other methods of psychotherapy include group therapy (Lubin et al., 1998), eye movement desensitization and reprocessing (Shapiro and Solomon, 2010), mindfulness-based cognitive training techniques (Hofmann et al., 2010), and physical activity (Rosenbaum et al., 2015). However, given the lack of empirical evidence and clinical utility of psychotherapy for trauma victims, consistent therapies have not been established (National Center for PTSD, 2016). As a result, there are currently disparate standpoints on the benefits of pharmacotherapy or psychotherapy for PTSD treatment, as many studies utilize incongruent techniques, making meta-analytic conclusions weak or flawed (Klein, 2000).

In light of the paucity of treatments for PTSD, researchers are pursuing potential strategies to prevent the onset of the PTSD and other psychiatric illnesses (Bernardini et al., 2016; Horn et al., 2016; Skeffington et al., 2016; Wald et al., 2016). Part of this work stems from an interest in methods to enhance stress resilience to prevent the onset of mental illness (Horn et al., 2016). A focus on preventative approaches can alleviate years of psychological and financial burden in victims of PTSD and their loved ones.

Ketamine is an antagonist of the glutamate N-methyl-D-aspartate (NMDA) receptor and an activator of AMPA receptors. Ketamine has emerged as a rapid acting, antidepressant for treatment-resistant MDD patients. It produces antidepressant effects as rapidly as 2 h following a single injection in patients with MDD (Zarate et at, 2006) and has sustained effects for approximately 1-2 weeks following the infusion (Berman et al., 2000). In contrast to previously mentioned SSRIs, ketamine has the benefit of being administered as a single dose (Zarate et al., 2006; Murrough et al., 2013). In addition to its antidepressant properties, ketamine has been found to be efficacious in the treatment of chronic PTSD (Feder et al., 2014), Feder and colleagues found that intravenous infusion of ketamine hydrochloride was associated with significant and rapid reduction in PTSD symptom severity when compared with midazolam (Feder et al., 2014). An initial study showed that the prevalence of PTSD was decreased in military patients that received ketamine during an operation for burns when compared with patients not receiving ketamine (McGhee et al., 2008). However, a follow-up study by the same authors failed to replicate their initial findings (McGhee et al., 2014). These studies bring into question how the dosing and timing of ketamine alters its efficacy as a treatment for PTSD. When ketamine should be administered in order to maximize its therapeutic effects remains unknown. Furthermore, whether any drugs are able to protect against PTSD has yet to be studied.

There is an unmet need for effective prophylactic therapies to prevent the onset of stress-induced affective disorders.

SUMMARY OF THE INVENTION in certain embodiments, the present invention relates to a method for preventing or delaying a stress-induced affective disorder or stress-induced psychopathology in a subject, comprising administering an effective amount of a pharmaceutic composition comprising ketamine, a ketamine analog, or a pharmaceutically acceptable salt, derivative, or metabolite thereof, to a subject prior to a stressor.

In additional embodiments, the invention relates to a method for inducing and/or enhancing stress resilience in a subject, comprising administering an effective amount of a pharmaceutic composition comprising ketamine, a ketamine analog, or a pharmaceutically acceptable salt, derivative, or metabolite thereof, to a subject prior to a stressor.

In further embodiments, the invention relates to a method for preventing or delaying a stress-induced affective disorder in a subject, or for inducing and/or enhancing stress resilience in a subject, the method comprising: administering an effective amount of a pharmaceutic composition comprising, an antagonist of the glutamate N-methyl-D-aspartate (NMDA) receptor to a subject prior to a stressor.

In certain embodiments, the antagonist of the NMDA receptor comprises ketamine, a ketamine analog, or a pharmaceutically acceptable salt, derivative, or metabolite thereof.

In further embodiments, the invention relates to a method for presenting or delaying a stress-induced affective disorder in a subject, or for inducing and/or enhancing stress resilience in a subject, the method comprising: administering an effective amount of a pharmaceutic composition comprising an α-amino-3-hydroxy-5-methyl-4-isoxazolepropionic acid (AMPA) receptor agonist, to a subject prior to a stressor.

In certain embodiments, the AMPA receptor agonist is selected from the group consisting of glutamate, AMPA, 5-fluorowillardiine, domoic acid, quisqualic acid, and (2R, 6R)-hydroxynorketamine, CX546, or a pharmaceutically acceptable salt, derivative, or metabolite thereof.

In certain embodiments, the pharmaceutic compost ion is administered subject about 48 hours to about 3 weeks prior to a stressor. In certain embodiments, the pharmaceutic composition is administered to the subject about 72 hours to about 2 weeks prior to a stressor.

In certain embodiments, the pharmaceutic composition is administered to the subject about 1 week prior to a stressor. In certain embodiments, the pharmaceutic composition is administered to the subject once prior to a stressor. In certain embodiments. the pharmaceutic composition is administered orally, intravenously, intranasally, or via injection to the subject.

In certain embodiments, the pharmaceutic composition comprises metabolites, including norketamine, hydroxyketamines, dehydronorketamine and hydroxynorketamine (HNK). In certain embodiments, the pharmaceutic composition comprises the ketamine metabolite (2R,6R)-HNK or (2S,6S)-HNK.

In certain embodiments, the stress-induced affective disorder comprises major depressive disorder and/or posttraumatic stress disorder (PTSD). In certain embodiments, the stress-induced affective disorder is selected from the group consisting of: depressive-like behavior and associated affective disorders, anhedonic behavior and associated affective disorders, anxiety and associated affective disorders, cognitive impairments and deficits and associated disorders, and combinations thereof.

In additional embodiments, the stress-induced affective disorder comprises stress-induced psychopathology. In certain embodiments, the stress-induced psychopathology comprises depressive and/or anxious behavior.

In certain embodiments, the preventing or delaying stress-induced cognitive impairment and/or decline.

In certain embodiments, the method further comprises administering an effective amount of an anti-depressant, an anxiolytic, or combinations thereof.

In certain embodiments, the method further comprises administering an effective amount of a selective serotonin reuptake inhibitor (SSRI), or a pharmaceutically acceptable salt or derivative thereof.

In certain embodiments, the method further comprises administering an effective amount of fluoxetine, paroxetine, sertraline, riluzole, prazosin, lamotrigine, ifenprodil, or combinations thereof.

In additional embodiments, the subject is a mammal. In certain embodiments, the subject is a human.

In additional embodiments, the pharmaceutical composition is administered in a booster series.

BRIEF DESCRIPTION OF THE DRAWINGS

FIG. 1A is a schematic showing the experimental design. FIG. 1B is a graph showing that on day 2 of the forced swim test (FST), group housed (Ctrl)-saline (Sal) and Ctrl-ketamine (K) mice did not differ from each other. FIG. 1C is a graph showing that SD-K mice exhibited significantly less immobility time when compared with SD-Sal mice. FIG. 1D is a graph showing that average immobility time for minutes 3 to 6 was increased in the SD-Sal mice when compared with Ctrl-Sal mice. The SD-K mice displayed an average immobility time that was less than the SD-Sal mice. FIG. 1E shows traces of the exploration paths of the mice during dominant interaction (DI). FIG. 11; is a graph showing that SD-Sal mice spent significantly more time investigating the empty enclosure when compared with the Ctrl-Sal mice. Conversely, SD-K mice spent significantly less time investigating the empty enclosure when compared with the SD-Sal mice. FIG. 1G is a graph showing that SD-K mice spent considerably more time investigating a CD-1 mouse when compared with SD-Sal mice. Error bars represent±SEM. *p<0.05, p<0.01, *p<0.01. CFC, contextual fear conditioning; EPM, elevated plus maze; NSF, novelty suppressed feeding; Sac, sacrifice.

FIGS. 2A-2F are graphs showing the ketamine-induced protection against depressive-like behavior is dose-specific. FIG. 2A is a graph showing that on day 2 of the forced swim test (FST), social defeat (SD)-saline (Sal) mice displayed significantly more immobility time in the FST when compared with group housed (Ctrl)-Sal mice. FIG. 2B is a graph showing that SD-Sal and SD-ketamine (K) (110 mg kg$^{-1}$) mice did not differ in immobility. FIG. 2C is a graph showing that SD-K (30 mg kg$^{-1}$) mice displayed significantly less immobility time when compared with SD-Sal mice. FIG. 2D is a graph showing that SD-Sal and SD-K (90 mg kg$^{-1}$) mice did not differ in immobility time. FIG. 2E is a graph showing that for minutes 3 to 6 (averaged), SD-Sal mice displayed significantly more immobility in the FST when compared with Ctrl-Sal mice. SD-K (30 mg kg$^{-1}$) mice again displayed decreased immobility when compared with SD-Sal mice. FIG. 2F is a graph showing that following a brief stressor, SD-Sal mice had significantly lower levels of corticosterone when compared with Ctrl-Sal mice. (n=male mice per group). Error bars represent±SEM. *p<0.05.

FIG. 3A is a schematic showing experimental design. FIG. 3B is a graph showing that activity in the habituation phase during testing did not differ between groups. FIGS. 3C-D are graphs showing that the latency to escape the shock was significantly less in the K-injected mice (indicated by the solid line) when compared with the saline (Sal)-injected mice (indicated as the dotted line). FIG. 3E is a graph showing that the total session length for all 30 trials was significantly less in the K-injected mice when compared with the Sal-injected mice. (n=8-9 male mice per group). Error bars represent±SEM. *p<0.05. ITI, inter-trial interval; ns, nonsignificant.

FIGS. 4A-4F are schematics and graphs showing, that ketamine (K) protects against depressive-like and anxiety behavior induced with a neuroendocrine model. FIG. 4A is a schematic showing the experimental paradigm. FIGS. 4B-C are graphs showing that corticosterone (CORT) mice administered K (90 mg kg$^{-1}$) or fluoxetine (Flx) (18 mg kg$^{-1}$/day) exhibited significantly reduced immobility in the forced swim test (FST). FIG. 4D is a graph showing that chronic CORT increased the latency to groom during the sucrose splash test (ST). In contrast to Flx, K for the highest doses tested (90 mg kg$^{-1}$) decreased the latency to groom during the ST. FIG. 4E is a graph showing that K (10 and 90 mg kg$^{-1}$) decreased the latency to feed in the novelty suppressed feeding (NSF). FIG. 4F is a graph showing that K (90 mg kg$^{-1}$) increased home food consumption in the NSF. (n=10-15 male mice per group). Error bars represent±SEM. #p<0.05, ##p<0.01. EPM, elevated plus maze; Sal, saline; Veh, vehicle.

FIG. 5B is a graph showing that average immobility time during week 1 was not significantly different in all groups of mice. However, average immobility during week 2 of SD was significantly altered in mice administered ketamine. FIG. 5C is a graph showing that the percent of time vocalizing did not differ between groups. FIG. 5D is a graph showing that the number of approaches by the 129S6/SvEv mouse to the CD-1 did not differ between the groups. FIGS. 5E-G are graphs showing that interestingly, the latency of the CD-1 to attack the 129S67SvEv mouse only differed in SD-K (30 mg kg$^{-1}$) mice when compared with SD-Sal mice. n=7-8 male 129S6/SvEy mice per group. Error bars represent±SEM. *p<0.05, p<0.01; *p<0.001.

FIGS. 6A-6L are graphs and schematics showing that ketamine, as an antidepressant, increases adult hippocampal neurogenesis. FIGS. 6A-B are graphs showing that ketamine significantly decreased the latency to approach the food pellet in Ctrl mice. SD-Sal and SD-K mice did not differ from one another. FIG. 6C is a graph showing that body weight did not differ in any of the groups of mice before the start of novelty suppressed feeding (NSF). FIG. 6D is a graph showing that before NSF, SD-Sal mice lost more body weight than Ctrl-Sal mice. Ketamine attenuated this weight loss. FIG. 6E is a graph showing that SD mice lost more body weight than Ctrl mice during the fast for NSF. FIG. 6F is a graph showing that SD mice consumed significantly more food than Ctrl mice. FIGS. 6G-J are results showing that all groups of mice had comparable levels of freezing during CFC training and following re-exposure to the fearful context A and to a similar context A'. n=13-15 129S6/SvEv male mice per group. FIG. 6K is a graph showing that ketamine increases the number of Ki67$^+$ cells when compared to saline in Ctrl mice but not in SD mice. FIG. 6L is a graph showing that ketamine does not alter DCX levels. n=6-9 129S6/SvEv male mice per group. Error bars represent±SEM. *p<0.05, p<0.01, *p<0.001. FIGS. 6K-L are immunohistochemistry results.

FIG. 7A is a schematic showing the experimental design. FIG. 7B is a graph showing that during CFC training, mice injected with saline or ketamine displayed similar levels of freezing. FIG. 7C is a graph showing that both groups of mice traveled comparably during each of the 3 shock presentations FIG. 7D is a graph showing that during the first extinction exposure, prophylactic ketamine-injected mice expressed significantly less freezing behavior when compared with saline-injected mice. Both groups of mice expressed similar levels of freezing behavior during subsequent extinction trials, reinstatement, and secondary extinction trials. FIG. 7E is a graph showing the differences in fear extinction between ketamine-injected and saline-injected mice. (n=5 mice per group). Error bars represent+SEM. p<0.01, and *p<0.001. Sal, saline; K, ketamine; CFC, contextual fear conditioning; E, extinction; R, reinstatement; No., number.

FIG. 8A is a schematic showing the experimental design. FIG. 8B is a graph showing that during CFC, mice injected with saline or ketamine displayed similar levels of freezing. FIG. 8C is a graph showing that both groups of mice traveled comparably during each of the 3 shock presentations. FIG. 8D is a graph showing that mice administered saline or ketamine 1 month before CFC exhibited similar levels of freezing behavior during CFC training and during extinction. (n=5 mice per group). Error bars represent+SEM. p<0.01, and *p<0.001. Sal, saline; K, ketamine; CFC, contextual fear conditioning; E, extinction; No., number.

FIGS. 9A-9H are experimental design schemes and graphs showing that prophylactic ketamine administration immediately before CFC does not result in a decreased fear response or facilitate extinction. FIG. 9A is a schematic showing the experimental design. FIG. 9B is a graph showing that during CFC, ketamine-injected mice have increased immobility before the shock presentation when compared with saline-injected mice. FIG. 9C is a graph showing that ketamine-injected mice travel less during the shock presentation than saline-injected mice. FIG. 9D is a graph showing that both groups express equal levels of freezing behavior during almost all extinction trials. (n=10 mice per group). FIG. 9E is a schematic showing the experimental design. FIG. 9F is a graph showing that mice injected with, saline or with ketamine expressed equal levels of freezing behavior during CFC training. FIG. 9G is a graph showing that saline- and ketamine-injected mice traveled equally during the shock presentation. FIG. 9H is a graph showing that both groups of mice displayed similar levels of freezing behavior during all but one extinction trial. (n=5 mice per group). Error bars represent+SEM, *p<0.05, and **p<0.01. Sal, saline; K, ketamine; CFC. contextual fear conditioning; E, extinction; No., number.

FIG. 10A is a schematic showing the experimental design. FIG. 10B is a graph showing that mice injected with saline or with ketamine 1 h after CFC express equal levels of freezing behavior during all extinction trials. (n=5 mice per group). FIG. 10C is a schematic showing the experimental design. FIG. 10D is a graph showing that mice injected with saline or with ketamine 1 week after CFC, but 1 week before extinction, expressed equal levels of freezing behavior during all extinction trials. (n=10 mice per group). FIG. 10E is a schematic showing the experimental design. FIG. 10F is a graph showing that mice injected with saline or with ketamine 1 h before extinction expressed equal levels of freezing behavior during all extinction trials. (n=5 mice per group). Error bars represent+SEM. Sal, saline; K, ketamine; CFC, contextual fear conditioning; E, extinction; No., number.

FIGS. 11A-11L are experimental design schemes and graphs showing that ketamine administration following extinction does not buffer against subsequent fear-inducing stimuli but increases vigilance. FIG. 11A is a schematic showing the experimental design. FIG. 11B is a graph showing that mice injected with saline or with ketamine 24 h after the last extinction trial expressed equal levels of freezing behavior during reinstatement and during secondary extinction trials. FIG. 11C is a graph showing that both groups of mice traveled comparably during the reinstatement shock presentation. FIG. 11D is a graph showing that both groups of mice exhibited equal levels of immobility in the EST on day 1 and on day 2. FIG. 11E is a graph showing that both groups of mice exhibited equal levels of movement in the OF. FIG. 11F is a graph showing that ketamine-injected mice displayed an increased number of rearing bouts when compared with saline-injected mice. (n=5 mice per group). FIG. 11G is a schematic showing the experimental design. FIG. 11H is a graph showing that saline and ketamine-injected mice displayed comparable levels of fear behavior during reinstatement and during secondary extinction trials. FIG. 11I is a graph showing that both groups of mice traveled comparably during each of the 3 reinstatement shock presentations. FIG. 11J is a graph showing that both groups of mice exhibit equal levels of immobility in the FST on day 1 and on day 2. FIGS. 11K-L are graphs showing that both groups of mice exhibited equal levels of movement in the OF and had a comparable number of rearing bouts. (n=9-10 mice per group). Error bars represent+SEM. *p<0.05. Sal, saline; K, ketamine; CFC, contextual fear conditioning; F, extinction; R, reinstatement; FST, forced swim test; OF, open field; No., number.

FIG. 12A is a schematic showing the experimental design. FIG. 12B is a graph showing that mice injected with saline and ketamine 1 h after 1-shock reinstatement express comparable levels of fear behavior during secondary extinction trials. (n=5 mice per group). FIG. 12C is a schematic showing the experimental design. FIG. 12D is a graph showing that mice injected with ketamine 1 h after 3-shock reinstatement express decreased fear when compared with mice injected with saline. (n=9-10 mice per group). FIG. 12E is a graph showing that mice injected with saline or ketamine 24 h after 3-shock reinstatement express comparable levels of freezing behavior during secondary extinction trials. (n=5 mice per group). Error bars represent+SEM. *p<0.05, and **p<0.01. Sal, saline; K, ketamine; CFC, contextual fear conditioning; E, extinction; R, reinstatement; No., number.

FIG. 13A shows results for 1 month or 1 week prophylactic administration of ketamine compared with saline injected mice. FIG. 13B shows results for 1 hour after CFC or 1 hour before extinction administration of ketamine compared with saline injected mice. FIG. 13C shows results for 1 week before reinstatement or 1 hour after reinstatement administration of ketamine compared with saline injected mice.

FIG. 14A shows the Experimental design. Mice were administered 3-shock CFC training. Four days later, they were placed in the same context for 3 minutes once per day for 10 days. FIG. 14B shows freezing levels for mice throughout the extinction trials. Mice expressed less than 20 percent freezing at the seventh extinction trial. FIG. 14C shows experimental design. Mice were administered 3-shock CFC training. Four days later, they were placed in the same context for 30 minutes twice per day for 8 days. FIG. 14D is a graph showing freezing levels for mice throughout the extinction trials. Values represent the first three minutes of each trial. Mice expressed less than 20 percent freezing at the third extinction trial. n=7-11 mice per group.

FIG. 15A is a schematic of the experimental design for prophylactic administration of ketamine metabolites. FIG. 15B is a graph illustrating that prophylactic K-injected mice expressed significantly less immobility in day 2 of the FST when compared with Sal-injected mice. Moreover prophylactic metabolites of ketamine (HNK) are efficacious as prophylactics at 10 and 30 mg/kg. *p<0.05, p<0.01, *p<0.001.

DETAILED DESCRIPTION OF THE INVENTION

Figure 1A:
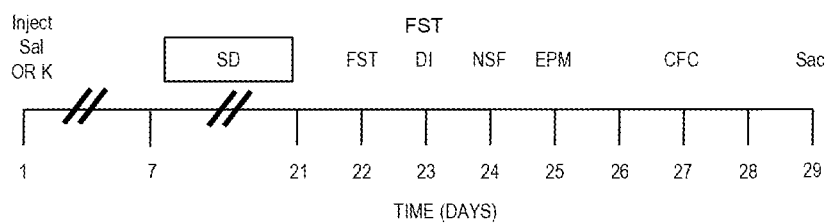
FIGS. 1A-1G are schematics and graphs showing that ketamine protects against depressive-like behavior following social defeat (SD).

The idea that increasing stress resilience could protect against the development of psychiatric disorders is appealing, but treatments to increase resilience are still in their infancy. Current interventions are all behavioral, with psychotherapy and exercise being the best available tools to increase resilience (6-8). Traditionally, affective disorders have been treated from a symptom-suppression approach. Existing drugs aim to mitigate the impact of these chronic diseases, but do not cure or prevent the disease itself, There are no known cures. Antidepressants are typically used to treat existing depressive symptoms, but chronic antidepressant treatment may also protect against subsequent depressive episodes (17-21). This is known as "tertiary prevention" or "tertiary prophylaxis." Tertiary preventions suppress symptoms and mitigate the impact of a chronic disease, but do not treat the underlying disease. Maintenance treatment in MDD patients is often referred to as prophylaxis against the development of additional depressive episodes (22), but this should not be confused with "primary prevention" or "primary prophylaxis," which aims to prevent the disease before it ever occurs. No antidepressants have yet been shown to be primary prophylactics. Whether these tertiary prophylactic antidepressants, which can decrease the incidence of symptomatic episodes in disordered individuals, are also able to work as primary prophylaxis and prevent de, novo psychiatric disorders remains to be tested. Importantly, classical antidepressant efficacy is neither sufficient for, nor necessarily predictive of, primary prophylactic efficacy. For example, fluoxetine does not demonstrate such primary prophylactic efficacy.

The results described herein address and illustrate that ketamine and ketamine metabolites exhibit such primary prophylactic efficacy. The present disclosure provides methods for prophylactically treating a stress-induced affective disorder or stress-induced psychopathology in a subject. Also encompassed by the present disclosure are methods for inducing and/or enhancing stress resilience in a subject. In certain embodiments, an effective amount of an antagonist of the glutamate N-methyl-D-aspartate (NMDA) receptor, such as ketamine or a pharmaceutically acceptable salt or derivative thereof, is administered to a subject prior to a stressor.

The present agent/composition may be administered therapeutically to achieve a therapeutic benefit or prophylactically to achieve a prophylactic benefit. By therapeutic benefit is meant eradication or amelioration of the underlying stress-induced affective disorder being treated, and/or eradication or amelioration of one or more of the symptoms associated with the underlying disorder. By prophylactic benefit is meant prevention or delay of the onset of a stress-induced affective disorder, and/or prevention or delay of the onset of one or more of the symptoms associated with a stress-induced affective disorder. In certain embodiments, an effective amount of the present agent/composition to be administered prevents stress-related disorders from developing or being exacerbated into more serious conditions.

In certain embodiments, for prophylactic administration, the present agent/composition may be administered to a patient at risk of developing a stress-induced affective disorder, or to a patient reporting one or more of the physiological symptoms of a stress-induced affective disorder, even though a diagnosis of a stress-induced affective disorder may not have yet been made. In certain embodiments, prophylactic administration is applied to avoid the onset of the physiological symptoms of the underlying disorder, before the symptom manifests cyclically. In this latter embodiment, the therapy is prophylactic with respect to the associated physiological symptoms instead of the underlying indication. In certain embodiments, the present agent/composition is administered prior to recurrence of a stressor. In certain embodiments, the present agent/composition is administered prior to the onset of a particular symptom.

In a further embodiment, the present invention provides for the use of the present agent or a pharmaceutically acceptable salt or solvate thereof, or a physiologically functional derivative thereof, in the preparation of a medicament for the treatment of a stress-induced affective disorder.

"Treating" or "treatment" of a state, disorder or condition includes:
(1) preventing or delaying the appearance of clinical symptoms of the state, disorder, or condition developing in a person who may be afflicted with or predisposed to the state, disorder or condition but does not yet experience or display clinical symptoms of the state, disorder or condition; or
(2) inhibiting the state, disorder or condition, i.e., arresting, reducing or delaying the development of the disease or a relapse thereof (in case of maintenance treatment) or at least one clinical symptom, sign, or test, thereof; or
(3) relieving the disease, i.e., causing regression of the state, disorder or condition or at least one of its clinical or sub-clinical symptoms or signs.

The benefit to a subject to be treated is either statistically significant or at least perceptible to the patient or to the physician.

A "prophylactically effective amount" refers to an amount effective, at dosages and for periods of time necessary, to achieve the desired prophylactic result. In certain embodiments, since a prophylactic dose is used in subjects prior to or at an earlier stage of a disorder, the prophylactically effective amount is less than the therapeutically effective amount. In certain embodiments, the prophylactically effective amount is similar to, identical to, or more than, the therapeutically effective amount.

A therapeutically effective amount, or an effective amount, of a drug is an amount effective to demonstrate a desired activity of the drug. A "therapeutically effective amount" will vary depending, on the compound, the disorder and its severity and the age, weight, physical condition and responsiveness of the subject to be treated. In certain embodiments, a effective amount of ketamine, or a pharmaceutically acceptable salt or solvate thereof, or a physiologically functional derivative thereof, is an amount effective to prevent or delay the onset of a stress-induced affective disorder, and/or effective to alleviate, one or more of the symptoms of a stress-induced affective disorder.

In certain embodiments, an effective amount of the present agent is a sub-anesthetic amount of ketamine, or a pharmaceutically acceptable salt or solvate thereof, or a physiologically functional derivative thereof. In certain embodiments, an effective amount of the present agent is a sub-analgesic amount of ketamine, or a pharmaceutically acceptable salt or solvate thereof, or a physiologically functional derivative thereof.

In certain embodiments, a subject is treated with ketamine, or a pharmaceutically acceptable salt or solvate thereof, or a physiologically functional derivative thereof, via intravenous, oral, transdermal or intranasal administration. In certain embodiments, a subject is injected with ketamine, or a pharmaceutically acceptable salt or solvate thereof, or a physiologically functional derivative thereof.

In certain embodiments, a subject is treated with a single dose of an effective amount of ketamine, or a pharmaceutically acceptable salt or solvate thereof, or a physiologically functional derivative thereof, prior to and/or after a stressor. In some aspects, a subject is treated with multiple doses of an effective amount of ketamine, or a pharmaceutically acceptable salt or solvate thereof, or a physiologically functional derivative thereof, prior to and/or after a stressor.

In certain embodiments, the present agent, such as ketamine, or a pharmaceutically acceptable salt or solvate thereof, or a physiologically functional derivative thereof, is administered in a composition comprising a pharmaceutically acceptable carrier, excipient or diluent. Also provided herein is a pharmaceutical composition that comprises ketamine, or a pharmaceutically acceptable salt or solvate thereof, or a physiologically functional derivative thereof, and a pharmaceutically acceptable earlier, excipient or diluent, for use in the prophylactic treatment of a stress-induced affective disorder.

"Patient" or "subject" refers to mammals and includes human and veterinary subjects. In certain embodiments, the subject is mammalian.

Ketamine

Ketamine ((RS)-2-(2-chlorophenyl)-2-(methylamino)cyclohexanone) is an antagonist of the glutamate N-methyl-D-aspartate (NMDA) receptor (NMDAR). Ketamine also acts on opioid receptors, sigma receptors, muscarinic receptors, monoamine transporters, etc.

Ketamine is a chiral compound. As used herein, the term "ketamine" may refer to (S)-ketamine (also referred to as S(+)-ketamine or esketamine), (R)-ketamine (R(−)-ketamine), or a racemic mixture of (S)-ketamine and (R)-ketamine. In certain embodiments, the ketamine compositions contain different proportions of the S(+) and R(−) stereoisomers. In certain embodiments, the ketamine compositions contain only (S)-ketamine or (R)-ketamine, or are enantiomerically enriched for a ketamine enantiomer. In certain embodiments, the ketamine composition is enriched to contain, for example, greater than 60%, greater than 70%, greater than 80%, greater than 90%, greater than 95%, greater than 99%, or greater than 99.9 of (S)-ketamine or (R)-ketamine.

Paul et al., "Comparison of racemic ketamine and S-ketamine in treatment-resistant major depression: report of two cases", World J. of Bio, Psych., 2009, pp 241-244, Vol. 10(3); Paskalis et al., Oral Administration of the NMDA Receptor Antagonist S-Ketamine as Add-on Therapy of Depression: A Case Series, Pharmacopsychiatry, 2010. pp 33-35. Vol. 40; Noppers et al., Absence of long-term analgesic effect from a short-tend S-ketamine infusion on fibromyalgia pain: A randomized, prospective, double blind, active placebo-controlled trial", Eur. J, of Pain., 2011, 15(9): 942-9 Matthews et al., Ketamine for Treatment-Resistant Unipolar Depression, CNS Drugs, 2012, 1-16; and International Patent Publication No. WO2013138322.

The term "pharmaceutically acceptable derivative" refers to any pharmaceutically acceptable salt, solvate or prodrug, e.g. ester, of a compound which upon administration to the recipient is capable of providing (directly or indirectly) a compound or an active metabolite or residue thereof. Such derivatives are recognizable to those skilled in the art, without undue experimentation, Derivatives are described, for example, in Burger's Medicinal Chemistry and Drug Discovery, 5th Edition, Vol 1: Principles and Practice, which is incorporated herein by reference. In certain embodiments, pharmaceutically acceptable derivatives include salts, solvates, esters, carbamates, and phosphate esters. In one embodiment, the present composition contains a hydrochloride salt of ketamine.

The present agent may be administered by various routes, including intravenous i.v. or IV), intranasal (i.n. or IN), intramuscular (i.m. or IM), candid, intrathecal, and subcutaneous (s.c.) routes.

NMDA Receptor Antagonists—Ketamine and Other Compounds

NMDA receptor antagonists are compounds that antagonize, or inhibit, the action of the NMDA receptor. An NMDA receptor antagonist may be a competitive antagonist, an uncompetitive antagonist, a noncompetitive antagonist, and/or a glycine antagonist.

Non-limiting examples of NMDA receptor antagonists include, ketamine, dextromethorphan (DXM), histogranin, memantine, meperidine, methadone, methoxetamine (MXE), phencyclidine (PCP), nitrous oxide ($N_2O$), AP5 (APV, R-2-amino-5-phosphonopentanoate), AP7 (2-amino-7-phosphonoheptanoic acid), CPPene ((3-[(R)-2-carboxypiperazin-4-yl]-prop-2-enyl-1-phosphonic acid), Selfotel, Amantadine, Atomoxetine, AZD6765, Agmatine, chloroform, dextrallorphan, dextromethorphan, dextrorphan, diphenidine, dizocilpine (MK-801), ethanol, eticyclidine, gacyclidine, ibogaine, magnesium, memantine, nitromemantine, rolicyclidine, tenocyclidine, methoxydine, tiletamine. neramexane, eliprodil, dexoxadrol, etoxadrol, remacemide, delucemine, WMS-2539, NEFA, 8A-PDUQ, HU-211, Aptiganel (Cerestat, CNS-1102), rhynchophylline, kynurenic acid, Rapastinel (GLYX-13), NRX-1074, 7-Chlorokynurenic acid, 4-Chlorokynurenine (AV-101), TK-40, 1-Aminocyclopropanecarboxylic acid (ACPC), L-Phenylalanine, Xenon, or analogs or derivatives thereof. Ketamine derivatives such as Rapastinel or Glyx-13 are also included. Rapastinel is an NMDA receptor glycine site partial agonist. It is an amidated tetrapeptide (Thr-Pro-Pro-Thr-$NH_2$) which rapidly crosses the blood brain harrier, but is not active orally.

Compounds that are mechanistically similar to ketamine are expected to be protective against stress-induced de novo psychopathology. Such compounds include:

Ro 25-6981, a GluN2B-selective antagonist (Miller O H, et al. (2014), eLife 3:e03581), which has been shown to have rapid antidepressant actions in rodent models of depression.

CP-101,606, a GluN2B-selective antagonist (Preskom S, et al. (2007): A placebo-controlled trial of the NR2B specific NMDA antagonist CP-101, 606 plus paroxetine for treatment resistant depression (TRD). *American Psychological Association meeting*), which has been shown to be protective in animal models of brain injury and stroke.

GLYX-13, a novel N-methyl-D-aspartate receptor (NMDAR) glycine-site functional partial agonist and rapid-acting antidepressant (Burgdorf J, et al. (2(313). *Neuropsychopharmacology* 38:729-42). GLYX-13 received Breakthrough Therapy designation from the U.S. Food and Drug Administration (FDA) for adjunctive treatment of MDD in January, 2016, and CX546 (Tocris), an ampakine (an AMPA receptor agonist) (Zhou W, et al, (2014), *Ear. Psychiatry* 29:419-23), which relieves the respiratory depression induced by fentanyl.

Non-limiting examples of the NMDA receptor antagonists also include anti-receptor antibodies, anti-ligand antibodies, etc.

Several synthetic opioids function as NMDA receptor-antagonists, such as pethidine, methadone, meperidine, dextropropoxyphene, tramadol, levorphanol, and ketobemidone.

AMPA Receptor Agonists

AMPA receptor agonists are compounds that activate the action of the α-amino-3-hydroxy-5-methyl-4-isoxazolepropionic acid (AMPA) receptor. It is expected that compounds that activate the AMPA receptor, including metabolites, will have a similar effect as the present effects shown with ketamine, in view of recent findings that a ketamine metabolite's antidepressant activity in mice was due to sustained activation of the AMPA receptor, rather than inhibiting NMDAR. (See, Zanos et al., (2016). "NMDAR inhibition-independent antidepressant actions of ketamine metabolites. Nature, 533: 481-486.)

Thus, in certain embodiments, AMPA receptor agonists may be used in the methods described herein. Non-limiting examples of the AMPA receptor agonists include glutamate, AMPA, 5-fluorowillardiine, domoic acid, quisqualic acid, (2R,6R)-hydroxynorketamine, CX546, etc.

Ketamine Metabolites

Ketamine is a derivative of arylcyclohexylamine and contains a chiral center. Since the 1950s, a large number of arylcyclohexylamines have been synthesized: these compounds have shown a wide range of possible pharmacological activities. When administered orally, it undergoes first-pass metabolism, where it is stereo selectively metabolized into a broad array of metabolites, including norketamine, hydroxyketamines, dehydronorketamine and hydroxynorketamine (HNK). After ketamine administration, (2S,6S;2R, 6R)-HNK are the two major HNK metabolites found in the plasma and brain. Interestingly, a recent study has shown that the (2R,6R)-HNK metabolite is: 1) essential for the antidepressant effects of ketamine, 2) dependent on α-amino-3-hydroxy-5-methyl-4-isoxazolepropionic acid (AMPA) receptor activation, and 3) non-hypnotic (Zanos et al., 2016). All of these compounds are expected to behave similarly in the presently described methods, including enantiomers and non-psychotomimetic metabolites of ketamine.

Figure 15A:
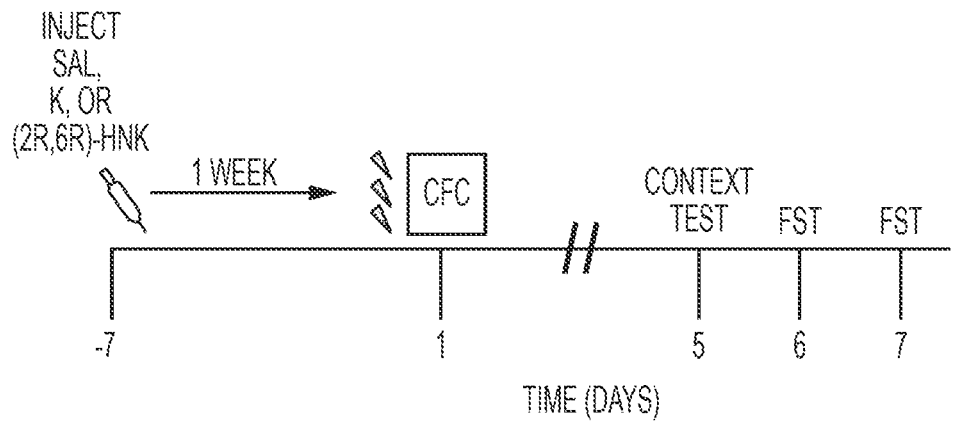
FIGS. 15A-B show the experimental design and graph illustrating that prophylactic metabolites of ketamine administration decrease behavioral despair.
Figure 15B:
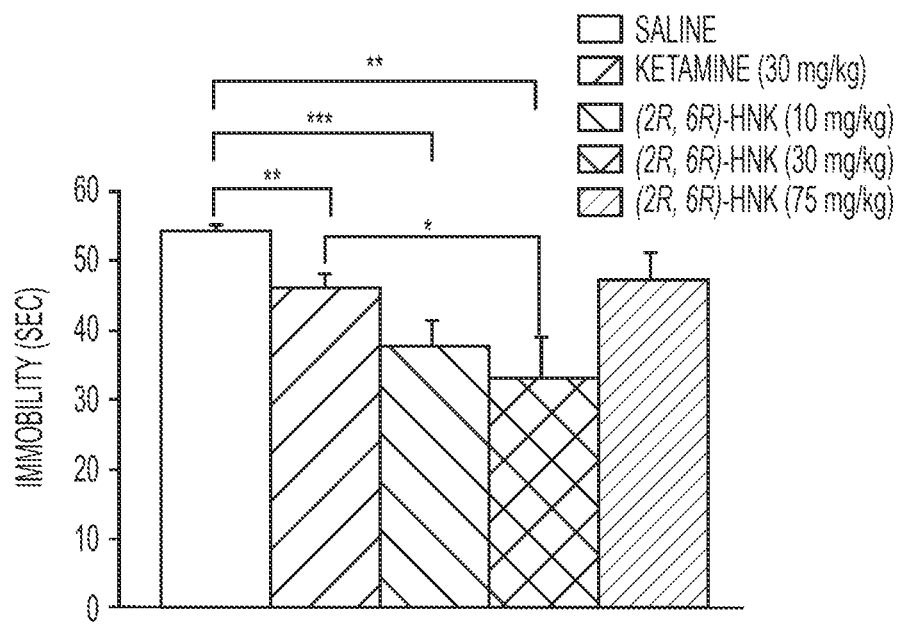

Ketamine's enantiomers and non-psychotomimetic metabolites are also expected to be protective against stress-induced de novo psychopathology, as shown in the results in FIGS. 15A-B. Such compounds include:

1. (2R,6R)-HNK, a metabolite of ketamine that may mediate the antidepressant effects of ketamine and lacks the ketamine-related side effects (Zanos et al., 2016) (see FIGS. 15A-B)
2. (2S,6S)-HNK, a metabolite of ketamine (Zanos et al., 2016, synthesis of these compounds (2R,6R)-HNK and(2S,6S)-HNK are described in Zanos et al. 2016 and Wainer et al. WO 2013/056229 (2013), The use of (2R,(R)-hydroxynorketamine, (S)-dehydronorketamine and other stereoisomeric dehydro and hydroxylated metabolites of (R,S)-ketamine in the treatment of depression and neuropathic pain).
3. (R)-ketamine, the R-enantiomer of ketamine, which has rapid-onset and sustained antidepressant effects without psychotomimetic side effects (Yang et al., 2015), and
4. (S)-ketamine, the S-enantiomer of ketamine, which is being developed as an intranasal spray, currently in phase III clinical trials for treatment-resistant depression.

Finally, other ketamine analogs are also expected to be protective. Such compounds include:

5. Fluorodeschloroketamine, an analog of ketamine where the chlorine (Cl) group has been replaced by fluorine (F), and
6. Tiletamine, an analog of ketamine commonly used as a veterinary anesthetic.

Pharmaceutical Compounds

The compounds used in the present methods include all hydrates, solvates, and complexes of the compounds. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

When the structure of the compounds used in this invention includes an asymmetric carbon atom such compound can occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "*Enantiomers, Racemates and Resolutions*" by J. Jacques, A. Collet and S. Wilen, Pub. John Wiley & Sons, NY, 1981. For example, the resolution may be carried out by preparative chromatography on a chiral column.

The present disclosure is also intended to include use of all isotopes of atoms occurring on the compounds disclosed herein. Isotopes include those atoms having the same atomic number but different mass numbers. Isotopically-labeled compounds can generally be prepared by conventional techniques known to those skilled in the art or by processes analogous to those described in the Examples disclosed herein using an appropriate isotopically-labeled reagents in place of the non-labeled reagents employed.

The compounds of the instant invention may be in a salt form. As used herein, a "salt" is a salt of the instant compound which has been modified by making acid or base, salts of the compounds. In the case of compounds used for treatment of mammals, the salt is to pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, henzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately treating a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarase, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The present methods also encompass administering a physiologically functional derivative of the present compound. As used herein, the term "physiologically functional derivative" refers to a compound (e.g, a drug precursor) that is transformed in vivo to yield the present compound or its active metabolite, or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Dosages

In certain embodiments, the effective amount of the present compound is a dose of about 0.01 to about 3 mg of ketamine per kilogram of body weight of the subject (mg/kg), i.e., from about 0.01 mg/kg to about 3 mg/kg body weight. In certain embodiments, the effective amount of the present compound ranges 0.001 to approximately 3 mg/kg body weight, 0.001 to approximately 2 mg/kg body weight, from about 0.01 mg/kg to about 3 mg/kg body weight, from about 0.01 to about 2 mg/kg of body weight, about 0.01 to about 1.5 mg/kg of body weight, about 0.05 to about 1.4 mg/kg of body weight, about 0.05 to about 1.3 mg/kg of body weight, about 0.05 to about 1.2 mg/kg of body weight, about 0.05 to about 1.1 mg/kg of body weight, about 0.01 to about 1 mg/kg of body weight, or about 0.05 to about 0.7 mg/kg of body weight. In some aspects, the dose is about 0.05 to about 0.5 mg/kg. In some aspects, the dose is less than about 0.5 mg/kg, less that about 0.4 mg/kg, or less than about 0.3 mg/kg body weight. In some aspects, the effective amount of the present compound is a dose in the range of from about 0.01 mg/kg to about 1.5 mg/kg body weight. In some aspects, the effective amount of the present compound is a dose in the range of from about 0.01 mg/kg to about 1 mg/kg body weight. In some aspects, the effective amount of the present compound is a dose in the range of from about 0.0.1 mg/kg to about 0.75 mg/kg body weight. In some aspects, the effective amount of the present compound is a dose in the range of from about 0.75 mg/kg to about 1.5 mg/kg body weight. In some aspects, the effective amount of the present compound is a dose in the range of from about 0.5 mg/kg to about 1.2 mg/kg body weight. In some aspects, the effective amount of the present compound is a dose in the range of from about 0.05 mg/kg to about 0.5 mg/kg. In some aspects, the effective amount of the present compound is a dose of about 0.2 mg/kg or about 0.4 mg/kg body weight. In some aspects, the dose of the present compound is about 0.01 to about 1 mg/kg, about 0.1 to about 0.5 mg/kg, about 0.8 to about 1.2 mg/kg, about 0.7 to about 1.1 mg/kg, about 0.05 to about 0.7 mg/kg, about 0.01 mg/kg, about 0.05 mg/kg, about 0.1 mg/kg, about 0.2 mg/kg, about 0.3 mg/kg, about. 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg, or about 3 mg/kg body weight.

In certain embodiments, the dose of the present compound per administration is from about 1 to about 250 mg, from about 10 mg to about 300 mg, about 10 mg to about 250 mg, about 10 to about 200 mg, about 15 to about 175 mg, about 20 to about 175 mg, about 8 mg to about 32 mg, about 50 mg to about 75 mg, about 2.5 to about 1.50 mg, about 25 to about 125 mg, about 25 to about 100 mg, about 50 to about 100 mg, about 50 mg to about 75 mg about 75 mg to about 100 mg, or about 75 mg to about 200 mg, about 1 mg, 2 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 1.30 mg, 140 mg, 150 mg, 160 mg, 170 mg, 180 mg, 190 mg, 200 mg, 210 mg, 220 mg, 230 mg, 240 mg, and 250 mg. In some aspects, the dose of the present compound is about 50 mg. In some aspects, the dose of the present compound is about 75 mg. In some aspects, the total dose of the present compound is about 100 mg.

In some aspects, the therapeutically effective amount of the present compound is a sub-anesthetic dose. In some aspects, the therapeutically effective amount of the present compound is a sub-analgesic dose. In certain embodiments, the therapeutically effective amount of the present compound is below the level that results in one or more side effects of the compound. In certain embodiments, the therapeutically effective amount of the present compound is an anesthetic dose or analgesic dose. U.S. Patent Publication No. 20160067196.

In some aspects, the (therapeutically) effective amount of the present compound is about 0.01 mg to about 1.000 mg, from about 0.01 mg to about 500 mg, from about 0.1 mg to about 250 mg, or any amount or range therein. In another aspect, the (therapeutically) effective amount of the present compound is, e.g., 0.01 mg, 0.025 mg, 0.05 mg, 0.1 mg, 0.5 mg, 1 mg, 5 mg, 10 mg, 25 mg, 50 mg, 55 mg, 60 mg, 65 mg, 70 mg, 75 mg, 80 mg, 90 mg, 95 mg, 100 mg, 150 mg, 200 mg, 250 mg, or 500 mg.

In certain embodiments, a therapeutically effective dose of the present compound may be adjusted depending on conditions of the disease/disorder to be treated or prophetically treated, the age, body weight, general health conditions, sex, and diet of the subject, dose intervals, administration routes, excretion rate, and combinations of drugs.

An initial dose, of the present compound may be, larger, followed by one or more smaller maintenance doses. Other ranges are possible, depending on the subject's response to the treatment. An initial dose may be the same as, or lower or higher than subsequently administered doses.

The dose may be administered daily, weekly, biweekly, several times daily, semi-weekly, every other day, bi-weekly, quarterly, several times per week, semi-weekly, monthly etc., to maintain an effective dosage level. The duration and frequency of treatment may depend upon the subject's response to treatment.

In certain embodiments, a subject may be administered 1 dose, 2 doses, 3 doses, 4 doses, 5 doses, 6 doses or more of the present composition. In certain embodiments, a single dose of the present agent/composition is administered in the present method. In certain embodiments, multiple doses of the present agent/composition (e.g., 2 doses, 3 doses, 4 doses, 5 doses, 6 doses, 7 doses, 8 doses, 9 doses, 10 doses or more) are administered in the present method.

In certain embodiments, when there are more than one doses of the present compound/composition administered to a subject, the second dose is lower than the first dose. In certain embodiments, the second dose is an amount that is at most one-half, one-quarter, or one-tenth the amount of the first dose.

The number and frequency of doses may be determined based on the subject's response to administration of the composition, e.g., if one or more of the patient's symptoms improve and/or if the subject tolerates administration of the composition without adverse reaction.

In certain embodiments, the present agent/composition is administered at least once a day, at least twice a day, at least three times per day, or more. In certain embodiments, the present agent/composition is administered at least once a week, at least twice a week, at least three times per week, or more frequently. In certain embodiments, the present agent/composition is administered at least twice per month, or at least once per month.

Treatment using the present method can continue as long as needed.

Dosing Time Frame

In certain embodiments, the present agent/composition is administered to a subject prior to a stressor. In certain embodiments, the present agent/composition is administered to a subject both prior to and after a stressor. In certain embodiments, the present agent/composition is administered to a subject after a stressor. In certain embodiments, the present agent/composition is administered to a subject prior to a stressor, and again prior to a recurrence of the stressor or a different stressor.

In certain embodiments, the present agent/composition is administered to the subject about 12 hours to about 4 weeks, about 18 hours to about 4 weeks, about 1 day to about 3.5 weeks, about 2 days to about 3 weeks, about 3 days to about 3 weeks, about 4 days to about 3 weeks, about 5 days to about 3 weeks, about 6 days to about 3 weeks, about 2 days to about 2.5 weeks, about 3 days to about 2.5 weeks, about 4 days to about 2.5 weeks, about 5 days to about 2.5 weeks, about 6 days to about 2.5 weeks, about 1 week to about 2.5 weeks, about 1 week to about 2.5 weeks, about 1 week to about 2 weeks, about 3 days, about 4 days, about 5 days, about 6 days, about 1 week, about 8 days, about 9 days, about 10 days, about 11 days, about 12 days, about 13 days, about 2 weeks, about 2.5 weeks, about 3 weeks, about 3.5 weeks, or about 4 weeks, prior to, and/or after a stressor.

In certain embodiments, the administration of the present agent/composition is continued over a period of up to 2 days, up to 3 days, up to 4 days, up to 5 days, up to 6 days, up to 1 week, up to 2 weeks, up to 3 weeks, up to 4 weeks, 2 weeks, 3 weeks, 4 weeks, 5 weeks, 6 weeks, 7 weeks, 8 weeks, 9 weeks, 10 weeks, or longer.

In certain embodiments, the present agent/composition is administered once, twice, at least twice, at least three times, at least four times, at least five time, at least six times, at least seven times, at least eight times, at least nine times, or more per treatment.

In certain embodiments, the present agent/composition is administered at least once a day, at least twice a day, at least three times per day, at least once a week, at least twice a week, at least three times a week, at least once per month, at least twice per month, or more frequently. Treatment can continue as long as needed.

Stressors

A stressor is a stimulus that causes stress. It can be an event or other factor that disrupts the body's homeostasis of temperature, blood pressure, and/or other functions, in certain embodiments, a stressor is a traumatic or stressful event. Because humans have sophisticated brains and thought processes, anticipating a disruption can also be a stressor. In certain embodiments, a stressor is injury, trauma, combat, warfare, surgery, an accident, a criminal assault, child abuse, natural or human-caused disasters, a crash, grief, hunger, heat, cold, chemical exposure, autoimmune disease, infectious disease, viral infection, cancer, exhaustion, physical distress, neuropathy, hyperalgesia, allodynia, emotional distress, or depression. A traumatic event may be an event or something that threatens the person's life or the life of a close one or it could be something witnessed. U.S. Patent Application No. 20140018339.

A stressor may be acute, or may be chronic.

There are numerous physiological processes that are altered in response to stress. Among these are altered cortisol, corticotropin, catecholamine and serotonin levels. These levels return to baseline after an acute stressor is removed (McEwen N Eng J Med 1998 338(3):171-179). These biochemical markers of stress in turn lead to ill health and psychosocial disorders. Consequently, stress plays a major role in physical and mental health. Stress can affect the onset of, or susceptibility to disease. It can also affect the progression or course of disease even when there is another underlying pathophysiology of the disease. Recovery from an existing disease can also be delayed due to stress. For example, stress is a contributing factor to high blood pressure, heart disease, headaches, colitis, irritable bowel syndrome, temporo-mandibular joint disorder, cancer, peptic ulcers, insomnia, skin disorders and asthma. Stress can also aggravate other conditions such as multiple sclerosis, diabetes, herpes, mental illness, substance abuse and psychiatric disorders characterized by the presence of violent or aggressive tendencies. Particularly, stress contributes to functional somatic disorders, affective disorders and major depressive disorder. These include disorders such as chronic fatigue syndrome (CFS), fibromyalgia (FMS), Gulf War Syndrome, anxiety and post-traumatic stress disorder (PTSD). Stressors that disrupt normal exercise or sleep patterns.

Additional examples of use include administration prior to military deployment to protect Service members (active combat soldiers, battlefield surgeons, etc.) and even military working dogs against stress. Potential non-military use cases include, but are not limited to: police, firefighters, first responders, EMTs, ER doctors, prison guards (and prisoners), humanitarian aid workers, and refugees.

In certain embodiments, a subject may be administered the present agent or composition prior to a situation in which the subject (such as an early responder or military personnel) is likely to be exposed to traumatic stress, immediately after exposure to traumatic stress, and/or when the subject feels that his or her PTSD symptoms are likely to appear.

Resilience to Stress

Resilience to stress refers to the capacity of a subject to adapt or change successfully, and/or to maintain physiological, neurological, or psychological homeostasis, in the face of a stressor (e.g., adversity). As used herein, the term "enhancing resilience" refers to increasing the ability of a subject to experience a stressor (e.g., a traumatic event) without suffering a stress-induced affective disorder, and/or with less post-event symptomatology or disruption of homeostasis and/or normal activities of daily living. In certain embodiments, improving resilience can prevent a stress-induced affective disorder, in certain embodiments, improving resilience can reduce at least one of the signs, symptoms, or symptom clusters of a stress-induced affective disorder. In certain embodiments, the present method enhances a subject's resilience to stress, helps protect against developing stressor-related psychopathology, decrease the functional consequences of stressor-induced disorders (e.g., PTSD, etc.), and reduce medical morbidity and mortality.

The Connor-Davidson Resilience Scale (CD-RISC) is a 25-item self-report scale, each rated on at 5-point scale (0-4), with higher scores reflecting greater resilience (Connor K M & Davidson, J R T. Development of a new resilience scale: the Connor-Davidson Resilience Scale (CD-RISC). Depression and Anxiety, 2003: 18: 71-82).

Resilience, psychological growth and life satisfaction may be measured with the CD-RISC, the Purpose in Life Scale, the abbreviated MOS Social Support Survey, the PTGI, and the Q-LES-Q.

Combination Therapy

The present compound or composition may be administered to a subject alone, or may be administered to a subject in combination with one or more other treatments/agents.

In certain embodiments, the second agent is an antidepressant, an anxiolytic, or combinations thereof. In certain embodiments, the second agent is a serotonin reuptake inhibitor (SRI), or a selective serotonin reuptake inhibitor (SSRI). In certain embodiments, the second agent is fluoxetine, paroxetine, sertraline, lithium, riluzole, prazosin, lamotrigine, ifenprodil, or combinations thereof. In certain embodiments, the second agent is a dual serotonin norepinephrine reuptake inhibitor compound (DRI). In certain embodiments, the second agent is venlafaxine, duloxetine, milnacipran, or combinations thereof. In certain embodiments, the second agent is a non-tricyclic triple reuptake inhibitor (TRI).

In certain embodiments, the present compound or composition is administered to a subject in combination with one or more treatments/agents such as antidepressants, analgesics, muscle relaxants, anorectics, stimulants, antiepileptic drugs, and sedative/hypnotics. Non-limiting examples of compounds that can be administered in combination with the present compound or composition include, neurontin, pregabalin, pramipexole, L-DOPA, amphetamine, tizanidine, clonidine, tramadol, morphine, tricyclic antidepressants, codeine, carbamazepine, sibutramine, amphetamine, valium, trazodone and combinations thereof.

In certain embodiments, combination therapy means simultaneous administration of the compounds in the same dosage form, simultaneous administration in separate dosage forms, or separate administration of the compounds.

In certain embodiments, the second agent/treatment is used as adjunctive therapy to the present compound or composition. In certain embodiments, the treatment includes a phase wherein treatment with the second agent/treatment takes place after treatment with the present compound or composition has ceased. In certain embodiments, the treatment includes a phase where treatment with the present compound or composition and treatment with the second agent/treatment overlap.

Combination therapy can be sequential or can be administered simultaneously. In either case, these drugs and/or therapies are said to be "co-administered." It is to be understood that "co-administered" does not necessarily mean that the drugs and/or therapies are administered in a combined form (i.e., they may be administered separately (e.g., as separate compositions or formulations) or together (e.g., in the same formulation or composition) to the same or different sites at the same or different times).

In certain embodiments, a subject is treated concurrently (or concomitantly) with the present compound or composition and a second agent. In certain embodiments, a subject is treated initially with the present compound or composition, followed by cessation of the present compound or composition treatment and initiation of treatment with a second agent. In certain embodiments, the present compound or composition is used as an initial treatment, e.g., by administration of one, two or three doses, and a second agent is administered to prolong the effect of the present compound or composition, or alternatively, to boost the effect of the present compound or composition. A person of ordinary skill in the art will recognize that other variations of the presented schemes are possible, e.g., initiating treatment of a subject with the present compound or composition, followed by a period wherein the subject is treated with a second agent as adjunct therapy to the present compound or composition treatment, followed by cessation of the present compound or composition treatment.

The present compound and the other pharmaceutically active agent(s) may be administered together or separately and, when administered separately this may occur simultaneously or sequentially in any order. The amounts of the present compound and the other pharmaceutically/active agent(s) and the relative timings of administration will be selected in order to achieve the desired combined therapeutic effect.

In various embodiments, the therapies (e.g., a composition provided herein and a second agent in a combination therapy) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In certain embodiments, the therapies are administered no more than 24 hours apart or no more than 48 hours apart. In certain embodiments, two or more therapies are administered within the same patient visit. In other embodiments, the composition provided herein and the second agent are administered concurrently. In other embodiments, the composition provided herein and the second agent are administered at about 2 to 4 days apart, at about 4 to 6 days apart, at about 1 week part, at about 1 to 2 weeks apart, or more than 2 weeks apart. In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months. In certain embodiments, a composition provided herein and a second agent are administered to a subject in a sequence and within a time interval such that the composition provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the composition provided herein and the second active agent exerts their effect at times which overlap. Each second active agent can be administered separately, in any appropriate form and by any suitable route. In other embodiments, the composition provided herein is administered before, concurrently or after administration of the second active agent. The term "about" refers to ±10% of the referenced value. In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day. The second agent can act additively or synergistically with the compound provided herein. In one embodiment, the composition provided herein is administered concurrently with one or more second agents in the same pharmaceutical composition. In another embodiment, a composition provided herein is administered concurrently with one or more second agents in separate pharmaceutical compositions. In still another embodiment, a composition provided herein is administered prior to or subsequent to administration of a second agent. Also contemplated are administration of a composition provided herein and a second agent by the same or different routes of administration, e.g., oral and parenteral. In certain embodiments, when the composition provided herein is administered concurrently with a second agent that potentially produces adverse side effects including, but not limited to, toxicity, the second active agent can advantageously be administered at a dose that: falls below the threshold that the adverse side effect is elicited.

Encompassed by the present disclosure are methods to prophylactically treat a subject prior to a stressor. In certain embodiments, the present method prevents or delays a stress-induced affective disorder or stress-induced psychopathology in a subject. In certain embodiments, stress-induced affective disorders include major depressive disorder and posttraumatic stress disorder.

Stress-Induced Affective Disorders

There are numerous disorders that are either caused by or exacerbated by stress. These include addictive disorders such as substance abuse, anorexia, bulimia, obesity, smoking addiction, and weight addiction; anxiety disorders such as agoraphobia, anxiety disorder, obsessive compulsive disorder, panic attacks, performance anxiety, phobias, and post-traumatic stress disorder; autoimmune diseases such as allergies, arthritis, fibromyalgia, fibromytosis, lupus, multiple sclerosis, rheumatoid arthritis. Sjogren's syndrome, and vitiligo; cancer such as bone cancer, brain cancer, breast cancer, cervical cancer, colon cancer, Hodgkin's disease, leukemia, liver cancer, lung cancer, lymphoma, multiple myeloma, ovarian cancer, pancreatic cancer, and prostate cancer; cardiovascular disorders such as arrhythmia, arteriosclerosis, Burger's disease, essential hypertension, fibrillation, mitral valve prolapse, palpitations, peripheral vascular disease, Raynaud's disease, stroke, tachycardia, and Wolff-Parkinson-White Syndrome; and developmental disorders such as attention deficit disorder, concentration problems, conduct disorder, dyslexia, hyperkinesis, language and speech disorders, and learning disabilities.

Anxiety Disorders

The five major types of anxiety disorders are: panic disorder, obsessive-compulsive disorder, post-traumatic stress disorder, generalized anxiety disorder and phobias (including social phobia, also called social anxiety disorder). Each anxiety disorder has its own distinct features, but they are all bound together by the common theme of excessive, irrational fear and dread. It is common for an anxiety disorder to accompany depression, eating disorders, substance abuse, or another anxiety disorder.

Panic disorder is characterized by repeated episodes of intense fear that strike often and without warning. Physical symptoms include chest pain, heart palpitations, shortness of breath, dizziness, abdominal distress, feelings of unreality, and fear of dying. Obsessive-compulsive disorder is characterized by repeated, unwanted thoughts or compulsive behaviors that seem impossible to stop or control. Generalized Anxiety Disorder is characterized by exaggerated worrisome thoughts and tension about everyday routine life events and activities, lasting at least six months. Almost always anticipating the worst even though there is little reason to expect it; accompanied by physical symptoms, such as fatigue, trembling, muscle tension, headache, or nausea. Phobias are characterized into two major types of phobias, social phobia and specific phobia. People with social phobia have an overwhelming and disabling fear of scrutiny, embarrassment, or humiliation in social situations, which leads to avoidance of many potentially pleasurable and meaningful activities. People with specific phobia experience extreme, disabling, and irrational fear of something that poses little or no actual danger; the fear leads to avoidance of objects or situations and can cause people to limit their lives unnecessarily.

Posttraumatic Stress Disorder (PTSD)

Typically, a subject suffering from PTSD was exposed to a traumatic event in which the person experienced, witnessed, or was confronted with an event or events that involved actual or threatened death or serious injury, or a threat to the physical integrity of self or others and the person's response involved intense fear, helplessness, or horror.

Having repeated intrusive memories of the trauma exposure is one of the core symptoms of PTSD. Patients with PTSD are known to display impairments in learning and memory during neuropsychological testing. Other core symptoms of PTSD include heightened stress sensitivity (startle), tension and anxiety, memory disturbances, and dissociation.

In certain embodiments, the present method prevents or inhibits the development of post-traumatic stress disorder (PTSD) in a subject. In certain embodiments, the present method prevents or inhibits the development of one or more PTSD-like symptoms. In certain embodiments, a subject may be administered the present agent or composition prior to a situation in which the subject (such as an early responder or military personnel) is likely to be exposed to traumatic stress, immediately after exposure to traumatic stress, and/or when the subject feels that his or her PTSD symptoms are likely to appear.

Typically, the traumatic event is persistently re-experienced in one or more of the following ways: recurrent and intrusive distressing recollections of the event, including images, thoughts, or perceptions, recurrent distressing dreams of the event, acting or feeling as if the traumatic event were recurring (includes a sense of reliving the experience, illusions, hallucinations, and dissociative flashback episodes, including those that occur on awakening or when intoxicated), intense psychological distress at exposure to internal or external cues that symbolize or resemble an aspect of the traumatic event, physiological reactivity on exposure to internal or external cues that symbolize or resemble an aspect of the traumatic event. An individual suffering from PTSD also has persistent avoidance of stimuli associated with the trauma and numbing of general responsiveness (not present before the trauma), as indicated by 3 or more of the following: efforts to avoid thoughts, feelings, or conversations associated with the trauma, efforts to avoid activities, places, or people that arouse recollections of the trauma, inability to recall art important aspect of the trauma, significantly diminished interest or participation in significant activities, feeling of detachment or estrangement from others, restricted range of affect (e.g., unable to have loving feelings), sense of a foreshortened future (e.g., does not expect to have a career, marriage, children, or a normal life span), persistent symptoms of increased arousal (not present before the trauma), as indicated by 2 or more of the following: difficulty falling or staying asleep, irritability or outbursts of anger, difficulty concentrating, hypervigilance, exaggerated startle response. The disturbance, which has lasted for at least a month, causes clinically significant distress or impairment in social, occupational, or other important areas of functioning.

In certain embodiments, the present compound or composition prevents, reduces, eliminates or delays one or more of the symptoms including, but not limited to, re-experiencing of the traumatic experience in the form of intrusive memories, nightmares, flashbacks; emotional and physical reactions triggered by reminders of the trauma; distancing from others; decreased interest in activities and other people: numbing of feelings; avoidance of trauma reminders; hyperarousal symptoms, including disrupted sleep, irritability, hypervigilance, decreased concentration; increased startle reflex; and combinations thereof.

Whatever the source of the problem, some people with PTSD repeatedly relive the trauma in the form of nightmares and disturbing recollections during the day. They may also experience other sleep problems, feel detached or numb, or be easily startled. They may lose interest in things they used to enjoy and have trouble feeling affectionate. They may feel irritable, more aggressive than before, or even violent. Things that remind them of the trauma may be very distressing, which could lead them to avoid certain places or situations that bring back those memories.

The disorder may be accompanied by depression, substance abuse, or one or more other anxiety disorders. In severe cases, the person may have trouble working or socializing.

Major Depressive Disorder

Major depressive disorder refers to a class of syndromes characterized by negative affect and repeated episodes of depression without any history of independent episodes of mood elevation and over-activity that fulfill the criteria of mania. Multiple subtypes of major depressive disorders are recognized, including these with atypical characteristics, psychotic components, etc. The age of onset and the severity, duration and frequency of the episodes of depression are all highly variable. The disorder may begin at any age. The symptoms of major depressive disorder typically develop over days to weeks. Prodromal symptoms include generalized anxiety, panic attacks, phobias or depressive symptoms and may occur during several months preceding the episode. Individual episodes also last between 3 and 12 months but recur less frequently. Most patients are asymptomatic between episodes, but a minority of patients may develop a persistent depression, mainly in old age. Individual episodes of any severity are often precipitated by stressful life events. Common symptoms of a depressive episode include reduced concentration and attention; reduced self-esteem and self-confidence; ideas of guilt and unworthiness, ideas or acts of self-harm or suicide; disturbed sleep; and diminished appetite. In certain embodiments, a major depressive episode follows a psychosocial stressor, e.g., death of a loved one, marital separation, childbirth or the end of an important relationship.

The lowered mood varies little from day to day and is often unresponsive to circumstances, yet may show a characteristic diurnal variation as the day goes on. As with manic episodes, the clinical presentation shows marked individual variations, and atypical presentations are particularly common in adolescence. In some cases, anxiety, distress, and motor agitation may be more prominent at times that the depression, and the mood change may also be masked by added features such as irritability, excessive consumption of alcohol, histrionic behavior, and exacerbation of pre-existing phobic or obsessional symptoms, or by hypochondria.

Psychiatric Evaluations

In certain embodiments, the effects or efficacy of treatment with the present agent/composition are evaluated by the subject and/or a medical professional, e.g., the subject's physician. In certain embodiments, the evaluation is conducted within about 10 minutes, within about 15 minutes, within about 20 minutes, within about 5 minutes, within about 0.5 hours, within about 1 hour, within about 2 hours, within about 2.5 hours, within about 3 hours, within about 3.5 hours, within about 4 hours, within about 4.5 hours, within about 5 hours, within about 5.5 hours, within about 6 hours, within about 6.5 hours, within about 7 hours, within about 7.5 hours, within about 8 hours, within about 8.5 hours, within about 9 hours, within about 9.5 hours, within about 10 hours, within about 10.5 hours, within about 11 hours, within about 11.5 hours, within about 12 hours, within about 18 hours, within about 1 day, within about 2 days, within about 3 days, within about 4 days, within about 5 days, within about 6 days, within about 1 week, within about 2 weeks, within about 3 weeks, within about 4 weeks, within about 1 month, within about 2 months, within about 3 months, within about 4 months, within about 5 months, within about 6 months, within about 1 year, within about 2 years, or longer, following a stressor and/or administration of the present agent/composition.

Psychiatric evaluations of a patient being treated with the present method can be conducted to determine whether the method is effective. In certain embodiments, the psychiatric evaluation may be carried out before treatment, at the time of treatment, during treatment, and/or after treatment. When the psychiatric evaluation is carried out both before treatment and after (and/or during) treatment with the present method, the results of the evaluation before treatment can provide a baseline for comparison to the results of the evaluation during and/or after treatment. In certain embodiments, psychiatric evaluation is conducted only after treatment.

Psychophysiological stress tests can be performed to measure the amount of stress-induced anxiety present in the various systems of the body (i.e. muscular, cardiovascular, digestive, respiratory and neurological systems). These stress tests are routinely used in the art. Test results are compared to both local and national norms, to determine if the individual is exhibiting an excessive amount of physiological anxiety and whether or not they are able to recover from a standardized stressful stimuli in an appropriate length of time.

Psychiatric testing can be used to monitor a subject to determine the emotional and/or social etiology of the stress disorder. These tests are known in the art and include health-related assessments, mental health assessments, personality tests, and personality type assessment.

In certain embodiments, clinician-administered evaluation and/or self-report instruments are used, with the aim of measuring baseline symptomatology as well as drug actions on (1) the overall severity of the disorder, (2) the core symptoms, and (3) depressed mood.

Non-limiting examples of psychiatric evaluation tools and questionnaires include the following measures.

The Diagnostic and Statistical Manual of Mental Disorders (DSM-5) includes the revised diagnostic criteria for PTSD. See, American Psychiatric Association: Diagnostic and Statistical Manual of Mental Disorders, Fifth Edition. Arlington, Va., American Psychiatric Association, 2013. See also ptsd.va.gov/professional/PTSD-verview/dsm5_criteria_ptsd.asp.

The Structured Clinical interview for DSM-IV Axis I Disorders, Patient Edition (SCID-P) is a semi-structured interview that provides probe questions as well as follow-up questions to be asked by the clinician to assist in diagnosis. First et al., Structured Clinical interview for DSM-IV TR Axis I Disorders, Research Version, Patient Edition (SCID-I/P). New York: New York State Psychiatric Institute, Biometrics Research; 2001, it includes an overview to obtain information about demographics, work, chief complaint, history of present illness, past history, treatment history, and current functioning. The main body of SCID-P includes 9 modules that are designed to diagnose 51 mental illnesses in all.

The SCID-P for DSM-5 is the SCID-Patient version, and is the next edition of the SCID modified to incorporate the new DSM-5 criteria.

The Clinician-Administered PTSD Scale (CAPS) is a structured clinical interview designed to assess the essential features of PTSD as defined by the DSM-IV. Weathers et al., Clinician-administered PTSD scale: a review of the first ten years of research. Depress Anxiety. 2001; 13(3):132-156. The CAPS can be used to provide categorical ratings of diagnostic status as well as a quantitative index of symptom severity. Both frequency and intensity scores are derived for each individual symptom. The CAPS total score is based on an individual's response to the 17 items that assess the frequency and intensity of current PTSD symptoms. Subscales of the CAPS are utilized to assess specific symptom clusters. The total score can range from 0 to 136.

The Clinician-Administered PTSD Scale for DSM-5 (CAPS-5) is a 30-item structured interview that can be used to make current (past month) diagnosis of PTSD, make lifetime diagnosis of PTSD, and to assess PTSD symptoms over the past week. CAPS-5 is a 30-item questionnaire, corresponding to the DSM-5 diagnosis for PTSD. The language of the CAPS-5 reflects both changes to existing symptoms and the addition of new symptoms in DSM-5. Weathers, F. W., et al (2013). The Clinician-Administered PTSD Scale for DSM-5 (CAPS-5).

The Treatment Outcome PTSD Scale (TOP-8) is a brief interviewer-administered scale designed specifically for the assessment of commonly occurring signs and symptoms of PTSD that are subject to change in response to treatment (Davidson, J. R., & Collet, J. T. (1997). The eight-item treatment-outcome post-traumatic stress disorder scale: A brief measure to assess treatment outcome in post-traumatic stress disorder. International Clinical Psychopharmacology, 12(1), 41-45). The TOP-8 is comprised of eight items, each measured on a scale of 0-4, with defined anchors given for each item. The items are representative of the three core features of PTSD with a maximum possible score of 32.

The Hamilton Psychiatric Rating Scale for Anxiety (HAM-A) is a widely used observational rating measure of anxiety severity. The scale consists of 14 items. Each item is rated on a scale of 0 to 4. This scale is administered to assess the severity of anxiety and its improvement during the course of treatment. The HAM-A total score is the sum of the 14 items and the score ranges from 0 to 56. Hamilton M. The Assessment of Anxiety-States by Rating. Br J Med Psychol. 1959; 32(1):50-55.

The Montgomery-Asberg Depression Rating Scale (MADRS) is a 10-item instrument used for the evaluation of depressive symptoms in adults and for the assessment of any changes to those symptoms. Montgomery S. A., et al., A new depression scale designed to be sensitive to change. Br J Psychiatry. 1979 April; 134:382-389. Each of the 10 items is rated on a scale of 0 to 6, with differing descriptors for each item. These individual item scores are added together to form a total score, which can range between 0 and 60 points.

The Young Mania Rating Scale, item 1 (YMRS-1) used to assess mood elevation on the infusion days. Young R C, et al. Rating-Scale for Mania—Reliability, Validity and Sensitivity. Br J Psychiatry. 1978; 133(NOV):429-435.

The Brief Psychiatric Rating Scale (BPRS) is used to assess acute behavioral changes during the infusions. Overall J E et al., The Brief Psychiatric Rating-Scale. Psychol. Rep. 1962; 10(3):799-812 Four key BPRS items for the positive (+) symptoms of psychosis are used: conceptual disorganization, hallucinatory behavior, suspiciousness, and unusual thought content. Three items representing the negative (−) symptoms of psychosis will also be used: blunted affect, emotional withdrawal, and motor retardation.

The Clinician-Administered Dissociative States Scale (CADSS) is used to measure dissociative effects during the infusions. Bremner J D, et al., Measurement of Dissociative States with the Clinician-Administered Dissociative States Scale (CADSS). J Trauma. Stress. 1998; 11(1):125-136 The scale includes 19 questions and 8 observer ratings scored from 0 (not at all) to 4 (extremely). The CADSS measures impairment in body perception, environmental perception, time perception, memory impairment, and feelings of unreality.

The Patient Rating Inventory of Side Effects (PRISE) is a patient self-report used to qualify side effects by identifying and evaluating the tolerability of each symptom. Levine J, Schooler N R. SAFTEE: A technique for the systematic assessment of side effects in clinical trials. Psychopharmacol Bull. 1986; 22(2)343-381.

The Clinical Global Impression (CGI) scale assesses treatment response in psychiatric patients. The administration time is 2 minutes. This scale consists of three items: Severity of Illness (item 1); Global Improvement (item 2); and Efficacy Index (item 3). Item 1 is rated on a seven-point scale (1=normal, 7=among the most extremely ill patients) as is item 2 (1=very much improved, 7=very much worse). Each includes an additional response of "not assessed." Item 3 is rated on a four-point scale (from "none" to "outweighs therapeutic effect").

The Impact of Events Scale (IES) is one of the most widely used self-report measures of stress reactions to traumatic events. Horowitz et al., impact of Event Scale: a measure of subjective stress. Psychosom Med. 1979 May;

41(3):20)9-218. See also, Weiss et al., The Impact of Event Scale—Revised In: Wilson 3, Keane T M. eds. Assessing psychological trauma and PTSD. New York: Guilford; 1996: 399-411. It measures both intrusion and avoidance. Sundin et al., Impact of Event Scale: psychometric properties. Br J Psychiatry. 2002 March; 180:205-209. Joseph S. Psychometric evaluation of Horowitz's Impact of Event Scale: a review. J Trauma Stress. 2000 January; 13(1): 101-113. The total score can range from 0 to 75.

The Posttraumatic Stress Disorder Checklist (PCL-5) is a 17-item self-report measure reflecting DSM-5 symptoms of PTSD. The PCL-5 measures symptoms in response to stressful situations (Weathers, F., et al. (1993). The PTSD checklist (PCL): Reliability, validity, and diagnostic utility. Annual Convention of the International Society for Traumatic Stress Studies, San Antonio, Tex.).

The Quick Inventory of Depressive Symptomatology, Self Report (QIDS-SR) is a 16-item self-rated instrument designed to assess the severity of depressive symptoms present in the past seven days. Rush A J, Trivedi M H. Ibrahim H M et al. The 16-Item quick inventory of depressive symptomatology (QIDS), clinician rating (QIDS-C), and self-report (QIDS-SR): a psychometric evaluation in patients with chronic major depression. Biol. Psychiatry. 2003; 54(5):573-583. The 16 items cover the nine symptom domains of major depression, and are rated on a scale of 0-3. Total score ranges from 0 to 27, with ranges of 0-5 (normal), 6-10 (mild), 11-15 (moderate), 16-20 (moderate to severe), and 21+ (severe).

The Childhood Trauma Questionnaire (CTQ) is a 28-item self-report instrument that assesses childhood trauma in the following areas: physical, sexual and emotional abuse and physical and emotional neglect. Bernstein D P, Stein J A, Newcomb M D et al. Development and validation of a brief screening version of the Childhood Trauma Questionnaire. Child Abuse Negl. 2003 February; 27(2);169-190. Each item is rated on a scale of 1 (never true) to 5 (very often true). The 5 subscales are then totaled, with scores ranging from 5-25 for each traumatic category.

Visual Analogue Scales (VAS) are used to assess subjective state changes. Bond A, Lader M. The use of analogue scales in rating subjective feelings. Br I Med Psychol. 1974; 47(3):211-2.18. They are 100-mm horizontal lines marked proportionately to the perceived intensity of the subjective experience (0=not at all, to 10=extremely) for the following states; anxious, depressed, drowsy, high, hungry, and nauseous.

The Sheehan Disability Scale (SDS) is a self-report disability measure. It has demonstrated sensitivity to impairment and changes as a result of treatment across a wide range of psychiatric disorders. The SDS asks only about current levels of impairment, providing no indication of whether the person has done better or worse in the past, thus making it a reasonable short-term outcome measure that is un-confounded by historical impressions. The dependent variable is the total score, which is based on the sum of three 10-point items (work, social life, and family life), with higher scores reflecting greater disability. Sheehan D. The Anxiety Disease. New York, N.Y.: Scribner; 1983.

The Wechsler Abbreviated Scale of Intelligence 2-Subtest (WASI-2) is a reliable brief measure of IQ for 6 to 89 year-olds that includes Vocabulary (an estimate of verbal fluid abilities) and Matrix Reasoning (an estimate of non-verbal fluid abilities). Wechsler D. Wechsler Abbreviated Scale of Intelligence San Antonio, Tex.: Psychological Corporation; 1999. It is extensively used in clinical, educational, and research settings. Average reliability coefficient is 0.96 and test-retest reliability is 0.88.

The Hopkins Verbal Learning Test (HVLT) is a repeatable test of memory acquisition and delayed recall of words. Subjects are presented with the same 12-item list for 3 learning trials and asked each time to repeat the items on each list. Delayed recall and recognition conditions are administered later. Dependent variables used in this study include total learning over the 3 trials (for the acquisition variable) and total delayed recall score (for the recall component). Brandt J. Benedict R. Hopkins Verbal Learning Test, Revised. Odessa, Fla.: Psychological Assessment Resources; 1997.

The Profile of Mood States-Bipolar (POMS-Bi) scale measures moods and feelings primarily in clinical rather than nonclinical settings. It can help to determine an individual's psychiatric status for therapy, or be used to compare mood profiles associated with various personality disorders. It is also a useful instrument in identifying the effects of drug treatments.

The Post-Traumatic Cognitions Inventory (PTCI) is a 33-item scale, which is rated on a Liken-type scale ranging from 1 (totally disagree) to 7 (totally agree). Scale scores are formed for the three subscales, which show a high degree of intercorrelation (rs=0.57-0.75).

The New Cognitions scale is a 6-item pilot scale, which is rated on a Likert-type scale ranging from 1 (not at all) to 4 (a lot). The scale is based on the Post Traumatic Growth Inventory (PTGI) from which items have been directly selected (new items were added to the scale as well), and on the Brief-COPE (see Carver, C. S. (1997) "You want to measure coping hut your protocol's too long: Consider the brief COPE." International Journal of Behavioral Medicine 4; 92-100).

The Medical Outcomes Study (MOS) Social Support Survey is a 19-item self-report measure designed to assess levels of functional social support. The MOS-SS has two subscales (emotional and instrumental social support) to identify potential social support deficits (Sherbourne, C. D. & Stewart, A. L. (1991). "The MOS Social Support Survey." Soc Sci Med 32(6): 705-714).

The Purpose in Life test-Short Form (PIL-SF) is a brief, 4-item form of the 20-item Purpose in Life test. This scale asks respondents to report to what extent they have achieved their goals in life, and to what extent they perceive their life to be meaningful or purposeful. (Schulenberg et al 2010; Psychotherapy (Chic). 2008 December; 45(4):447-63).

Posttraumatic Growth Inventory (PTCI)-Short Version is a 10-item shortened version of the PTCI self-report questionnaire (ref). It asks respondents to rate the extent to which they have changed as the result of experiencing a highly stressful life event. Items span positive changes in five domains: relating to others, new possibilities, personal strength, spiritual change, and appreciation of life (Cann, A., et al. (2010). A short form of the Posttraumatic Growth Inventory. Anxiety, Stress & Coping, 23, 127-137).

The Quality of Life Enjoyment and Satisfaction Questionnaire (Q-LES-Q) is a self-report scale measuring the degree of enjoyment and satisfaction experienced by subjects in various areas of daily functioning. The summary scores are reliable and valid measures of these dimensions in a group of depressed subjects (Endicott J, et al. Quality of Life Enjoyment and Satisfaction Questionnaire: A New Measure. Psychopharmacology Bulletin; 1993; 29:321-326).

In certain embodiments, self-evaluation of the subject being treated is conducted.

Pharmaceutical Compositions

While it is possible that the present a compound, as well as salts, solvates and physiological functional derivatives thereof, may be administered as the raw chemical, it is possible to present the active ingredient as a pharmaceutical composition. Accordingly, the invention further provides a pharmaceutical composition, which comprises the present compound and/or salts, solvates and physiological functional derivatives thereof, and one or more pharmaceutically acceptable carriers, diluents, or excipients. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing the present compound, or salts, solvates and physiological functional derivatives thereof, with one or more pharmaceutically acceptable carriers, diluents or excipients.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing compound 20, and pharmaceutically acceptable excipients.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopeias for use in animals, and more particularly in humans.

Pharmaceutical compositions of the present invention may be presented in unit dose forms containing a predetermined amount of active ingredient per unit dose. Such a unit may contain, for example, 5 μg to 1 g, preferably 1 mg to 700 mg, more preferably 5 mg to 100 mg of the present compound, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), inhaled, nasal, ocular, or parenteral (including intravenous and intramuscular) route. The present composition may be injected. Such compositions may be prepared by any method known in the art of pharmacy, for example by bringing into association the active ingredient with the carrier(s) or excipient(s).

In a further embodiment, the present invention provides a pharmaceutical composition adapted for administration by the oral route, the treatment of stress-induced affective disorder.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

It should be understood that, in addition to the ingredients particularly mentioned above, the compositions may include other agents conventional in the art having regard to the type of formulation in question, for example those suitable for oral administration may include flavoring agents.

A therapeutically effective amount of a compound of the present invention will depend upon a number of factors including, for example, the age and weight of the subject, the precise condition requiring treatment and its severity, the nature of the formulation, and the route of administration, and will ultimately be at the discretion of the attendant physician or veterinarian.

Kits

Also provided are kits for use in the present methods of prophylactically treating a stress-induced affective disorder.

The kits can include a compound or composition provided herein, and instructions providing information to a health care provider regarding usage in accordance with the present methods. The kit may optionally contain a second agent or composition. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition. In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like.

The kits described herein contain one or more containers, which contain compounds, signaling entities, biomolecules and/or particles as described. The kits also contain instructions for mixing, diluting, and/or administrating the compounds. The kits also include other containers with one or more solvents, surfactants, preservative and/or diluents (e.g., saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are used, the liquid form may be concentrated or ready to use. The solvent will depend on the compound and the mode of use or administration. Suitable solvents for drug compositions are well known and are available in the literature. The solvent will depend on the compound and the mode of use or administration.

The kits comprise a carrier being compartmentalized to receive in close confinement one or more container such as vials, tubes, and the like, each of the container comprising one of the separate elements to be used in the method. For example, one of the container may comprise a positive control in an assay. Additionally, the kit may include containers for other components, for example, buffers useful in the assay.

This invention will be better understood from the Examples, which follow. Howe e one skilled in the art will readily appreciate that the specific methods and results discussed are merely illustrative of the invention as described more fully in the claims that follow thereafter.

EXAMPLES

Example 1

Ketamine as a Prophylactic Against Stress-Induced Depressive-Like Behavior

Stress exposure is one of the greatest risk factors for psychiatric illnesses like major depressive disorder and posttraumatic stress disorder. However, not all individuals exposed to stress develop affective disorders. Stress resilience, the ability to experience stress without developing persistent psychopathology, varies from individual to individual. Enhancing stress resilience in at-risk populations could potentially protect against stress-induced psychiatric disorders. Despite this fact, no resilience-enhancing pharmaceuticals have been identified.

Using a chronic social defeat (SD) stress model, learned helplessness (LH), and a chronic corticosterone (CORT) model in mice, we tested if ketamine could protect against depressive-like behavior. Mice were administered a single dose of saline or ketamine and then 1 week later were subjected to 2 weeks of SD, LH training, or 3 weeks of CORT.

SD robustly and reliably induced depressive-like behavior in control mice. Mice treated with prophylactic ketamine were protected against the deleterious effects of SD in the forced swim test and in the dominant interaction test. We confirmed these effects in LH and the CORT model. In the LH model, latency to escape was increased following training, and this effect was prevented by ketamine. In the CORT model, a single dose of ketamine blocked stress-induced behavior in the forced swim test, novelty suppressed feeding paradigm, and the sucrose splash test.

These data show that ketamine can induce persistent stress resilience and, therefore, may be useful in protecting against stress-induced disorders.

We first utilized social defeat (SD) to examine whether ketamine could increase stress resilience and, thereby protect against de novo induction of psychopathology. We hypothesized that ketamine would confer stress resiliency to mice if administered before stress. We chose to perform SD in 129S6/SvEvTac mice, which robustly and reliably develop a depressive-like phenotype following SD (26). Mice were administered either saline or a single subanesthetic injection of ketamine and 1 week later, SD was administered to half of the mice. We found that a single injection of ketamine induced robust stress resilience that persisted for at least 3 weeks post-injection. Moreover, we confirmed our effects in two additional models in which depressive/anxious behavior is induced by chronic elevation of glucocorticoids in C57BL/6NTac mice (27) or by repeated, unescapable shocks (learned helplessness [LH]) (28-30). Again, a single subanesthetic dose of ketamine, administered 4 weeks before behavioral assessment, decreased immobility in the forced swim test (FST) and protected against depressive-like behavior in the novelty suppressed feeding (NSF) paradigm and the sucrose splash test (ST). In the LH model, the latency to escape a shock increases with LH training and this effect was prevented by prophylactic ketamine. These findings demonstrate that the protective effect of ketamine extends at least 4 weeks post-injection. To our knowledge, this is the first study to examine the potential of psychopharmaceuticals to provide long-term prophylactic protection against the induction of stress-related disorders.

Ketamine Metabolite Administration is Also Prophylactic

Prophylactic metabolites of ketamine administration decrease behavioral despair. FIG. 15A shows the experimental design. FIG. 15B is a graph showing that prophylactic K-injected mice expressed significantly less immobility in day 2 of the FST when compared with Sal-injected mice. Moreover, prophylactic metabolites of ketamine are efficacious as prophylactics at 10 and 30 mg/kg. $*p<0.05$, $p<0.01$, $*p<0.001$.

Methods and Materials

Mice

Male 129S6/SvEvTac mice were purchased from Taconic (Hudson, N.Y.), CD-1 mice were purchased from Charles River Laboratories (Wilmington, Mass.) at 8 to 10 weeks of age and housed individually until the start of SD. The procedures described herein were conducted in accordance with the National Institutes of Health regulations and approved by the Institutional Animal Care and Use Committees of Columbia University and the New York State Psychiatric Institute.

Male C57BL/6NTac mice were purchased from Taconic Farms (Lille Skensved, Denmark) at 8 weeks of age and were housed five per cage before the start of corticosterone. (CORT) treatment. All testing was conducted in compliance with the laboratory animal care guidelines and with protocols approved by the Institutional Animal Care and Use Committee. All mice were housed in a 12-hour (600-1.800) light-dark colony room at 221C. Food and water were provided ad libitum. Behavioral testing was performed during the light phase.

Drugs

Experiment 1 (Pre-ketamine in social defeat (SD)): At 8 weeks of age, a single injection of saline (0.9% NaCl) or ketamine (K) (10, 30, or 90 mg $kg^{-1}$) (Ketaset III, Ketamine HCl, Fort Dodge Animal Health, Forth Dodge, Iowa) was administered. Ketamine was prepared in physiological saline and all injections were administered intraperitoneally (i.p.) in volumes of 0.1 cc per 10 mg body weight. A dose of 30 mg $kg^{-1}$ of ketamine was chosen for the 129S6/SvEv experiments, as pilot studies indicated that this dose did not affect immobility 2 h after administration. At 9 weeks of age, 1 week following this injection, SD was started.

Experiment 2 (Post-ketamine in SD): At 9 weeks of age. SD was administered for 2 weeks.

24 h after the last bout of SD, a single injection of saline or ketamine (30 mg $kg^{-1}$) was administered (mice were 11 weeks old). The forced swim test (PST) was administered 2 h following the injection.

Experiment 3 (Pre-fluoxetine in SD): At 6 weeks of age, fluoxetine hydrochloride (Flx) (BioTrend Chemicals AG, B6197) was administered in the drinking water (18 mg $kg^{-1}$/day) for 3 weeks before the start of SD. Starting at 9 weeks of age, SD was then administered for 2 weeks without vehicle or Flx in the drinking water.

Experiment 4 (Pre-ketamine in learned helplessness (LH)); At 8 weeks of age, a single injection of saline or ketamine (30 mg $kg^{-1}$) was administered. One week following this injection, LH training (inescapable shock) was administered. Two weeks later, mice were administered LH testing (shock escape).

Experiment 5 (Pre-ketamine and pre-fluoxetine corticosterone (CORT)): C57BL16NTac mice were injected with ketamine (10, 30, 90 mg $kg^{-1}$, i.p.) 1 week before the start of CORT, or administered fluoxetine (18 mg $kg^{-1}$ per day) in the drinking water for 3 weeks before the start of CORT. Ketamine was purchased from Merial (100 mg/ml stock solution). Fluoxetine hydrochloride (160 µg/mL, equivalent to 18 mg $kg^{-1}$ per day in the drinking water) was purchased from Anawa Trading (Zurich, Switzerland) and dissolved in 0.45% hydroxypropyl-β-cyclodextrin (β-CD) (Sigma-Aldrich, Saint-Quentin Fallavier, France) solution. Following ketamine or fluoxetine treatment, CORT was administered for 3 weeks in the drinking water. CORT (4-pregnen-11b-DIOL-3 20-DIONE 21-hemisuccinate) (35 µg/ml) from. Sigma Aldrich (Saint-Quentin Fallavier, France) was dissolved in vehicle (0.45% β-CD). Control animals received vehicle (0.45% β-CD) throughout the duration of the experiment.

Experiment 6 (Post-ketamine and post-fluoxetine in CORT); In C57BL/6NTac mice. vehicle or CORT was administered for 4 weeks in the drinking water. While administration with 0.45% β-CD or CORT continued, mice were injected with saline or ketamine (10 mg $kg^{-1}$), or were administered vehicle or chronic fluoxetine (18 mg $kg^{-1}$ per day in the drinking water).

Social Defeat

Adult aggressor CD-1 male mice were single-housed in Macrolon® polycarbonate resin cages (15.25 in×7.8 in×9.5 in) (Animal Care Systems, Inc., Centennial, Colo.). Male 129S6/SvEvTac mice (9 weeks of age) were subsequently placed into the resident. CD-1 mouse's cage. Three antagonistic encounters were allowed between the CD-1 mouse and the intruder. Each of these encounters typically lasted less than 5 min. Following the encounters, mice were separated by a polished stainless steel cage divider (Animal Care Systems, Inc., Centennial, Colo., P/N C79171), which allowed for olfactory and auditory communication, but limited visual or tactile contact. The partition was removed daily for 2 weeks and 3 antagonistic encounters were allowed between the mice each day. This procedure consistently yielded a submissive phenotype in the experimental intruder mice. Control (Ctrl) mice were group housed 4 to 5 per cage in Macrolon® polycarbonate resin cages without dividers.

Corticosterone Model

The hypothalamic-pituitary-adrenal (HPA) axis is often dysregulated in clinical depression. In this model, glucocorticoid levels are exogenously increased. This chronic CORT elevation results in dysregulation of the HPA axis. For example, there is a blunting of the HPA axis response to stress in CORT-treated mice, as shown by marked attenuation of stress-induced CORT levels (A1, A2). This model reliably induces anxious and depressive-like behavior in mice.

The dose and duration of CORT treatment was selected based on previous studies (A1, A2, A3). CORT (35 µg/ml, equivalent to approximately 5 mg/kg/d) or vehicle (0.45% 3-CD) was available ad libitum in the drinking water in opaque bottles to protect it from light. CORT-treated water was changed every 3 days to prevent any possible degradation.

Learned Helplessness

The LH paradigm was used to induce depressive-like behavior (A4). In this paradigm, mice are exposed to unpredictable and uncontrollable stress (shocks) and then develop coping deficits to deal with the inescapable shocks. We modified a previously published paradigm (A5). Briefly, the procedure was conducted in a two-chamber shuttle box (model ENV 010MD; Med Associates, St. Albans, Vt.) located within a sound-attenuated cubicle. The grid floor was made of stainless steel and connected to a shock generator. The scrambled shock generator (model ENV 414S, Med Associates) created varying electrical potential differences between bars preventing an animal from avoiding shock.

Inescapable shock (training): At approximately 9 weeks of age, mice were trained in the LH paradigm. For each shuttle box, 2 animals were administered the protocol at the same time: the central door was closed, with one animal in the chamber on each side. After a 3 min habituation period, the shock deliveries began. The training protocol consisted of 70 shocks, each with a 3 s average duration, at 0.5 mA, and with an inter-trial interval (ITI) of approximately 15 s. This protocol was the same as the "Med Protocol" published by Muller et al. (2011) (AS), with the exception of the intensity (0.5 mA versus 0.6 mA).

Shock escape (testing): Mice were tested in the same shuttle box used in the inescapable shock training. The box consisted of two identical chambers (17 L×20 W×17 H), separated by an automated door that opened vertically. The shuttle box was equipped with 8 infrared beams (4 on each side) for detecting position and activity of the animal (Med Associates, St. Albans, Vt.). Each mouse was placed into the right chamber with the door raised and was allowed to freely explore both chambers for 3 min. Then the door closed automatically.

At the beginning of each trial, the door was raised and 5 s later a foot shock (0.5 mA) was delivered. The subject's exit from the shocked side ended the trial. If the mouse did not exit after 15 s, the shock was turned off and the trial ended. The door was lowered at the end of the trial. A session consisted of 30 trials, each separated by a 30 s ITI. Escape latencies were computed as the time from Shock onset to the end of trial, if the subject failed to make a transition the maximum 15 s was used for the escape latency score.

Forced Swim Test

The FST is typically used in rodents to screen for potential human antidepressants (A6-A7). In fact, many papers examining ketamine in mouse models only observe effects in the FST (A8-A10). In the FST, time spent immobile, as opposed to swimming, is used as a measure of depressive behavior.

The FST was administered as previously described (A11). Briefly, mice were placed into clear plastic buckets 20 cm in diameter and 23 cm deep filled ⅔ of the way with 22° C. water. Mice were videotaped, from the side for 6 min and were exposed to the swim test on 2 consecutive days. For the SI) experiments, scoring was performed using an automated Viewpoint Videotrack software package (http://www.viewpoint.fr/en/a/anxiety-and-depression). For the CORT experiments, automated scoring was done using the automated X'PERT EST software suite (Bioseb, Vitrolles, France). The dependent variable was immobility.

Tail Suspension Test (TST)

The TST was administered as previously described (A2). Briefly, animals were suspended for 6 min and immobility during this period was assessed using an automated TST apparatus (Bioseb, Vitrolles, France). A specific strain gauge linked to a computer quantifies the time spent by each mouse trying to escape.

Dominant Interaction

Dominant interaction was performed as previously described (A12). Briefly, mice were placed into a large open field containing 2 upside-down wire mesh pencil cups. One pencil cup served as a novel object or empty container. The other pencil cup contained the CD-1 aggressor mouse. Mice were placed in the middle of the open field arena and allowed to explore for 10 min. Sessions were videotaped and the first 5 min were later analyzed using behavioral tracking software (TopScan, CleverSys, Reston, Va.).

Social Interaction

Mice were placed into a large open field containing 2 upside-down wire mesh pencil cups. One pencil cup served as a novel object or empty container. The other pencil cup contained a novel 129S6/SvEv male mouse. Mice were placed in the middle of the open field arena and allowed to explore for 10 min. Sessions were videotaped and the first 5 min were later analyzed using behavioral tracking software (TopScan, CleverSys, Reston, Va.).

Novelty Suppressed Feeding (NSF)

Testing was performed as previously described (A13). Briefly, the testing apparatus consisted of a plastic box (50×50×20 cm). The floor was covered with approximately 2 cm of wooden bedding and the arena was brightly lit (1100-1200 lux). For 129S6/SvEv experiments, mice were food restricted for 12 h. For the C57BL/6N experiments, mice were food restricted for 24 h. All food was removed from the home cage. At the time of testing, a single pellet of food (regular chow) was placed on a white paper platform positioned in the center of the box. Each animal was placed in a corner of the box, and a stopwatch was immediately started. The latency of the mice to begin eating was recorded. Immediately after the latency was recorded, the food pellet was removed from the arena. The mice were then placed into a cage and the amount of food consumed in 5 min was measured (home cage consumption), followed by an assessment of post-restriction weight. We used the Kaplan-Meier survival analysis due to the lack of normal distribution of data. The Mantel-Cox log-rank test was used to evaluate differences between the experimental groups.

Elevated Plus Maze (EPM)

Testing was performed as previously described (A14). Briefly, the maze is a plus-cross-shaped apparatus consisting of four arms, two open and two enclosed by walls, linked by a central platform at a height of 50 cm from the floor. Mice were individually placed in the center of the maze facing an open arm and were allowed to explore the maze for 5 min. The time spent in and the number of entries into the open arms was used as an anxiety index. For the 12956/SvEv experiments, videos were scored using behavioral tracking software (TopScan, CleverSys, Reston, Va.). For the C57BL/6Ntac experiments, all parameters were measured using a videotracker (EPM3C. Bioseb, Vitrolles, France).

Contextual Fear Conditioning (CFC)

The 1-shock CFC procedure was performed as previously published (A15). Briefly, mice were placed into context A and administered a 2-s shock (0.75 mA) 180 s later. Mice were removed from the context 15 s following the termination of shock (at 197 s). For context retrieval, mice were placed back into context A for 180 s. For alternate contexts, mice were placed into the contexts for 180 s.

Splash Test

This test consisted of squirting 200 µl of a 10% sucrose solution on the mouse's snout. The grooming duration was quantified using Stopwatch+ (Center for Behavioral Neuroscience, Georgia State University).

Open Field (OF)

The open field protocol was administered as previously described (A11), with the exception that 1 quadrant was scented with female urine. Total distance traveled in each quadrant was quantified in 1-min bins.

Methods for Assessment of the (R)- and (S)-enantiomers, metabolites, and other ketamine-like compounds.

Mice: Male and female 129S6/SvEv (Taconic) mice will be purchased from Taconic at 7 weeks of age.

Drug and compound administration: All drugs and experimental compounds will be injected at 8 weeks of age. Each group will consist of 16 mice. Mice will be scored for any abnormalities after administration in the home cage. Initial results in FIGS. 15A-B show results for (2R,6R)-HNK.

A) Saline (0.9% NaCl), (2,5,6S)-HNK (synthesized by OCCC), (2R,6R)-HNK (synthesized by OCCC), R-norketamine (AstaTech), S-norketamine (AstaTech), (S)-ketamine (Sigma), (R)-ketamine (Sigma), and (R,S)-ketamine (Ketaset. Ketamine HCl injection, Fort Dodge Animal Health, Forth Dodge, IA) will be administered in a single dose. All metabolites and enantiomers will be administered at 3, 10, 30, and 75 mg/kg of body weight.

B) Saline (0.9% NaCl), 2-fluorodeschloroketamine (synthesized by OCCC), tiletamine (Putney Veterinary), and (R,S)-ketamine (Ketaset III, Ketamine HCl injection, Fort Dodge Animal Health, Forth Dodge, Iowa) will be administered in a single dose. All drugs and compounds will be administered at between 3-30 mg/kg of body weight.

C) Saline (0.9% NaCl), Rn 25-6981 (Tocris), CP-101,606 (Sigma), GLYX-13 (Allergan), CX546 (Tocris), and (R,S)-ketamine (Ketaset III, Ketamine HCl injection, Fort Dodge Animal Health, Fort Dodge, Iowa) will be administered in a single dose. Ro 2.5-6981 will be administered at 10 mg/kg of body weight. CP-101,606 will be administered at 10, 30, or 75 mg/kg (Poleszak E, et al. (2016), Metlab Brain Dis 31:803-14. GLYX-13 will be administered at 10, 30, and 75 mg/kg of body weight. CX546 will be administered at 10 mg/kg of body weight.

Corticosterone Enzyme Immunoassay (EIA)

Mice were exposed to a minor stressor for 10 min and then returned to their home cages. Blood was collected from awake mice 70 min after the start of the stressor from the retro-orbital sinus using hematocrit tubes. Blood was then transferred to Eppendorf tubes pre-coated with 5 µl 0.5 M EDTA, placed on ice, and immediately spun down to obtain plasma for subsequent EIA. Plasma was stored at −80° C. until analysis. EIA was performed using a DetectX Corticosterone EIA Kit (#K014-H1, Arbor Assays).

Immunohistochemistry

Mice were deeply anesthetized with ketamine (100 mg kg) and transcardially perfused with IX phosphate buffer saline (PBS), followed by chilled 4% paraformaldehyde (PFA)/IX PBS (A15), Brains were post-fixed overnight in 4% PFA at 4° C., then cryoprotected in 30% sucrose/1× PBS, and stored at 4° C. Serial coronal sections (35 µm) were cut through the entire hippocampus on a cryostat and stored in IX PBS with 0.1% $NaN_3$. Doublecortin (DCX) immunohistochemistry was performed as previously described (A15). For DCX immunohistochemistry, sections were washed in 1× PBS containing 0.5% Triton and then quenched in 0.3% $H_2O_2$ in IX PBS/$CH_3OH$ (1:1) for 15 min at room temperature. Sections were blocked in 10% normal donkey serum in 1× PBS with 0.5% Triton X-100 for 2 h at room temperature. Incubation with primary antibody was performed at 4° C. overnight (goat anti-DCX, 1:500, Santa Cruz Biotechnology, Santa Cruz, Calif., #SC 8,066) in 1× PBS with 0.5% Triton X-100. Sections were then incubated with a biotinylated secondary antibody (donkey anti-goat; 1:250, Jackson ImmunoResearch, West Grove, Pa.) for 2 h at room temperature. Sections were treated with avidin-biotin-peroxidase complex (ABC Elite Kit, Vector Labs, Burlingame, Calif.) followed by 3,3' diaminobenzidine as a substrate for staining (Vector, Burlingame, Calif.).

Ki67 immunohistochemistry was performed as previously described (A16). For Ki67 immunohistochemistry, sections were washed in 1× PBS containing 0.5% Triton, and then blocked in 10% normal donkey serum in 1× PBS with 0.5% Triton X-100 for 2 h at room temperature. Incubation with primary antibody was performed at 4° C. overnight (rabbit anti-Ki67, 1:100, Vector Laboratories. Burlingame, Calif., #VP-RM04) in 1× PBS with 0.5% Triton X-100. Sections were then incubated with a biotinylated secondary antibody (donkey anti-rabbit; 1:250, Jackson ImmunoResearch, West Grove, Pa.) for 2 h at room temperature. Sections were treated with avidin-biotin-peroxidase complex (ABC Elite Kit, Vector Labs, Burlingame, Calif.) followed by 3,3' diaminobenzidine as a substrate for staining (Vector, Burlingame, Calif.).

Cell Quantification

An investigator blind to treatment used a Zeiss Axioplan-2 upright microscope (Oberkochen, Germany) to count cells bilaterally in the granule cell layer of the dentate gyrus throughout the entire rostra-caudal axis of the hippocampus (HPC). Every sixth section throughout the entire extent of the HPC was included in the analysis. Cells were counted bilaterally using a 20× objective. The average cells per section are presented throughout the text.

Statistical Analysis

Results from data analyses are expressed as means±SEM. Alpha was set to 0.05 for all analyses. Data were analyzed using Stat View 5.0 software (SAS Institute, Cary, N.C.) for the SD experiments and were analyzed using GraphPad Prism v6.0f for the CORT experiments. For all experiments, one-way or one-way ANOVAs with repeated-measures were applied to the data as appropriate. Significant main effects and/or interactions were followed by Fisher's protected least significant difference post-hoc analysis or unpaired t-tests. All main effects and interactions are noted throughout the text.

RESULTS

Figure 1B:
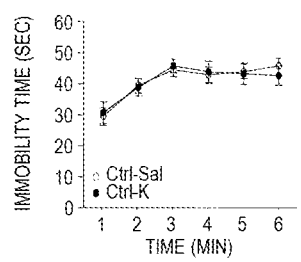
Figure 1C:
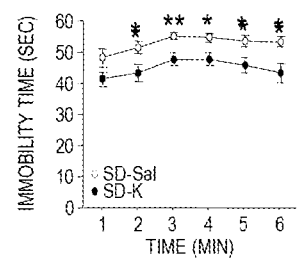
Figure 1D:
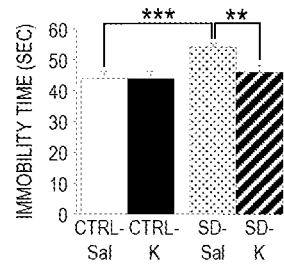

Ketamine Administration Before SD Protects Against the induction of Depressive-Like Behavior Mice were administered a single injection of saline or ketamine (30 mg $kg^{-1}$) (FIG. 1A). One week later, mice either remained group housed (Ctrl) or underwent SD. After 2 weeks of SD, mice were weighed, and behavior was assessed. Classically, immobility in the FST has been interpreted as an index of hopelessness or a negative mood (31). Rodents given acute or chronic antidepressants exhibit decreased immobility (32). Here, on day 2 of the FST, there was an overall effect of SD on immobility time. Ctrl-saline (Sal) and Ctrl-ketamine (K) mice displayed equal levels of immobility time (FIG. 1B). In SD mice. ketamine (SD-K)

significantly decreased immobility time when compared with saline (SDSal) (FIGS. 1C, 1D). These data indicate that ketamine increases resilience to behavioral despair as measured by the FST.

Figure 1E:
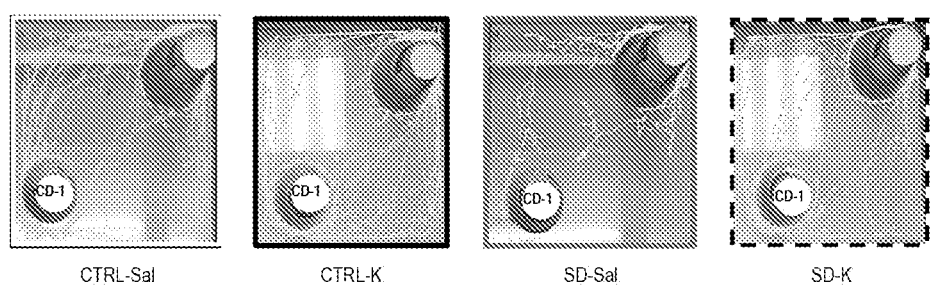
Figure 1F:
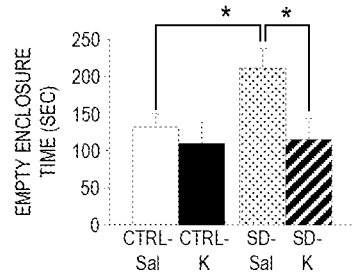
Figure 1G:
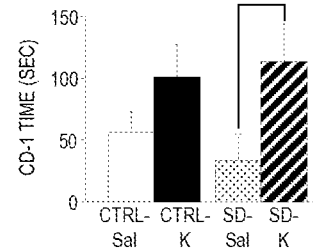

Dominant interaction is a robust way of testing the induction of depressive-like behavior by SD (10) (FIG. 1E). As expected, SD-Sal mice spent significantly more time investigating an empty enclosure quadrant than Ctrl-Sal mice (FIG. 1F). Ctrl (Sal or K) mice spent an equivalent amount of time investigating the empty enclosure quadrant. SD-K mice exhibited significantly less time investigating the empty enclosure quadrant when compared with SD-Sal mice. Similarly, SD-K mice exhibited a significantly increased willingness to interact with the CD-1 when compared with SD-Sal mice (FIG. 1G).

To determine if this exploration deficit extended to neutral environments, open field exploration was investigated in an arena scented with female urine. We did not detect any differences in the empty quadrant or the urine quadrant between Ctrl and SD mice. Furthermore, to determine if social avoidance generalized to other mice, we also assessed social interaction with a novel mouse. We did not find an effect of SD or ketamine on social interaction. In summary, these data suggest that SD decreases exploration and willingness to interact with a CD-1 aggressor and that prior ketamine administration protects against this deleterious effect of SD on social behavior.

An Injection of Ketamine Before SD Does Not Impact Anxiety-Like Behavior or Contextual Fear Memory We next examined the effects of ketamine on anxiety-like behavior and cognitive tests. In the NSF paradigm, we found no significant effect of SD or ketamine on the latency to feed. In fact, all groups showed similar latencies. This effect is confounded: despite having comparable body weights before and after SD, SD mice lost significantly more weight during the 12-hour fast preceding NSF than Ctrl mice. Possibly as a result, SD mice ate more in a home cage following NSF when compared with Ctrl mice. These findings suggest that SD significantly alters metabolism in 129S6/SvEv mice.

We observed a significant effect of SD in an anxiety-related test, the elevated plus maze (EPM). SD mice spent more time in the closed arms than Ctrl mice. However, there was no significant effect of ketamine in either group. The absence of an effect of ketamine in the EPM is consistent with previous studies (33, 34), as it remains to be established if ketamine is as robust an anxiolytic as it is an antidepressant (35).

The Ketamine-Induced Improvement is Dose-Specific

We next examined a dose titration curve of ketamine. Mice were administered 0, 10, 30, or 90 mg kg$^{-1}$ of ketamine before the start of SD. After 2 weeks of SD mice underwent the FST and CORT levels were measured following a brief stressor. We replicated our previous SD effect, as SD-Sal mice displayed significantly more immobility time in the FST when compared with Ctrl-Sal (FIG. 2A). However, SD-Sal and SD-K (10 mg kg) mice did not differ in immobility time (FIG. 2B). SD-K (30 mg kg$^{-1}$) mice again displayed significantly less immobility when compared with SD-Sal mice (FIG. 2C). SD-Sal and SDK (90 mg kg$^{-1}$) mice did not differ in immobility time (FIGS. 2D, 2E).

As the hypothalamic-pituitary-adrenal (HPA) axis is dysregulated in mice following SD (14), we also tested whether ketamine protected against the deleterious effect of SD on the stress response. Following a brief stressor. SD-Sal mice had significantly lower levels of CORT than Ctrl-Sal mice (FIG. 2F), suggesting that SD blunts the response of the HPA axis. However, all ketamine-injected mice did not differ from Ctrl-Sal mice, suggesting that ketamine partially restores the HPA axis. To determine if adult hippocampal neurogenesis was modulating, as least in part, these effects, we measured maturation of newborn neurons and proliferation of newborn neurons by quantifying the levels of doublecortin and Ki67, respectively. We did not observe an effect of ketamine on adult hippocampal neurogenesis.

These data suggest that the ketamine improvement in depressive-like behavior may be mediated in part by changes in HPA functionality but not necessarily by adult hippocampal neurogenesis.

Prophylactic Ketamine Alters Fighting Behavior During SD Bouts

Figure 5A:
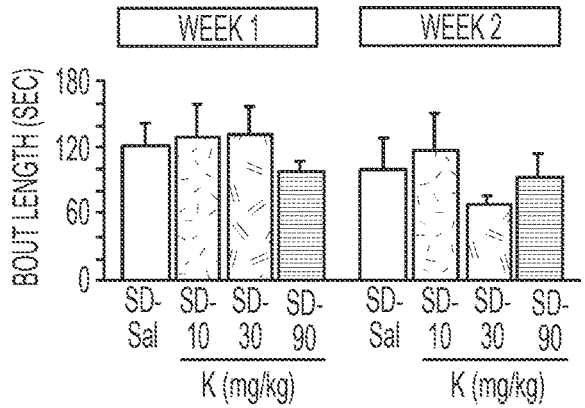
FIGS. 5A-5G are graphs showing that ketamine alters fighting behavior during social defeat bouts. FIG. SA is a graph showing that the bout length did not differ for all groups of mice during week 1 or week 2.
Figure 5B:
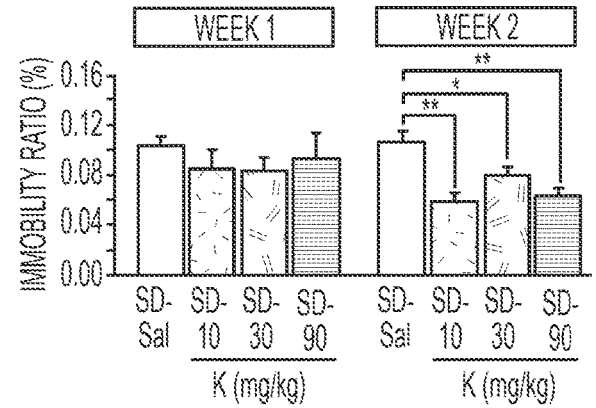
Figure 5C:
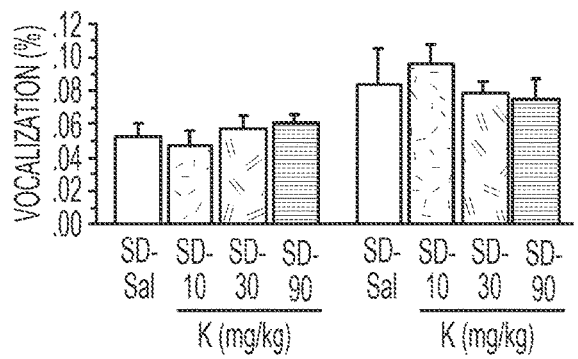
Figure 5D:
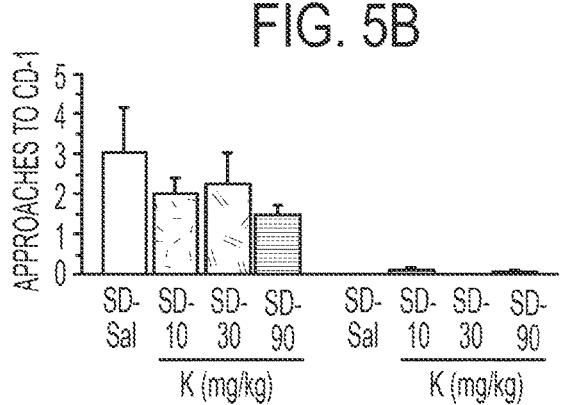

To determine if ketamine also affected behavior during SD, we analyzed individual fighting bouts. The total fighting bout length did not differ between groups (FIG. 5A). However, the average immobility during week 2 was significantly decreased in SD-K mice when compared with SD-Sal mice (FIG. 5B). The percent of time vocalizing (FIG. 5C) and number of approaches to the CD-1 (FIG. 5D) did not differ between the groups. These data suggest that mice administered ketamine may not be as fearful of the CD-1 mice and, therefore, spend less time immobile.

Figures 5E, 5F, 5G:
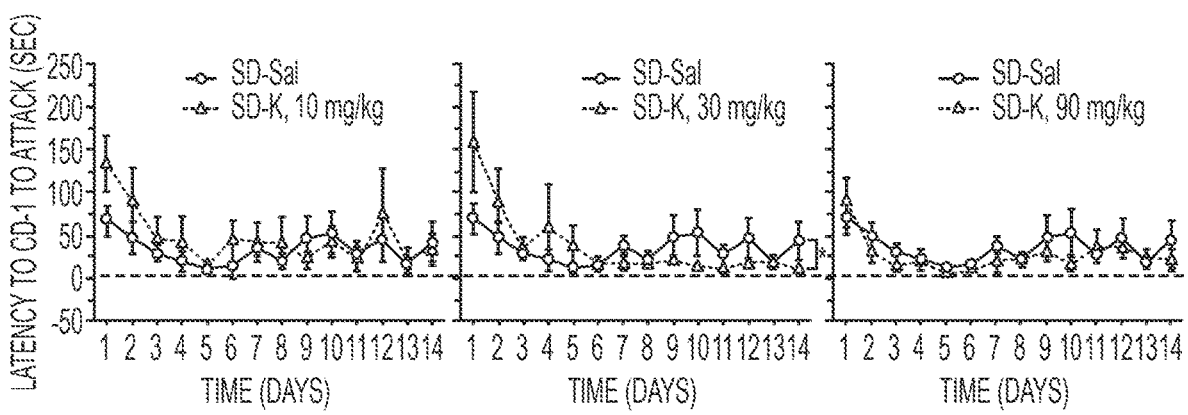

We next analyzed the latency of the CD-2 to attack the 129S6/SvEv mouse (FIG. 5E-G). CD-1s comparably attacked SD-Sal and SD-K (10 or 90 mg kg21) mice. However, at the start of SD, CD-1s attacked SD-K (30 mg kg$^{-1}$) mice significantly later than SD-Sal mice. These data suggest that perhaps the mice receiving K (30 mg kg$^{-1}$) have an advantageous ongoing response to SD when compared with Sal mice.

Fluoxetine Treatment Before SD Does Not Protect Against the Induction of Depressive-Like Behavior We next determined if this protective effect of ketamine extended to other antidepressants. Mice were administered 3 weeks of fluoxetine (Flx) (18 mg kg$^{-1}$) treatment before the start of SD. On day 2 of the FST, Ctrl-Vehicle (Veh) and Ctrl-Flx displayed equal levels of immobility time. In SD mice, fluoxetine did not improve immobility time induced by SD. These data indicate that fluoxetine, unlike ketamine, is not capable of preventing stress-induced behavioral despair as measured by the FST.

We also assessed a number of other behaviors following fluoxetine treatment. Fluoxetine treatment did not significantly alter anxiety or cognition but did affect metabolism. Interestingly, unlike SD-K (30 mg kg$^{-1}$)mice, SD-Flx mice do not display differences during SD bouts when compared with SD-Veh mice. These data suggest that fluoxetine treatment cannot protect against depressive-like behavior as ketamine does.

Ketamine Administered After SD Does Not Improve Depressive-Like Behavior

To compare the robustness of prophylactic ketamine relative to its typical use as an antidepressant, we next asked if ketamine could improve behavioral despair if administered after SD. Mice were administered 2 weeks of SD and then received one injection of saline or ketamine the day after the final SD session. On day 2 of the FST, Ctrl-Sal and Ctrl-K mice did not display different immobility time. SD-Sal and SD-K mice had similar levels of immobility time. We averaged minutes 3 to 6 and found that SD increased immobility time, but ketamine given after SD did not decrease immobility time. These data indicate that ketamine more potently decreases behavioral despair in the FST when given as a prophylactic before SD than after SD.

We also assessed a number of other behaviors following ketamine treatment (FIGS. 6A-6K). In Ctrl mice, ketamine decreased the latency to eat in the NSF when compared with saline (FIG. 6A). This effect was abolished in the SD mice, most likely due to weight loss differences between Ctrl and SD mice (FIGS. 6B-6C). Interestingly, ketamine lessened the percentage of weight loss in the SD mice when compared with saline, possibly by protecting against stress-induced hypophagia (FIG. 6D). Ketamine also did not impact CFC learning (FIG. 6G-6J). Most importantly, although we did not detect differences from prophylactic ketamine treatment, we did determine that ketamine administered after SD significantly increases the number of Ki671 cells in the dentate gyros (FIG. 6K).

Prophylactic Ketamine Protects Against Learned Helplessness

Figure 3A:
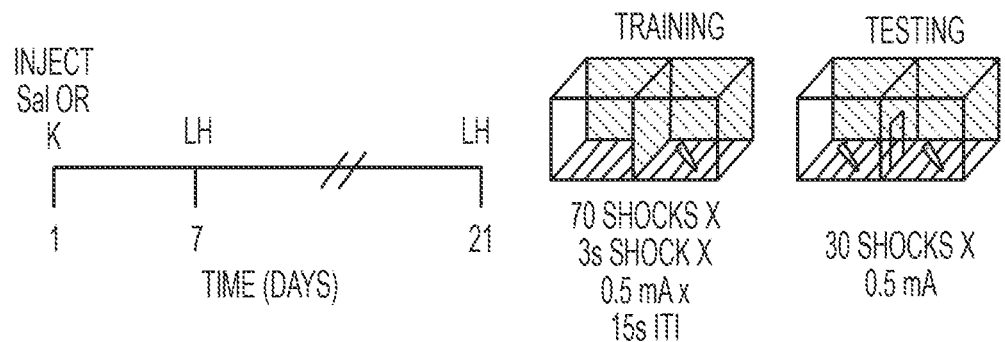
FIGS. 3A-3E are schematics and graphs showing that ketamine (K) protects against depressive-like behavior in learned helplessness (LH).
Figure 3B:
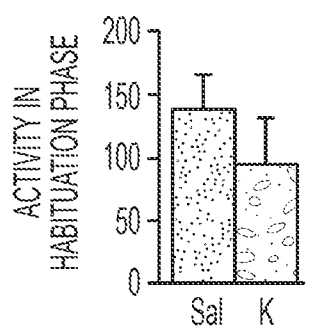
Figure 3C:
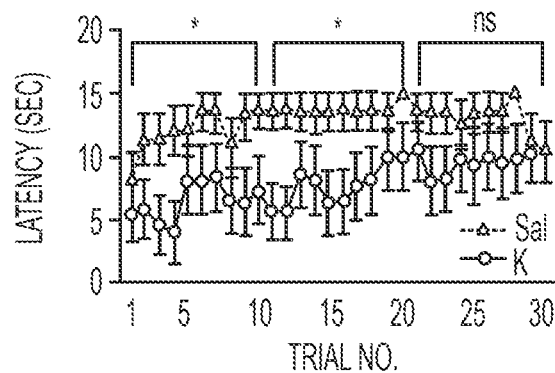
Figure 3D:
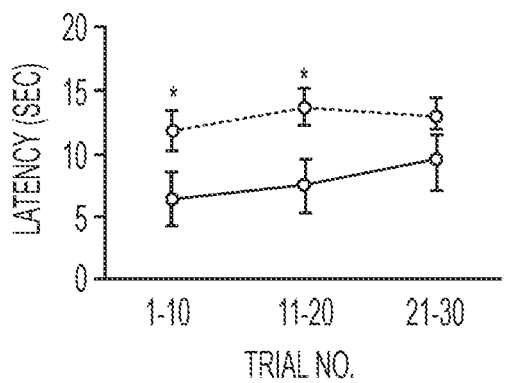
Figure 3E:
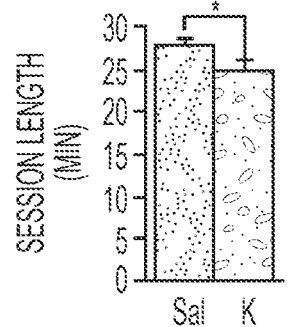

We hypothesized that ketamine would protect against LH, a paradigm in which a mouse is exposed to inescapable shocks (28-30). Mice were injected with saline or ketamine and administered an inescapable shock stress protocol (LH training) 1 week later (FIG. 3A). Two weeks later, mice were administered a shock escape protocol (LH testing) and the latency to escape the shock was measured. The activity in the habituation phase during testing did not differ between mice administered saline or ketamine (FIG. 3B). However, mice injected with ketamine had a decreased latency to escape the shock when compared with mice injected with saline (FIGS. 3C, 3D). Moreover, the session length was significantly shorter in the ketamine mice than in the saline mice (FIG. 3E). These data indicate that ketamine protection is not just limited to SD stress.

Prophylactic Ketamine Protects Against the Depressive-Like Effects of Chronic Corticosterone Treatment To address whether ketamine was protective in a third stress model, we utilized a mouse model of anxiety/depression based on elevation of glucocorticoids (3 weeks of chronic CORI administration in C57BL/6NTac mice) (27). We tested the protective effects of a chronic fluoxetine treatment (18 mg kg$^{-1}$ for 3 weeks) or a single injection of ketamine (10, 30, or 90 mg kg$^{-1}$) given before CORT administration (FIG. 4A). We found that ketamine (90 mg kg$^{-1}$) and fluoxetine prevented the CORT-induced increase in body weight.

Both ketamine (90 mg kg$^{-1}$) and fluoxetine decreased immobility time on day 2 in the FST (FIGS. 4B, 4C). Chronic CORT induced depressive-like symptoms (e.g., increased grooming latency) in the ST (FIG. 4D). Here, ketamine (90 mg kg$^{-1}$), but not fluoxetine, prevented the chronic CORT-induced depressive-like phenotype (FIG. 4D). These data indicate that the protective effect of ketamine extends to a third depression model.

In the NSF, ketamine (10 and 90 mg kg$^{-1}$) prevented the chronic CORT-induced increase in latency to feed (FIG. 4E). However, only ketamine (90 mg kg$^{-1}$) increased home cage food consumption (FIG. 4F).

Finally, we assayed anxiety behavior using the EPM. CORT-Veh mice spent more time in the closed arms than Veh-Veh mice. Neither ketamine nor fluoxetine robustly protected against this anxiety-like phenotype. In summary, these data suggest that 90 mg kg$^{-1}$ of ketamine is the most effective dose in protecting against depressive-like behavior following chronic CORT treatment in C57BL/6NTac mice.

Ketamine Administered After Chronic. Corticosterone Does Not Improve Depressive-Like Behavior Finally, as in the SD model, we measured the behavioral impact of ketamine when given after CORT, in this experimental design, mice were administered 4 weeks of CORT and then received either one injection of saline or ketamine, tar vehicle or fluoxetine for 2 weeks. Here, we utilized the tail suspension test (TST) and the NSF to test the same behavior on multiple occasions.

Fluoxetine, but not ketamine, decreased immobility time in the TST at both time points tested following CORT. In the NSF, CORT treatment increased the latency to feed when compared with Veh treatment. Fluoxetine, but not ketamine, decreased the latency to feed 14 days, but not 7 days, after the start of treatment. In summary, as previously demonstrated in the SD model, these data further indicate that ketamine more potently improves depressive-like behavior when given as a prophylactic before CURT treatment rather than after CORT treatment.

DISCUSSION

Here, we have shown that a single injection of ketamine administered before SD protected mice against stress-induced increased immobility time in the FST. Additionally, ketamine protected mice against stress-induced social avoidance of an aggressor mouse. We found that mice administered ketamine before SD were protected against stress-induced depressive-like behavior, but consistent with the literature definition of stress resilience, their behavior in anxiety tests and levels of adult hippocampal neurogenesis were not significantly altered. Interestingly, in the SD paradigm, only a subanesthetic dose (30 mg kg$^{-1}$) of ketamine was found to be effective.

The prophylactic effect of ketamine was recapitulated in two additional models, in LH, ketamine decreased depressive-like, helpless behavior. In the CORT model, ketamine was protective against depressive-like behaviors (FST, ST), anxiety (NSF), and metabolic changes (body weight), albeit at a slightly higher dose (90 mg kg$^{-1}$) than in SD or LH. The efficacy of the higher dose in the CURT model is perhaps attributable to mouse strain differences (C57BL/6NTac versus 129S6/SvEv). Nevertheless, the dose administered in the CURT model is in the anesthetic range, whereas the dose in the SD/LH model is subanesthetic. If an equivalent anesthetic dose were required to obtain prophylactic efficacy in humans, acute side effects would need to be considered when developing treatment regimens.

Administration of the classic antidepressant fluoxetine before stress did not consistently or robustly protect against stress-induced depressive-like behavior. In the SD model, fluoxetine did not improve immobility time in the FST, but in the CURT model, fluoxetine protected against immobility time in the FST and body weight alterations.

Though preventing psychopathology has obvious advantages over noncurative medication regimens, we also wanted to assess the relative potencies of ketamine's protective and antidepressant effects. Interestingly, when ketamine was administered following stress, we did not Observe a significant decrease in immobility time in the FST air TST. In our SD model, we utilized a 30 mg kg$^{-1}$ dose, but in the CORT model, we utilized a 10 mg kg$^{-1}$ dose to compare with more recent studies using ketamine as an antidepressant in C57BL mice (12,33). This suggests that the beneficial effects of ketamine on stress-induced pathology may be more robust when given before stress. In contrast, Donahue et al. (12) recently found the converse when they administered ketamine either 1 hour after the final SD session or 24 hours before the first SD session. A high (20 mg kg$^{-1}$)—but not low (2.5 mg kg$^{-1}$)—dose of ketamine following the final SD session attenuated social avoidance but not anhedonia. Conversely, when ketamine (20 mg kg$^{-1}$) was administered before SD, it did not attenuate social avoidance. The lack of effect in their experiments, however, does not mean that ketamine's protective effect is not as robust as we suggest. The effect of ketamine is less likely effective, as a C57BL/6J strain is utilized in the Donahue et al. (12) study, but as we have shown in the CORT model, a higher dose is necessary for prophylactic efficacy in C57BL mice. Ketamine dosing for prophylactic administration may or may not differ from antidepressant administration.

Ketamine-induced resilience is robust and long lasting—persisting at least 3 weeks post-injection in the SD model and 4 weeks post-injection in the CORT model. It is worth noting that as the half-life of ketamine is only a few hours in rodents (39), ketamine is not bioactive at any point during the SD fighting bouts, LH, or CORT administration. Thus, the process by which ketamine protects against depressive-like behavior is necessarily self-maintaining. We have shown that ketamine can alter ongoing response to a chronic stressor. In the SD model, our data suggest that ketamine alters the way in which mice react to the fighting bouts, which may contribute to the differences in developing depressive-like behavior at a later time point. Not only do the SD-K (30 mg kg$^{-1}$) mice have a decreased immobility time during the fighting bouts, but also the CD-1 mice attack the SD-K (30 mg kg$^{-1}$) mice at greater latencies.

In summary, these experiments demonstrate that ketamine has a long-lasting resilience-enhancing effect and protects against the deleterious effects of chronic stress on depressive-like behaviors. Because the protective effect of ketamine persists beyond its half-life of 2 to 2.5 hours, the prophylactic effect may be useful as a vaccine-like strategy in at-risk populations where high-stress conditions can be predicted. Active combat soldiers offer a good example of a predictably at-risk patient population. Administration of ketamine before deployment may mitigate the emergence of posttraumatic stress disorder or other stress-related disorders in this vulnerable population. In humans, ketamine may offer a novel, clinic-ready approach to protect and prevent at-risk patients from developing stress-induced disorders.

Example 2

Prophylactic Ketamine Reduces Fear Expression

Ketamine has been reported to be an efficacious antidepressant for major depressive disorder (MDD) and posttraumatic stress disorder (PTSD). Most recently, ketamine has also been shown to be prophylactic against stress-induced depressive-like behavior in mice. It remains unknown, however, when ketamine should be administered relative to a stressor in order to maximize its antidepressant and/or prophylactic effects. Moreover, it is unknown if ketamine can be prophylactic against subsequent stressors.

We systematically administered ketamine at different time points relative to a fear experience in order to determine when ketamine is most effective at reducing fear expression or preventing fear reactivation. Using a contextual fear conditioning (CFC) paradigm, mice were administered a single dose of saline or ketamine (30 mg kg$^{-1}$) at varying time points before or after CFC.

Mice administered prophylactic ketamine 1 week, but not 1 month or 1 hour before CFC, exhibited reduced freezing behavior when compared with mice administered saline. In contrast, ketamine administration following CFC or during extinction did not alter subsequent fear expression. However, ketamine administered before reinstatement increased the number of rearing bouts in an open field, possibly suggesting an increase in vigilance.

These data indicate that ketamine can buffer a fear response when given a week before as prophylactic, but not when given immediately before or after a stress-inducing episode. Thus, ketamine may be most useful in the clinic if administered in a vaccine-like fashion in order to protect against heightened fear responses to aversive stimuli.

Example 1 describes our findings that ketamine administered as a prophylactic protects against the onset of stress-induced depressive-like behavior in three different mouse models of stress (Brachman et at, 2016, reviewed in Price, 2016). This work was replicated by an independent group who found similar effects of ketamine in rats (Amat et al., 2016). In this study, in order to better understand when ketamine should be given relative to a stressful episode, we systematically administered ketamine at various time points during a CFC extinction paradigm. We hypothesized that at certain time points ketamine would be prophylactic against fear expression, while at other time points ketamine would be ineffective or increase fear expression. Mice administered prophylactic ketamine 1 week, but not 1 month, before CFC exhibited reduced freezing behavior when compared with mice administered saline. In contrast, ketamine administration following CFC or before extinction did not alter subsequent fear expression. Interestingly, ketamine administration following extinction, but before reinstatement, increased rearing in the open field, which may reflect increased vigilance. These data indicate that ketamine can buffer a fear response when given as a prophylactic, but not when given immediately before or after a stress-inducing episode.

METHODS AND MATERIALS

Mice

129S6/SvEvTac mice were purchased from Taconic (Hudson, N.Y.) at 8 weeks of age. Mice were housed 4-5 per cage in a 12-h (06:00-18:00) light-dark colony room at 22° C. Food and water were provided ad libitum. Behavioral testing was performed during the light phase. All experiments were approved by the Institutional Animal Care and Use Committee at Columbia University and the New York State Psychiatric Institute.

Drugs

A single injection of saline (0.9% NaCl) far ketamine (30 mg kg$^{-1}$) (Ketaset III, Ketamine HCl injection, Fort Dodge Animal Health, Forth Dodge, Iowa) was administered once during the course of each experiment. Ketamine was prepared in physiological saline and all injections were administered intraperitoneally (i.p.) in volumes of 0.1 cc per 10 mg body weight.

Contextual Fear Conditioning (CFC)

A 3-shock CFC paradigm was administered as previously described (Drew et al., 2010; Denny et al., 2014). Mice were placed in the conditioning chamber and received 3 shocks 180, 240, and 300 s later (2 s, 0.75 mA) and were removed 15 s following the last shock. All sessions were scored for freezing using FreezeView2http://actimetrics.com/downloads/freezeframe/).

Extinction (E)

Initially, two extinction protocols based off of Trouche et al. (2013) and Sananbenesi et al., (2007) were piloted in order to determine the best conditions for assessing the effectiveness of ketamine (FIG. 14). The extinction procedure chosen was the most consistent and robust, and was based on the protocol from Trouche et al. (2013). Extinction began 4 days after the initial 3-shock CFC procedure, or 4 days after the reinstatement procedure. Each group of mice was subjected to 2 extinction trials per day. Each extinction trial lasted 30 min, with an intertrial interval of at least 2 h.

For each extinction trial, mice were placed in the same box used for CFC without receiving foot shocks. All trials were scored for freezing. The freezing presented throughout the text represents averaged freezing behavior for the first 3 min of each extinction trial.

Reinstatement (R)

Reinstatement took place in the same Coulbourn fear conditioning box, but with altered cues. A 1-shock CFC paradigm was administered as previously described (Drew et al., 2010; Denny et al., 2012; Denny et al., 2014), with the exception of two experiments in which the mice were administered 3 shocks.

Forced Swim Test (FST)

The FST was administered as previously described (Richardson-Jones et al., 2010; Brachman et al., 2016).

Open Field (OF)

OF protocol was administered as previously described (Richardson-Jones et al., 2010).

Statistical Analysis

All data were analyzed using. StatView 5.0 software (SAS institute, Cary, N.C.) or Prism 5.0a. Alpha was set to 0.05 for all analyses. In general, the effect of Drug or Context was analyzed using an analysis of variance (ANOVA), using repeated measures where appropriate. Significant ANOVAs were followed up with Fisher's protected least significant difference post-hoc analysis or unpaired t-tests where appropriate.

RESULTS

An injection of Ketamine 1 Week Prior to CFC Decreases Fear Expression

Figure 7A:
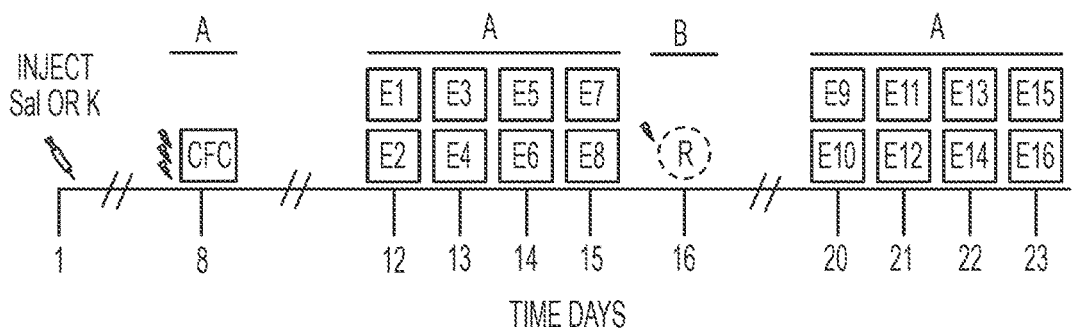
FIGS. 7A-7E are experimental design schemes and graphs showing that prophylactic ketamine administration 1 week before CFC results in a decreased fear response.
Figure 7B:
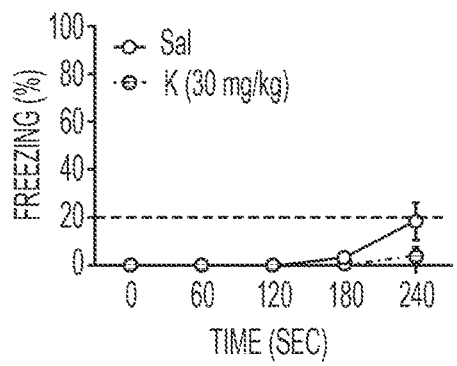
Figure 7C:
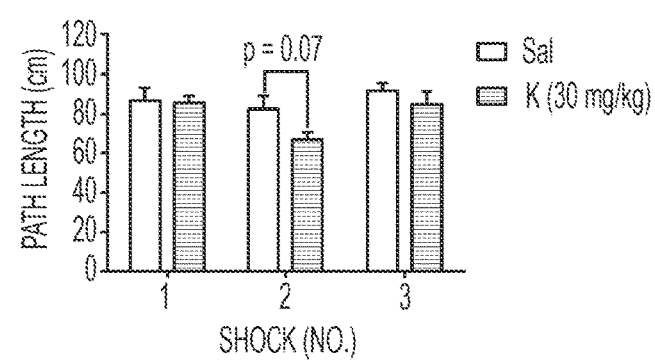

First, to determine if our previously reported prophylactic effect of ketamine extended to CFC, mice were administered a single injection of saline or ketamine (30 mg kg$^{-1}$) (FIG. 7A). One week later, mice were trained using a 3-shock CFC protocol. Both groups of mice exhibited comparable levels of freezing during the 3-shock CFC training (FIG. 7B). Moreover, both groups of mice traveled comparably during each of the 3 shock presentations (FIG. 7C).

Figure 7D:
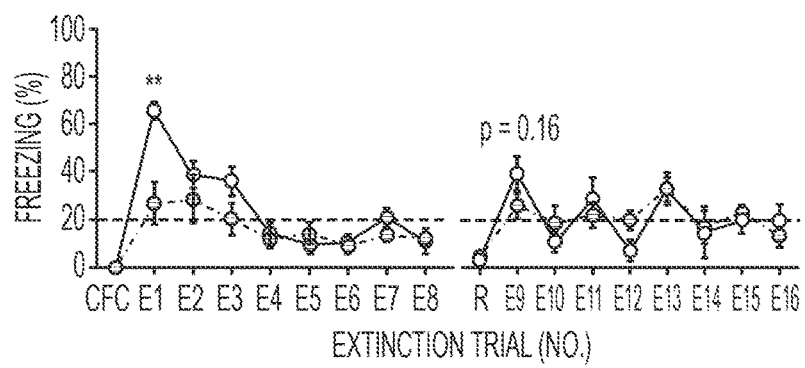
Figure 7E:
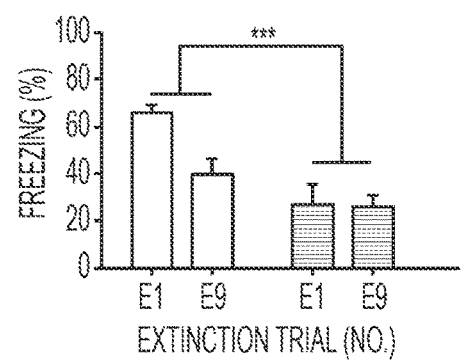

Extinction training began four days later after the CFC. During the first extinction exposure, mice injected with prophylactic ketamine expressed significantly less freezing behavior when compared with mice injected with saline (FIG. 7D). Both groups of mice expressed similar levels of freezing behavior during subsequent extinction trials, reinstatement, and secondary extinction trials. When the first trial of extinction and the first trial of re-extinction were compared (E1 vs. E9), ketamine-injected mice significantly decreased levels of fear than saline-injected mice (FIG. 7E). These data indicate that ketamine is efficacious in buffering fear expression when administered as a prophylactic 1 week before CFC.

An Injection of Ketamine 1 Month Prior to CFC Does Not Alter Fear Expression

Figure 8A:
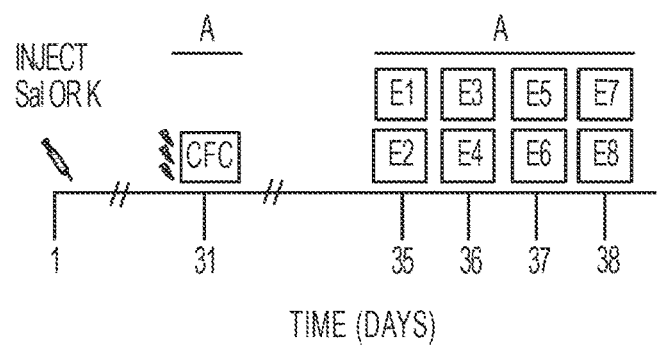
FIGS. 8A-8D are experimental design schemes and graphs showing that prophylactic ketamine administration 1 month before CFC does not result in a decreased fear response or facilitate extinction.
Figure 8B:
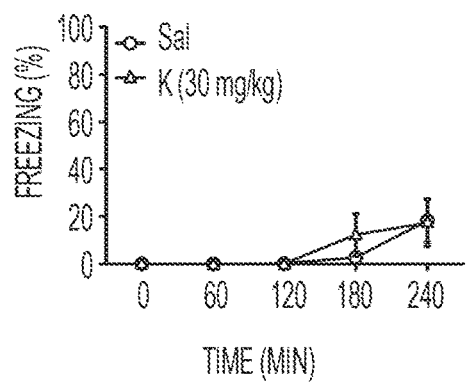
Figure 8C:
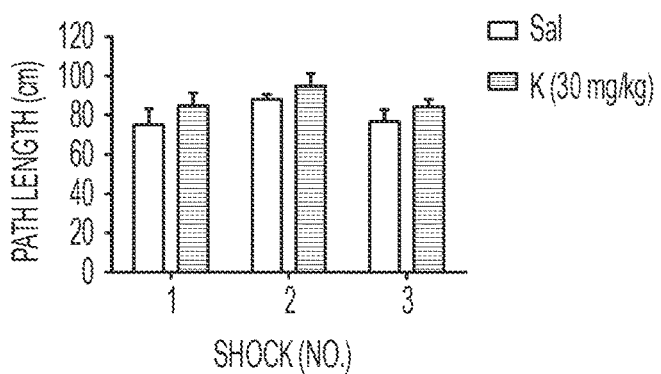
Figure 8D:
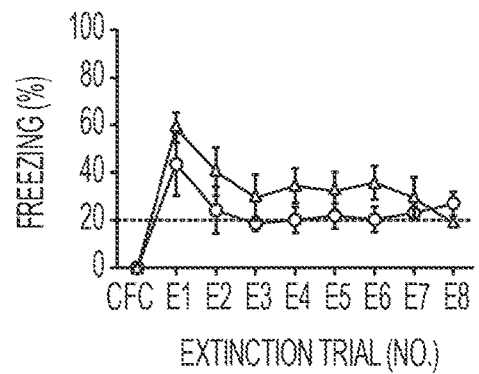

In order to determine if administering ketamine at additional points before a fear-inducing stimuli might be beneficial, we varied the interval from 1 week to 1 month before CEC (FIG. 8A). Prophylactic ketamine administration 1 month before CFC did not result in a decreased fear response during CFC training (FIG. 8B), did not alter the shock response (FIG. 8C), and did not alter freezing behavior during extinction (FIG. 8D) compared to saline administration. These data indicate that there is a defined interval at which ketamine may be administered prior to a stressor in order to buffer against fear expression.

An Injection of Ketamine 1 Hour, but Not 24 Hours Prior to CFC Increases Freezing Behavior We next varied the interval immediately before CFC training. We first administered ketamine 1 h before CFC (FIG. 9A), Ketamine administration resulted in increased immobility prior to the shock presentation (FIG. 9B). Ketamine-injected mice traveled less during each of the three shock presentations than saline-injected mice (FIG. 9C). However, both groups of mice froze comparably during extinction (FIG. 9D).

Figure 9G:
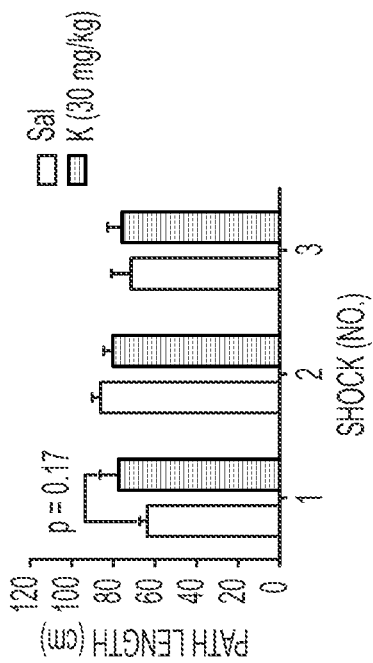
Figure 9H:
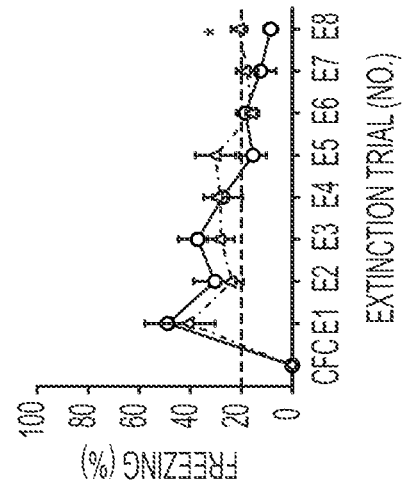
Figure 9E:
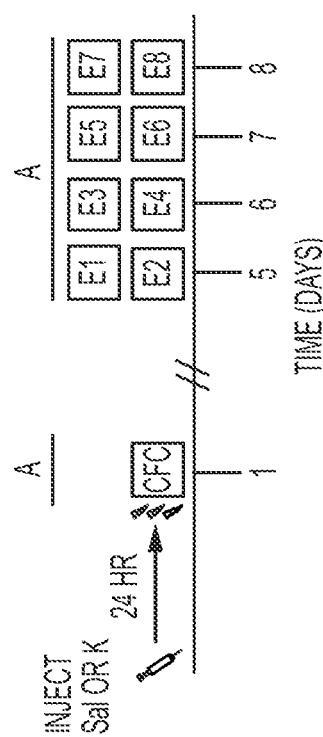
Figure 9F:
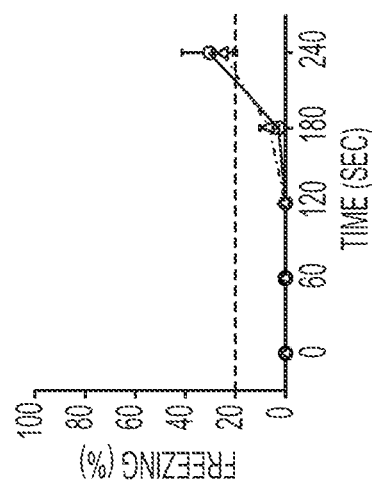

Next, we administered ketamine 24 h before CFC (FIG. 9E). Ketamine administration did not alter immobility prior to the shock presentation, path length during the shocks, or freezing behavior during extinction (FIGS. 9F-9H). These data indicate that there is a defined window at which ketamine may be administered prior to a stressor in order to buffer or decrease a fear expression.

Figure 10A:
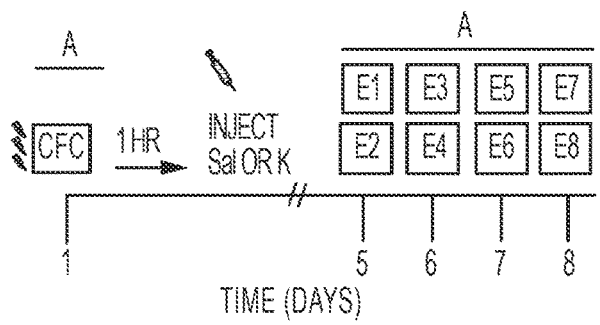
FIGS. 10A-10F are experimental design schemes and graphs showing that ketamine administration does not facilitate extinction when administered following CFC.
Figure 10B:
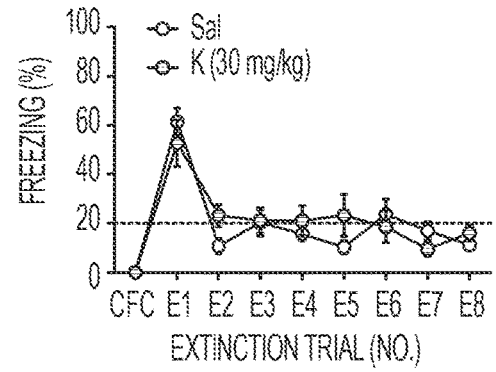

An Injection of Ketamine Following CFC or Prior to Extinction Does Not Alter Fear Expression To determine if an injection of ketamine could alter fear extinction behavior following the encoding of an initial stressor, we next tested administration following CFC at various time points. Mice were injected with ketamine 1 h following 3-shock CFC training (FIG. 10A). A single injection of ketamine following CFC did not alter fear expression during extinction (FIG. 10B).

Figure 10C:
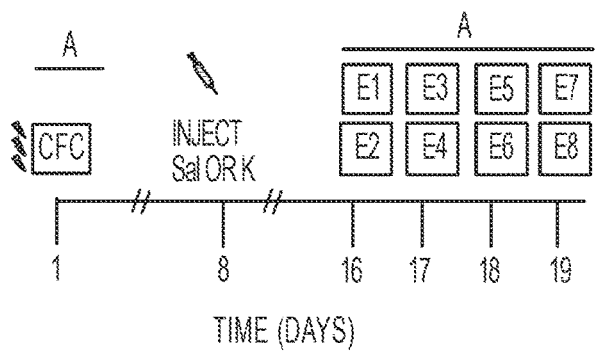
Figure 10D:
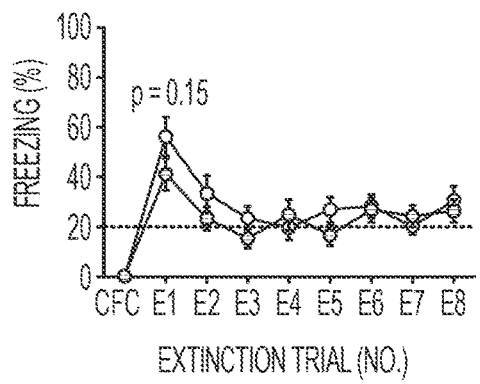

Mice were then injected with ketamine 1 week following CFC but 1 week prior to extinction in order to mimic the 1-week interval that we use as a prophylactic (FIG. 10C). A single injection of ketamine prior to extinction did not alter fear expression during extinction training (FIG. 10D).

Figure 10E:
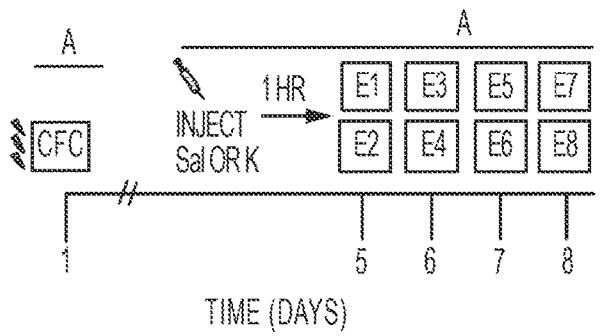
Figure 10F:
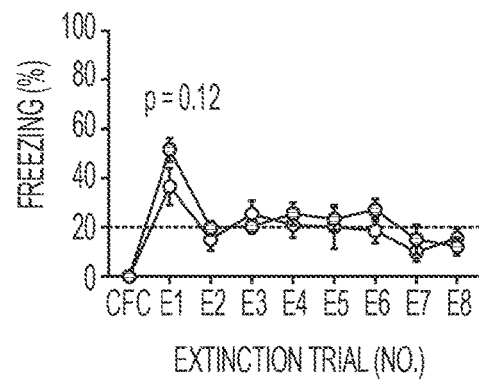

Lastly, mice were injected with ketamine 1 h prior to extinction (FIG. 10E). A single injection of ketamine prior to extinction did not alter fear expression during extinction training (FIG. 10F). These data suggest that ketamine administration following the encoding of a stressor does not alter the subsequent fear response.

An Injection of Ketamine 1 Week Prior to Reinstatement increases Vigilance, but Does Not Decrease Fear Expression Since our data indicated that that a single injection of ketamine 1 week prior to 3-shock CFC reduces fear expression, we sought to determine whether ketamine administered prior to reinstatement would alter subsequent fear expression or alter behavior in other stressful paradigms (FIG. 11A).

A single injection of ketamine 1 week prior to 1-shock reinstatement did not alter subsequent fear expression (FIG. 11). Saline- and ketamine-injected mice traveled comparably during the shock presentation given during reinstatement (FIG. 11C). We next tested if ketamine could alter stress-related behavior, as measured by behavioral despair in the FST or locomotion in the OF. Both groups of mice displayed similar time immobile in the FST (FIG. 11D), and had comparable locomotion during the OF (FIG. 11E). However, mice that received ketamine had a higher number of rearing bouts during the OF (FIG. 11F). These data indicate that an injection of ketamine prior to 1-shock reinstatement of a stressor does not buffer against fear expression. However, a single injection of ketamine prior to reinstatement increases vigilance as measured by the number of rearing bouts in an OF. We next wanted to determine if the strength of the reinstatement experience influenced ketamine's effects on vigilance described above. Here, ketamine was administered 1 week prior to a 3-shock reinstatement trial instead of a 1-shock reinstatement trial (FIG. 11G). A single injection of ketamine 1 week prior to 3-shock reinstatement did not alter fear expression (FIG. 11H). Saline- and ketamine-injected mice traveled comparably during each of the 3 shock presentations (FIG. 11I). As with the 1-shock reinstatement experiment, both groups of mice displayed similar time immobile in the FST (FIG. 11J) and basic movements during the OF (FIG. 11K), in contrast to the 1-shock reinstatement experiment, both groups had a comparable number of rearing bouts during the OF (FIG. 11L) and these levels were similar to the saline-injected group described above (FIG. 11F). These data indicate that an injection of ketamine prior to a strong reinstatement experience does not buffer against subsequent fear-inducing stimuli, or influence depressive-like or exploratory behavior in the FST and OF respectively.

Figure 12A:
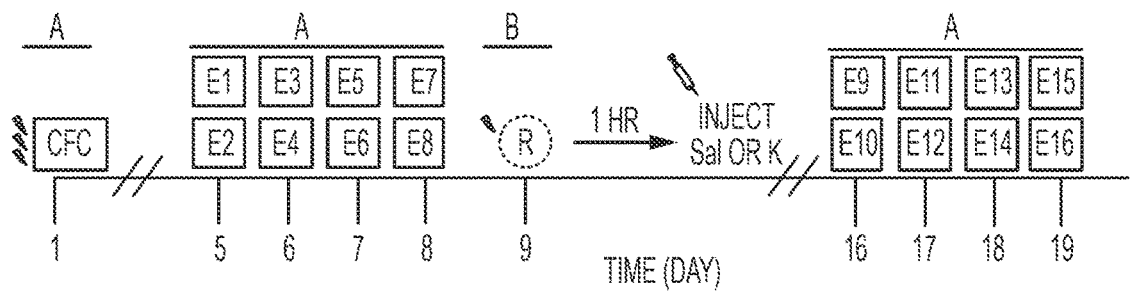
FIGS. 12A-12E are experimental design schemes and graphs showing that ketamine administration following reinstatement decreases fear following 3-shock CFC, but not 1-shock CFC.
Figure 12B:
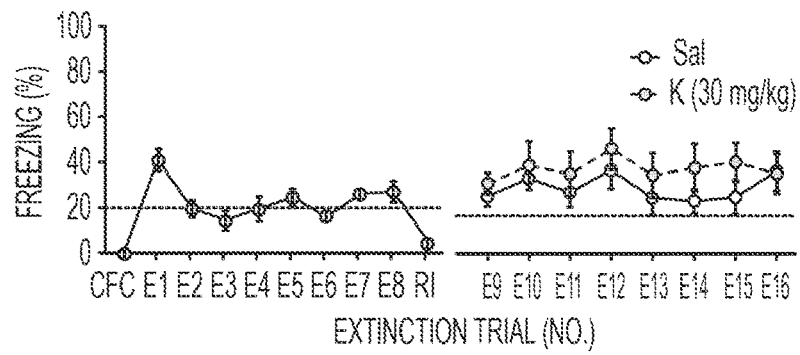

An Injection of Ketamine Following Reinstatement Does Not Alter Subsequent Fear Expression In order to determine whether administration of ketamine following reinstatement would influence subsequent fear expression, we next tested administration following the reinstatement experience at various time points. We first administered ketamine 1 h after a 1-shock reinstatement paradigm (FIG. 12A). A single injection of ketamine 1 h following a 1-Shock reinstatement did not alter subsequent fear expression (FIG. 12B).

Figure 12C:
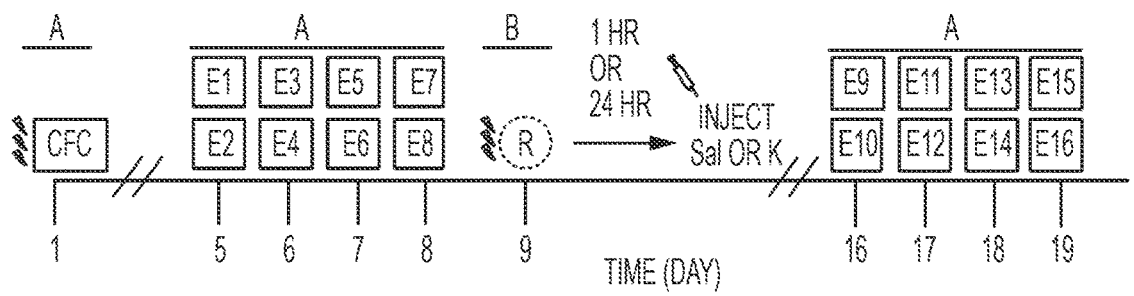
Figure 12D:
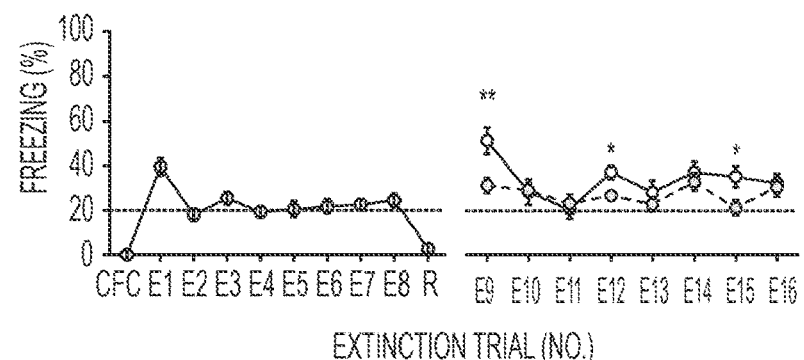
Figure 12E:
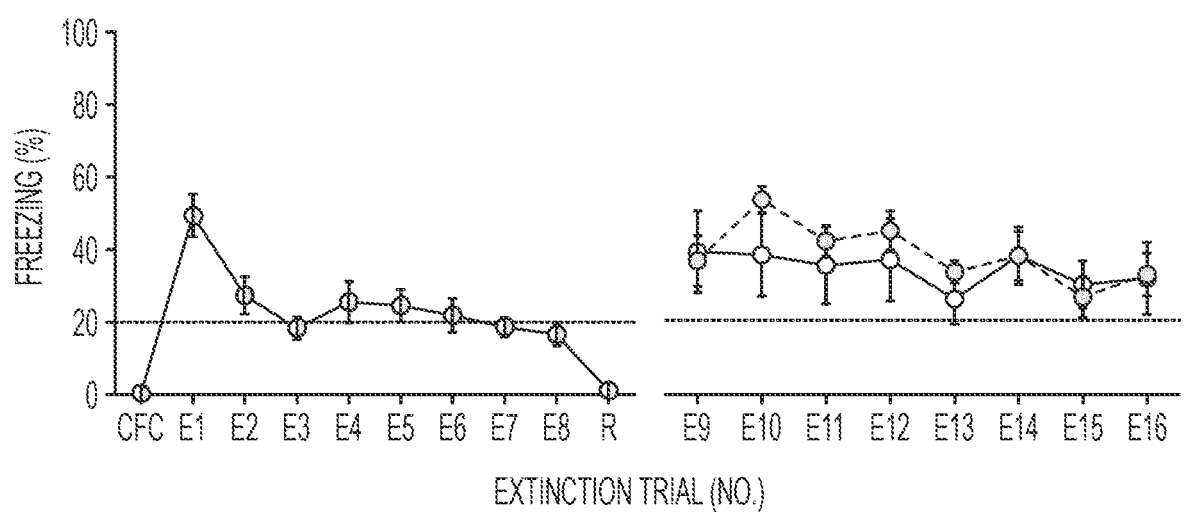

Ketamine was then administered 1 h after a 3-shock reinstatement paradigm in order to determine whether the strength of the reinstatement experience would influence differences in subsequent fear expression (FIG. 12C). Interestingly, a single injection of ketamine 1 h after a 3-shock reinstatement buffered fear expression during the first re-exposure, and transiently decreased freezing throughout extinction (FIG. 12D). We also tested ketamine administration at a 24 h time point following a 3-shock reinstatement. A single injection of ketamine 24 h following 3-shock reinstatement did not alter subsequent fear expression (FIG. 12E).

DISCUSSION

Here, our results suggest that the timing of administering ketamine is critical for its effectiveness for buffering fear expression. We show that a single injection of ketamine administered 1 week before the start of CFC was most effective as a prophylactic in buffering against a heightened fear response. However, it does not facilitate extinction or alter subsequent behavior. Ketamine administered 1 month or 1 hour before the start of CFC does not buffer against a fear response or facilitate extinction. These data suggest that there is a limited time window for prophylactic protection. Additionally, ketamine administered following CFC does not alter subsequent freezing levels. Yet, interestingly, ketamine administered 1 hour after a strong reinstatement protocol decreased fear expression, suggesting a potential window of efficacy. Lastly, ketamine administration following extinction but before reinstatement does not alter freezing levels, yet it increases rearing in the OF, a possible measure of vigilance. This increase in rearing in the OF is abolished following a strong reinstatement paradigm, indicating that the intensity of the stressor influences the effectiveness of ketamine on rearing.

The prophylactic effect that we have previously reported in three different models of stress was replicated here (Brachman et al., 2016). We initially reported that ketamine administered 1 week before social defeat (SD), learned helplessness (LH) or chronic corticosterone (CORT) protected against depressive-like behavior. Here, we see a similar effect by using CFC as a stressor: prophylactic ketamine buffers the stress response when administered 1 week before CFC training. Notably, ketamine's prophylactic efficacy is dependent on when it is administered prior to a fear-inducing stimulus, as a protection was not observed with the 1-month time point. Therefore, there is likely a defined window as to when ketamine may confer its most effective therapeutic potential.

It is interesting to note that ketamine administered immediately before CFC resulted in increased immobility and a blunted response to the shocks. This effect was seen only when ketamine was administered 1 h, but not 24 h before CFC. This increase in immobility is most likely due to altered pain sensitivity as it has been reported that following an i.p. injection of ketamine, animals have an increased reaction time to the hot plate test (Takahashi et al., 1986).

These data show that acute ketamine administration induces an analgesic effect. It is notable that the present study did not observe increased freezing or blunted response to the shocks when ketamine was administered 24 h before CFC. It is likely that the analgesic effects of the drug persist for 1 h, but not 24 h post-injection, as ketamine is known to have a half-life of approximately 2.5 h (Wither et al., 1975). Thus, administering ketamine immediately prior to a stressor may interfere with the perception of pain during a stressor.

To extend the earlier PTSD and ketamine studies in US service members (McGhee et al., 2008; McGhee et al., 2014) to rodent models, we administered ketamine 1 h after CFC, week after CFC, or 1 h before extinction training. While the initial McGhee study (McGhee et al., 2008) found a reduction in the incidence of PTSD, the later study found a comparable incidence rate of PTSD in US military personnel treated with and without intraoperative ketamine (McGhee et al., 2014). Our findings are in agreement with the later study we did not find post-exposure administration to be effective in reducing the fear response. These results align with our previous data (Brachman et al., 2016) in which ketamine administered following a stressor did not prevent against stress-induced depressive-like behaviors and with a previous rodent study in rats which found that immediate ketamine treatment following a psychogenic stressor did not prevent the onset of PTSD (Juven-Wetzler et al., 2014). It is essential to consider, however, the variable histories of the patients treated in both. McGhee studies. While our rodent studies correlate with findings that suggest ketamine is not effective in preventing the onset of PTSD when administered immediately after the trauma, we believe that the history and individual timing of the ketamine administration is critical in determining the effectiveness of the treatment.

We found that ketamine 1 week prior to reinstatement did not alter fear expression, contrary to the effect of prophylactic ketamine 1 week before CFC. These data demonstrate that ketamine is most effective when administered as a prophylactic before an initial stressor rather than before relapse or reinstatement of the stressor, consistent with what is known about primary prophylaxis. Furthermore, it suggests that previous stressors influence subsequent stressor responses. While ketamine administration did not affect locomotion in the OF, it did increase the number of rearing bouts. It has been suggested that rodents' rearing on hind legs can be a measure of attention and vigilant behavior, as it demonstrates increased interest in the spatial environment, as well as a lower perceived threat (Lever et al., 2006). However, there is a scarcity of analysis on the significance of rearing in rodents for anxiolytic behaviors, though it is often interpreted as an exploratory response to novel stimuli (van Abeelen, 1975; van Abeelen, 1977; Crusio, 200). More recently, the 5-choice continuous performance test (5C-CPT) has been adapted from human studies to rodents in order to assess vigilance (Young et al., 2009). Future studies utilizing the 5C-CBT may further validate whether ketamine increases vigilance when administered as a prophylactic.

There was similarly no effect on fear expression or on depressive-like behavior in the forced swim test when ketamine was administered 1 week before a stronger reinstatement (3-shock CFC). Surprisingly, however, an increase in rearing behavior was not observed in this experiment. These data suggest that the aversive value of the traumatic experience may play a critical role in effectiveness of therapy. It has been suggested that the intensity of the unconditioned stimulus has a direct correlation to the severity of PTSD symptomology (Buydens-Branchey et al., 1990; Yehuda et al., 1992; Norrholm et al., 2011). However, it is more difficult to define stressor severity in humans, given the wide range of criterion that may define a stressor (i.e., witnessing a trauma vs. experiencing one) (Long et al., 2008), as well as the subjective distress of the stressor experienced (Feinstein and Dolan, 1991; O'Hare et al., 2006). However, future work should consider the severity of the stressor in relation to the effectiveness of treatments or preventions for PTSD.

Administering ketamine 1 h after reinstatement did not have effects on fear expression or extinction. This finding agrees with previous studies demonstrating that ketamine did not alleviate symptoms of PTSD when given shortly after a trauma (McGhee et al., 2014; Juven-Wetzler et al., 2013). Interestingly, several studies have speculated that ketamine administered immediately after a strong traumatic incident may enhance fear expression after a single dose (Schonenberg et al., 2005; Schonenberg et al., 2008) or multiple doses (Winter and Irle, 2004).

Overall, it is probable that administering ketamine after re-experiencing the trauma is directly acting on reconsolidation mechanisms. Notably, Schiller and colleagues have proposed that reconsolidation is a window of opportunity to rewrite emotional memories (Schiller et al., 2010).

Interestingly, when ketamine was administered 1 h after a stronger reinstatement trial (3-shock CFC), ketamine decreased subsequent fear expression during extinction. In considering ketamine's effects on memory consolidation, ketamine may be having a similar effect as propranolol, a beta-blocker. Previous data have shown that propranolol may be effective as a treatment for PTSD when administered during the reconsolidation window (Laverdure et al 1991; Taylor and Cahill, 2002; Pitman et al., 2002; Vaiva et al., 2003; Henry et al., 2007; Soeter and Kinds, 2015; Villain et al., 2016). Yet, it is intriguing that recent studies and meta-analyses suggest that the drug may not be reliably effective (McGhee et al., 2009; Muravieva and Alberini, 2010; Cohen et al., 2011; Argolo et al., 2015; Steenan et al., 2016. In light of this field of investigation, however, our data suggest that ketamine may also disrupt consolidation of aversive memories in specific conditions, such as in conditions that robustly activate the fear system.

Figure 13A:
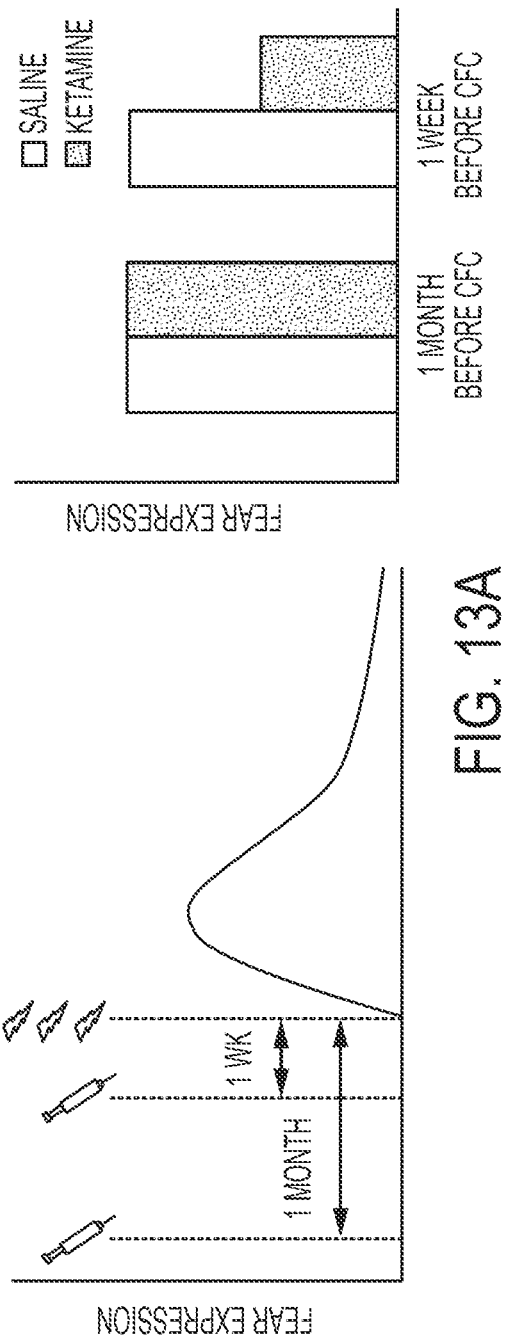
FIGS. 13A-C are graphs showing experimental design and results of fear expression at differing administration times for ketamine compared with saline injected mice.
Figure 13B:
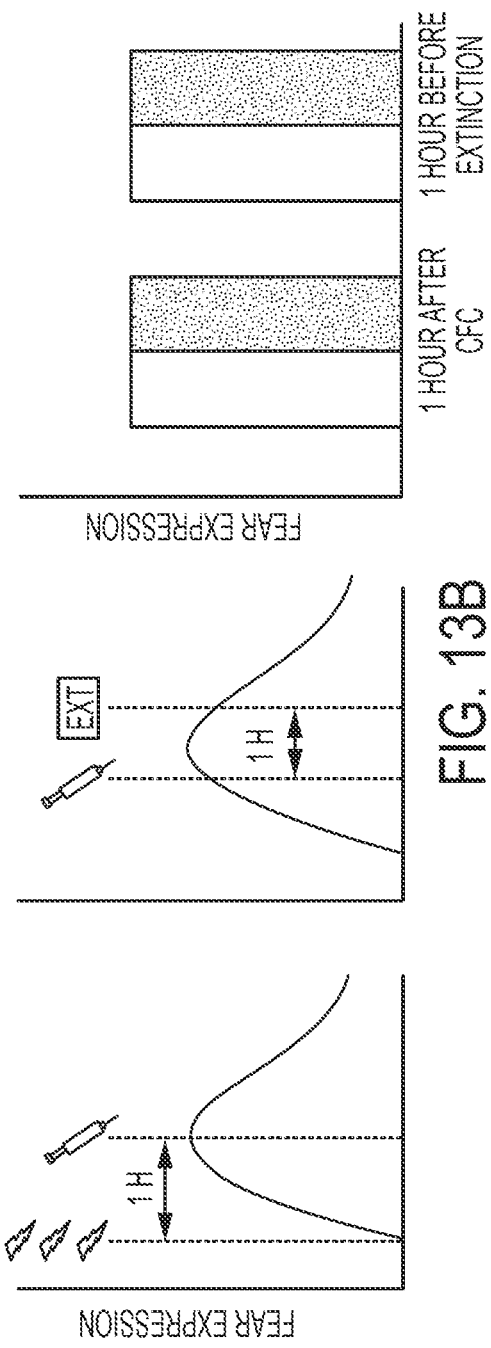
Figure 13C:
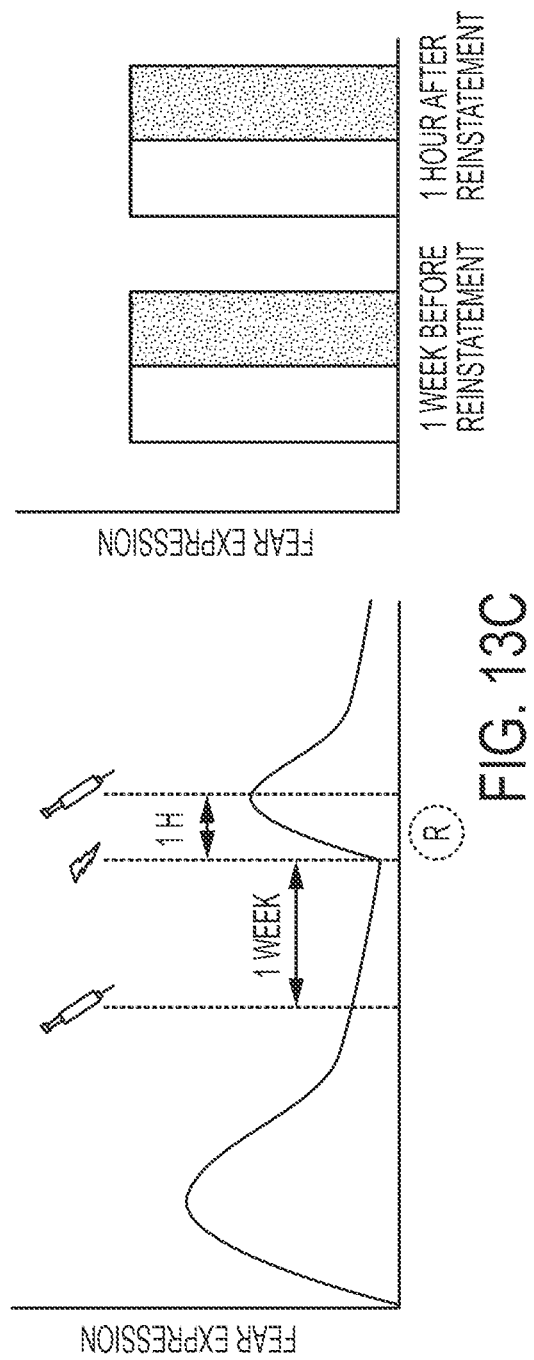
Figure 14A:
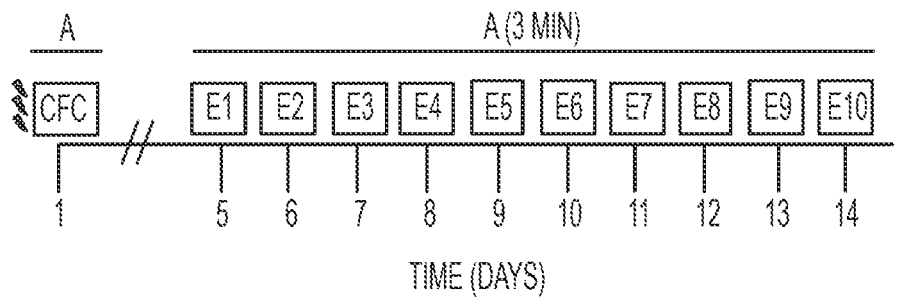
FIGS. 14A-14D are graphs illustrating comparison of contextual fear extinction paradigms.
Figure 14B:
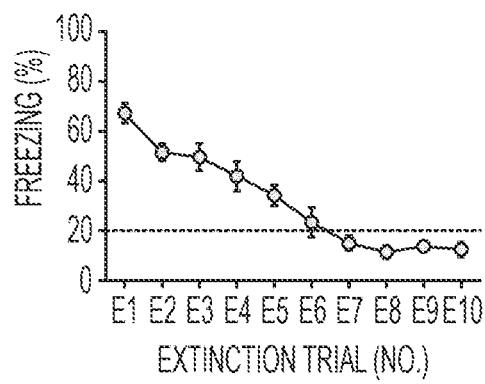
Figure 14C:
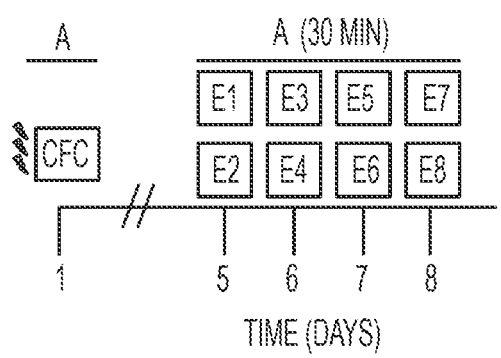
Figure 14D:
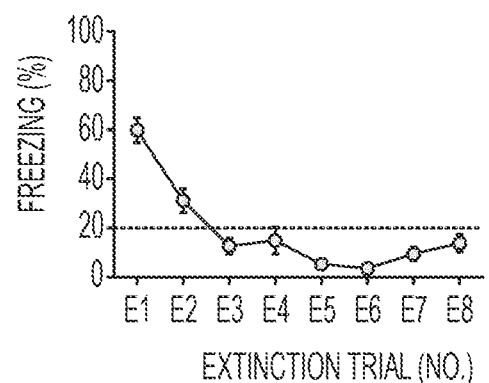

To our knowledge, this study is the first demonstration of a critical time window to administer ketamine for stress-induced psychiatric disease (FIGS. 13A-13C). We propose that ketamine may be most effective when administered in a vaccine-like fashion, but only within a particular time window before the stressor. Ketamine treatment could also enhance vigilance to one's surroundings as long as 2 weeks following administration. Yet, these data indicate that it would not be ideal to administer ketamine shortly after a traumatic experience. We propose these data as a guide for interpreting past and future studies on ketamine's effectiveness for mood disorders.

In certain conditions, ketamine, or suitable analog or metabolite dosing may encompass administration up to two weeks prior to exposure to a stressor; but preferred times include one week prior to exposure; and as a booster at time intervals preceding the expected stressor, but not more than two weeks prior to the expected stressor.

We have also begun to isolate the window within which a prophylactic must be administered. We have found that ketamine is prophylactic when administered 1 week, but not 1 month before a stressor. Crucially, ketamine's resilience-enhancing effect lasts far beyond its ½ life of a few hours (Brachium et al., 2016). A single injection of a sub-anesthetic dose induces robust resilience that lasts for at least four weeks, if not longer. The protection induced must therefore be self-maintaining, akin to the long-lasting protection provided by immunological vaccines. Thus, it is possible that the resilience-enhancing therapeutics proposed here may only require single or infrequent doses to be efficacious.

REFERENCES

1. Tanielian T, Jaycox L H, Schell T L, Marshall U N, Burnam M A, Eibner C, et al. (2008): Invisible Wounds of War: Summary and Recommendations for Addressing Psychological and Cognitive Injuries. Santa Monica, Calif.: RAND Corporation.
2. Russo S J, Murrough J W, Han M H, Charney D S, Nestler E J (2012): Neurobiology of resilience. Nat Neurosci 15:1475-4484.
3. Walsh J J, Friedman A K, Sun H, Heller E A, Ku S M, Juarez B, et al. (2014): Stress and CRF gate neural activation of BDNF in the mesolimbic reward pathway. Nat Neurosci 17:27-29.
4. Chaudhury D, Walsh J J, Friedman AK, Juarez B, Ku S M, Koo J W, et al. (2013): Rapid regulation of depression-related behaviours by control of midbrain dopamine neurons. Nature 493:532-536.
5. Krishnan V, Han M H, Graham D L, Berton O, Renthal W, Russo S J, et al. (20071: Molecular adaptations underlying susceptibility and resistance to social defeat in brain reward regions. Cell 131:391-404.
6. Levine S (1957): Infantile experience and resistance to physiological stress. Science 126:405.
7. Lyons D M, Parker K J (2007): Stress inoculation-induced indications of resilience in monkeys. J Trauma Stress 20:423-433.
8. Meredith L D (2011): Promoting psychological resilience in the U.S. military. Santa Monica, Calif.: RAND Corporation. 9. Schoenfeld T J, Rada P, Pieruzzini P R, Hsueh B, Gould E (2013): Physical exercise prevents stress-induced activation of granule neurons and enhances local inhibitory mechanisms in the dentate gyrus. J Neurosci 33:7770-7777.
10. Schloesser R J, Lehmann M, Martinowich K, Manji H K, Herkenham M (2010): Environmental enrichment requires adult neurogenesis to facilitate the recovery from psychosocial stress. Mol Psychiatry 15: 1152-1163.
11. Lehmann M L, Herkenham M (2011): Environmental enrichment confers stress resiliency to social defeat through an infralimbic cortex-dependent neuroanatomical pathway. J Neurosci 31:6159-6173.
12. Donahue R J, Muschamp J W, Russo S J, Nestler E J, Carleton W A Jr (2014): Effects of striatal deltaFosB overexpression and ketamine on social defeat stress-induced anhedonia in mice. Biol Psychiatry 76:550-558.

13. Lehmann M L, Mustafa T, Eiden A M, Herkenham M, Eiden L E (2013): PACAP-deficient mice show attenuated corticosterone secretion and fail to develop depressive behavior during chronic social defeat stress. Psychoneuroendocrinology 38:702-715.

14. Lehmann M L, Brachman R A, Martinowich K, Schloesser R J, Herkenham M (2013): Glucocorticoids orchestrate divergent effects on mood through adult neurogenesis. J Neurosci 33:2961-2972.

15. Brachman R A, Lehmann M L, Marie D, Herkenham M (2015): Lymphocytes from chronically stressed mice confer antidepressant-like effects to nave mice, J Neurosci 35:1530-1538.

16. Hodes G E, Pfau M L. Leboeuf M, Golden S A, Christoffel D J, Bregman D, et al. (2014): individual differences in the peripheral immune system promote resilience versus susceptibility to social stress. Proc Natl Acad Sci USA 111:16136-16141.

17. Keller M B, Boland R J (1998): Implications of failing to achieve successful long-term maintenance treatment of recurrent unipolar major depression. Biol Psychiatry 44:348-360.

18. Montgomery S A, Dufour H, Brion S, Gailledreau J, Laqueille X, Ferrey C, et al. (1988): The prophylactic efficacy of fluoxetine in unipolar depression. Br J Psychiatry Suppl 3:69-76.

19. Montgomery S A, Dunbar G (1993): Paroxetine is better than placebo in relapse prevention and the prophylaxis of recurrent depression. Int Clin Psychopharmacol 8:189-195.

20. Montgomery S A, Rasmussen J G, Tanghoj P (1993): A 24-week study of 20 mg citalopram, 40 mg citalopram, and placebo in the prevention of relapse of major depression. Int Clin Psychopharmacol 8:181-188.

21. Doogan D P, Caillard V (1992): Sertraline in the prevention of depression. Br J Psychiatry 160:217-222.

22. Frank E, Prien R F, Jarrett R B, Keller M B, Kupfer D J, Lavori P W, et al. (1991): Conceptualization and rationale for consensus definitions of terms in major depressive disorder. Remission, recovery, relapse, and recurrence. Arch Gen Psychiatry 48:851-855.

23. Zarate C A Jr. Singh J B, Carlson P. J. Brutsche N E, Amelia R, Luckenbaugh D A, et al. (2006): A randomized trial of an N-methyl-Daspartate antagonist in treatment resistant major depression. Arch Gen Psychiatry 63:856-864.

24. Murrough J W, Perez A M, Pillemer S, Stern J, Parides M K, aan het Rot M, et al. (2013): Rapid and longer-term antidepressant effects of repeated ketamine infusions in treatment-resistant major depression. Biol Psychiatry 74:250-256.

25. Idvall J, Ahlgren J, Aronsen K R, Stenberg P (1979): Ketamine infusions: Pharmacokinetics and clinical effects. Br J Anaesth 51:1167-1173.

26. Denny C A, Kheirbek M A, Alba E L, Tanaka K F, Brachman R A, Laughman K B, et al. (2014): Hippocampal memory traces are differentially modulated by experience, time, and adult neurogenesis. Neuron 83: 189-201.

27. David D J, Samuels B A, Rainer Q, Wang J W, Marsteller D, Mendez I, et al. (2009): Neurogenesis-dependent and-independent effects of fluoxetine in an animal model of anxiety/depression. Neuron 62:479-493.

28. Hammack S E, Cooper M A, Lezak KR (2012): Overlapping neurobiology of learned helplessness and conditioned defeat: Implications for PTSD and mood disorders. Neuropharmacology 62:565-575.

29. Maier S F, Seligman MEP (1976): Learned helplessness: Theory and evidence. J Exp Psychol 105:3-46.

30. Muller J M, Morelli E, Ansorge M, Gingrich JA (2011): Serotonin transporter deficient mice are vulnerable to escape deficits following inescapable shocks. Genes Brain Behav 10:166-175.

31. Porsolt R D, Le Pichon M, Jalfre M (1977): Depression: A new animal model sensitive to antidepressant treatments. Nature 266:730-732.

32. Dulawa S C, Holick K A, Gundersen B, Hen R (2004): Effects of chronic fluoxetine in animal models of anxiety and depression. Neuropsychopharmacology 29:1321-1330.

33. Autry A E, Adachi M, Nosyreva E. Na E S, Los M F, Chong P F, et al. (2011): NMDA receptor blockade at rest triggers rapid behavioural antidepressant responses. Nature 475:91-95.

34. da Silva F C, do Carmo de Oliveira Cito M, da Silva M A, Mourn B A, de Aquino Neto M R, Feitosa M L, et al. (2010): Behavioral alterations and pro-oxidant effect of a single ketamine administration to mice. Brain Res Bull 83:9-15.

35. Caddy C, Giaroli G, White T P, Shergill S S, Tracy D K (2014): Ketamine as the prototype glutamatergic antidepressant: Pharmacodynamic actions, and a systematic review and meta-analysis of efficacy. Ther Adv Psychopharmacol 4:75-99.

36. Denny C A, Burghardt N S, Schachter D M, Hen R, Drew M R (2012): 4- to 6-week-old adult-born hippocampal neurons influence novelty-evoked exploration and contextual fear conditioning. Hippocampus 22:1188-1201.

37. Drew M R, Denny C A, Hen R (2010): Arrest of adult hippocampal neurogenesis in mice impairs single-but not multiple-trial contextual fear conditioning. Behav Neurosci, 124,446-454.

38. Yu T, Guo M, Garza J, Rendon S, Sun XL, Zhang W, Lu X Y (2011): Cognitive and neural correlates of depression-like behaviour in socially defeated mice: An animal model of depression with cognitive dysfunction. Int J Neuropsychopharmacol 14:303-317.

39. Williams M L, Mager D E, Parenteau H, Gudi G. Tracy T S, Mulheran M, Wainer I W (2004): Effects of protein calorie malnutrition on the pharmacokinetics of ketamine in rats. Drug Metab Dispos 32: 786-793.

40. Vialou V, Bagot R C, Cahill M E, Ferguson D, Robison A J, Dietz D M, et al. (2014): Prefrontal cortical circuit for depression- and anxiety-related behaviors mediated by cholecystokinin: Role of DeltaFosB J Neurosci 34:3878-3887.

41. Vialou V, Robison A J, Laplant Q C, Covington H E 3rd, Dietz D M, Ohnishi Y N, et al. (2010): DeltaFosB in brain reward circuits mediates resilience to stress and antidepressant responses. Nat Neurosci 13: 745-752.

42. Vialou V, Maze I, Renthal W, LaPlant Q C, Watts E L, Mouzon E, et al. (2010): Serum response factor promotes resilience to chronic social stress through the induction of DeltaFosB. J Neurosci 30:14585-14592.

43. Cao J L, Covington H E 3rd, Friedman A K, Wilkinson M B, Walsh J J, Cooper D C, et al. (2010): Mesolimbic dopamine neurons in the brain reward circuit mediate susceptibility to social defeat and antidepressant action. J Neurosci 30:16453-16458.

44. Covington HE 3rd, Lobo M K, Maze I, Vialou V, Hyman Zaman S, et. al. (2010): Antidepressant effect of optogenetic stimulation of the medial prefrontal cortex. J Neurosci 30:16082-16090.

45. Li N, Lee B, Liu R J, Banasr M, Dwyer J M, Iwata M, et al. (2010): mTOR-dependent synapse formation underlies the rapid antidepressant effects of NMDA antagonists. Science 329: 959-964.

"A" References:

A1. David D J, Samuels B A, Rainer Q, Wang J W, Marsteller D, Mendez I, Drew M, Craig D A, Guiard B P, Guilloux J P, Artymyshyn R P, Gardier A M, Gerald C, Antonijevic I A, Leonardo E D, Hen R (2009): Neurogenesis-dependent and-independent effects of fluoxetine in an animal model of anxiety/depression. Neuron 62(4):479-493.

A2. Mendez-David I, David D J, Darcet F, Wu M V, Kerdine-Romer S, Gardier A M et al. (2014): Rapid anxiolytic effects of a 5-HT(4) receptor agonist are mediated by a neurogenesis-independent mechanism, Neuropsychopharmacology 39(6):1366-1378.

A3. Rainer Q, Xia L, Guilloux J P, Gabriel C, Mocaer E, Hen R, et al. (2011): Beneficial behavioural and neurogenic effects of agomelatine in a model of depression/anxiety. Int J Neuropsychopharmacol 15(3)321-335.

A4. Chourbaji S, Zacher C, Sanchis-Segura C, Dormann C, Vollmayr B, Gass P. (2005): Learned helplessness: validly and reliability of depressive-like states in mice. Brain Research Protocols 16: 70-78.

A5. Muller I M, Morelli E, Ansorge M, Gingrich J A. (2011): Serotonin transporter deficient mice are vulnerable to escape deficits following inescapable shocks. Gene Brain Behav 10(2):166-175.

A6. Holmes P V (2003): Rodent models of depression: reexamining validity without anthropomorphic inference, Crit Rev Neurobiol 15(2): 143-174.

A7. Petit-Demouliere B, Chenu Bourin M (2005): Forced swimming test in mice: a review of antidepressant activity. Psychopharmacology (Berl) 177(3): 245-255.

A8, Lindholm J S, Autio H, Vesa L, Antila H, Lindemann L, Hoener M C, et al, (2012): The antidepressant-like effects of glutamatergic drugs ketamine and AMPA receptor potentiator LY 451646 are preserved in bdnf(+)/(−) heterozygous null mice. Neuropharmacology 62(1):391-397.

A9. Ghasemi M, Raza M, Dehpour A R (2010): NMDA receptor antagonists augment antidepressant-like effects of lithium in the mouse forced swimming test. J Psychopharmacol 24(4): 585-594.

A10. Liu R J, Lee F S, Li X Y, Bambico F, Duman R S, Aghajanian G K (2012): Brain-derived neurotrophic factor Va166Met allele impairs basal and ketamine-stimulated synaptogenesis in prefrontal cortex. Biological Psychiatry 71(11): 996-1005.

A11. Richardson-Jones J W, Craige C P, Guiard B P, Stephen A, Metzger K L, Kong H F, et (2040): 5-HT1A Autoreceptor Levels Determine Vulnerability to Stress and Response to Antidepressants. Neuron 65(1): 40-52.

A12. Schloesser R J, Lehmann M, Martinowich K, Manji H K, Herkenham M (2010): Environmental enrichment requires adult neurogenesis to facilitate the recovery from psychosocial stress. Mol Psychiatry: 15(12); 1152-1163.

A13. David D J, Klemenhagen K C, Holick K A, Saxe M D, Mendez I, Santarelli L, et al. (2007):

Efficacy of the MCHRI antagonist N-(3-(1-1(4-(3,4-difluorophenoxy)phenyl)methyl)(4-piperidyl))-4-methylphenyl)-2-methylpropanamide (SNAP 94847) in mouse models of anxiety and depression following acute and chronic administration is independent of hippocampal neurogenesis. J Pharmacology Exp Ther 321(1): 237-248.

A14. Saxe M D, Battaglia F. Wang J-W, Malleret G, David D J, Monckton J E, et al. (2006): Ablation of hippocampal neurogenesis impairs contextual fear conditioning and synaptic plasticity in the dentate gyros. Proc Natl Acad Sci USA 103(46): 17501-17506.

A15. Denny C A, Burghardt N S, Schachter D M, Hen R, Drew M R (2012): 4- to 6-week-old adult horn hippocampal neurons influence novelty-evoked exploration and contextual fear conditioning. Hippocampus 22(5):1188-1201.

A16. Scobie K N, Hall B J, Wilke S A, Klemenhagen K C, Fujii-Koriyama Y, Ghosh A, et al. (2009) Kruppel-like factor 9 is necessary for late-phase neuronal maturation in the developing dentate gyrus and during adult hippocampal neurogenesis. J Neurosci 29(31): 9875-9887.

Amat I, Dolzarti S D, Tilden S, Christianson J P, Kubala K H, Bartholomay K, et al. (2016): Previous ketamine produces an enduring blockage of neurochemical and behavioral effects of uncontrollable stress. J Neurosci 36:153-161.

Annetta M G, Iemma D. Garisto C, Tafani C. Proietti R (2006): Ketamine: New indications far an old drug. Curr Drug Targets 6:789-794.

Argolo F C, Cavalcanti-Ribeiro P, Netto L R, Quarantini L C (2015): Prevention of posttraumatic stress disorder with propranolol: A meta-analytic review. J Psychosom Res 79:89-93.

Berman R M, Cappiello A, Anand A, Oren D A, Hettinger G R, Chantey D S, Krystal J H (2000): Antidepressant effects of ketamine in depressed patients. Biol. Psychiatry 47:351-354.

Bernardini F, Attademo L, Cleary S D, Luter C. Shim R S, Quartesan R, Comptom M T (2016): Risk prediction models in psychiatry: Toward a new frontier for the prevention of mental illnesses. J Clin Psychiatry in press.

Brachman, R A, McGowan J C, Perusini J N, Lim S C, Plain T H, Faye C, et al. (2016): Ketamine as a prophylactic against stress-induced depressive-like behavior. Biol. Psychiatry 79:776-786.

Brady K T, Killeen T K, Brewerton T, Lucerini S (2000): Comorbidity of psychiatric disorders and posttraumatic stress disorder. J Clin Psychiatry 61:22-32.

Buydens-Branchey L, Noumair D, Branchey M (1990): Duration and intensity of combat exposure and posttraumatic stress disorder in Vietnam veterans. J Nerv Ment Dis 178:582-587.

Chambers R A, Bremner S D, Moghaddam B, Southwick S M, Charney D S, Krystal J H (1999): Glutamate and post-traumatic stress disorder: Toward a psychobiology of dissociation. Semin Clin Neuropsychiatry 4:274-781.

Charney D S, Deutch A Y, Krystal J H, Southwick S M, Davis 1(1993): Psychobiologic mechanisms of posttraumatic stress disorder. Arch Gen Psychiatry 50:295-305.

Cohen N, Kaplan Z, Koresh O, Matar M A, Geva A B, Zohar J (2011): Early post-stressor intervention with propranolol is ineffective in preventing posttraumatic stress responses in animal model for PTSD. Eur Neuropsychopharmacol 21:230-240.

Crusio W E (2001): Genetic dissection of mouse exploratory behavior. Beh Brain Res 125:127-132.

Denny C A, Burghardt N S, Schachter D M, Hen R, Drew M R (2012): 4- to 6-week-old adult-born hippocampal neurons influence novelty-evoked exploration and contextual fear conditioning. Hippocampus 22:1188-1201.

Denny C A, Kheirbek M A, Alba E L, Tanaka K F, Brachman R A, Laughman K B, et al. (2014): Hippocampal memory traces are differentially modulated by experience, time, and adult neurogenesis. Neuron 83: 189-201.

Drew M R, Denny C A, Hen R (2010): Arrest of adult hippocampal neurogenesis in mice impairs single-but not multiple-trial contextual fear conditioning. Behav Neurosci 124:446-454.

Feder A, Parides M K, Murrough J W, Perez A M, Morgan J E, Sazena S, et al. (2014): Efficacy of intravenous ketamine for treatment of chronic posttraumatic stress disorder. *JAMA Psychiatry* 71:681-688.

Feinstein A, Dolan R (1991): Predictors of post-traumatic stress disorder following physical trauma: an examination of the stressor criterion. *Psychol Med* 21:85-91.

Golub Y, Mauch C P, Dahlhoff M, Wotjac C T (2009): Consequences of extinction training on associative and non-associative fear in a mouse model of Posttraumatic Stress Disorder (PTSD). *Behav Brain Res* 205:544-549.

Henry M., Fishman J R, Youngner S J (2007): Propranolol and the prevention of post-traumatic stress disorder: is it wrong to erase the "sting" of bad memories? *Am J Bioeth* 7:12-20. Hofmann S G, Sawyer A T, Witt A A, Oh D (2010): The effect of mindfulness-based therapy on anxiety and depression: A meta-analytic review. *J Consult Clin Psychol* 78: 169-83.

Horn S R, Charlie D S, Feder A (2016): Understanding resilience: New approaches for preventing and treating PTSD. *Exp Neural* in press.

Juven-Wetzler. A, Cohen H, Kaplan Z, Kohen A, Porat O, Zohar J (2014): Immediate ketamine treatment does not prevent posttraumatic stress responses in an animal model for PTSD. *Eur Neuropsychopharmacol* 24:469-479.

Klein D F (2000): Flawed meta-analyses comparing psychotherapy with pharmacotherapy. *Am J Psychiatry* 157:1204-1211.

Laverdure B, Boulenger J P (1991): Beta-blocking drugs and anxiety: a proven therapeutic value. *Encephale* 17:481-492.

Lever C. Burton S, O'Keefe J (2006): Rearing on Hind Legs, Environmental Novelty, and the Hippocampal Function. *Reviews in the Neurosciences* 17:111-133.

Long M E, Elhai J D, Schweinle A, Gray M J, Grubaugh A L, Fruch B C (2008): Differences in posttraumatic stress disorder diagnosistic rates and symptom severity between Criterion A1 and non-Criterion A1 stressors. *J Anxiety Disord* 22:1255-1263.

Lubin H, Loris M, Burt J, Johnson D R (1998): Efficacy of psychoeducational group therapy in reducing symptoms of posttraumatic stress disorder among, multiply traumatized women. *Am J Psychiatry* 155:1172-1177.

McGhee L L, Maani C V, Garza T H, Gaylord K M, Black I H (2008): The correlation between ketamine and posttraumatic stress disorder in burned service members. *J Trauma* 64:S195-198.

McGhee L L, Maani C V, Garza T H, DeSocio P A, Gaylord K M, Black I H (2009): The effect of propranolol on posttraumatic stress disorder in burned service members. *J Burn Care Res* 30:92-97.

McGhee L L, Maani C V, Garza T H, Slater T M, Petz L N, Fowler M (2014): The intraoperative administration of ketamine to burned U.S. service members does not increase the incidence of post-traumatic stress disorder. *Mil Med* 179:41-46.

Moghaddam B, Adams B, Verma A, Daly D (1997): Activation of glutamatergic neurotransmission by ketamine: A novel step in the pathway from NMDA receptor blockade to dopaminergic and cognitive disruptions associated with the prefrontal cortex. *J Neurosci* 17:2921-2927.

Muravieva E V, Alberini C M (2010): Limited efficacy of propranolol on the reconsolidation of fear memories. *Learn Mem* 17:306-313.

National Center for PTSD (2015): How common is PTSD? *U.S. Department of Veterans Affairs, National Center for PTSD*.

Norrholm S D, Jovanovic T, Olin J W, Sands L A Karapanou I, Bradley B, Ressler K J (2011): Fear exinction in traumatized civilians with posttraumatic stress disorder. *Biol Psychiatry* 15:556-563.

O'Hare T, Sherrer M V, Shen C (2006): Subjective distress from stressful events and high-risk behaviors as predictors of PTSD symptom severity in clients with severe mental illness. *J Trauma Stress* 19:375-386.

Pick C G, Cheng J, Paul D, Pasternak G W (1991 Genetic influences in opioid analgesic sensitivity in mice. *Brain Res* 566:295-298.

Pietersen C Y, Bosker F J, Postema F, Fokkema S D, Korf J, den Boer J A (2006): Ketamine administration disturbs behavioural and distributed neural correlates of fear conditioning in the rat. *Prog Neuropsychopharmacol Biol Psychiatry* 30:1209-1218.

Pitman R K, Sanders K M, Zusman R M, Healy A R, Cheema F, Lasko N B, et al. (2002): Pilot study of secondary prevention of posttraumatic stress disorder with propranolol. *Biol Psychiatry* 51:189-197.

Ponder C A, Kliethermes C L, Drew M R, Muller J, Das K, Rishbrough V B, et al. (2007): Selection for contextual fear conditioning affects anxiety-like behaviors and gene expression. *Genes Brain Behav* 6:736-749.

Pradhan B, D'Amico J K, Makani R, Parikh T (2016): Nonconventional interventions for chronic post-traumatic stress disorder: Ketamine, repetitive trans-cranial magnetic stimulation (Runs), and alternative approaches. *J Trauma Dissociation* 17:35-54.

Price R B (2016): From mice to men: Can ketamine enhance resilience to stress? *Biol Psychiatry* 79:e57-59.

Richardson-Jones J W, Craige C P, Guiard B P, Stephen A, Metzger K L, Kung H F, et al. (2010): 5-HT1A Autoreceptor Levels Determine Vulnerability to Stress and Response to Antidepressants. *Neuron* 65:40-52.

Rosenbaum S, Vancampfort D, Steel Z, Newby J, Ward P B, Stubbs B (2015): Physical activity in the treatment of post-traumatic stress disorder: A systematic review and meta-analysis. *Psychiatry Res* 2:130-136.

Sanabenesi F, Fischer A, Wang X, Schrick C, Neve R, Radulovic J, Tsai L H (2007): A hippocampal Cdk 5 path way regulates extinction of contextual fear. *Nat Neurosci* 10:1012-1019.

Sassano-Higgins S, Baron D, Juarez G, Esmaili N, Gold M (2016): A review of ketamine abuse and diversion. *Depress Anxiety* in press.

Schiller D, Monfils M H, Raio C M, Johnson D C, LeDoux J E, Phelps E A (2010): Preventing the return of fear in humans using reconsolidation update mechanisms. *Nature* 463:49-53.

Schonenberg M, Reichwald U, Domes G, Badke A, Hautzinger M (2005): Effects of peritraumatic ketamine medication on early and sustained posttraumatic stress symptoms in moderately injured accident victims. *Psychopharmacol* 182:420-425.

Schonenberg M, Reichwald U, Domes G, Badke A, Hautzinger M (2008): Ketamine aggravates symptoms of acute stress disorder in a naturalistic sample of accident victims. *Psychopharm* 22:493-497.

Shapiro F, Solomon R M (2010): Eye movement desensitization and reprocessing. *Corsini Encyclopedia of Psychology* 1-3.

Skeffington P M, Rees C S, Mazzucchelli T G, Kane R T (2016): The primary prevention of PTSD in firefighters: Preliminary results of an RCT with 12-month follow-up. *PLoS One* in press.

Soeter M, Kinch. M (2015): An abrupt transformation of phobic behavior after a post-retrieval amnesic agent. *Biol Psychiatry* 78:880-886.

Steenan S A, van Wijk A J, van der Heijden GJMG, van Westrhenen R, de Lange J, de Jongh A (2016): Propranolol for the treatment of anxiety disorders: Systematic review and meta-analysis. *J Psychopharm* 30:128-119.

Stein D J, Ipser J C, Seedat S (2006): Pharmacotherapy for post traumatic stress disorder (PTSD). *Cochrane Database syst Rev*

Takahashi R N, Morato G S, Rae G A (1986): Effects of ketamine on nociception and gastrointestinal motility in mice are unaffected by naloxone. *Gen Pharmacol* 18:201-3.

Taylor F, Cahill L (2002): Propranolol for reemergent posttraumatic stress disorder following an event of retraumatization: A case study. *J Trauma Stress* 433-437.

Tronson N C, Schrick C, Fischer A, Sananbenesi F, Pages G, Pouysségur J, Radulovic J (2008): Regulatory mechanisms of fear extinction and depression-like behavior. *Neuropsychopharmacology* 33:1570-1583.

Trouch S, Sasaki J M, Tu T, Reijmers L G (2013): Fear extinction causes target-specific remodeling of perisomatic inhibitory synapses. *Neuron* 80:1054-1065.

Vaiva G, Ducrocq F, Jezequel K, Averland B, Lestavel P. Brunet A, Marmar C R (2003): Immediate treatment with propranolol decreases posttraumatic stress disorder two months after trauma. *Blot Psychiatry* 54:947-949.

Van Abeelen J H F (1975): Genetic analysis of behavioural responses to novelty in mice. *Nature* 254:239-241.

Van Abeelen J H F (1977): Rearing responses and locomotor activity in mice: Single-locus control. *Beh Biol* 19:401-404.

Villain H, Benkahoul A, Drougard A, Lafragette M, Muzotte E, Pech S, et al, (2016): Effects of propranolol, a β-noradrenergic antagonist, on memory consolidation and reconsolidation in mice. *Front Behav Neurosci* In press.

Wald I, Fruchter E, Ginat K, Stolin E, Dagan D, Bliese P D, et al, (2016): Selective prevention of combat-related post-traumatic stress disorder using attention bias modification training: A randomized controlled trial. *Psychol Med* In press.

Wieber J, Gugler R, Hengstmann J G, Dengler H J (1975): Pharmacokinetics of ketamine in man. *Anaesthesist* 24:260-263.

Winter H, Irle E (2004): Hippocampal volume in adult burn patients with and without posttraumatic stress disorder. *Am J Psychiatry* 161:2194-2200.

Yehuda R, Southwick S M, Giller E L (1992): Exposure to atrocities and severity of chronic posttraumatic stress disorder in Vietnam combat veterans. *Am J Psychiatry* 149:333-336.

Young J W, Light G A, Marston H M, Sharp R, Geyer M A (2009): The 5-choice continuous performance test: Evidence for a translational test of vigilance for mice. *PLoS One* 4:e4227.

Zarate C A, Singh J B, Carlson P J. Brutsche N E, Ameli R, Luckenbaugh D A, et al. (2006): A randomized trial of an N-methyl-D-aspartate antagonist in treatment-resistant major depression. *Arch Gen Psychiatry* 63:856-864.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, and publications are cited throughout this application, the disclosures of which, particularly, including all disclosed chemical structures, are incorporated herein by reference. Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A method for preventing or delaying a stress-induced affective disorder or stress-induced psychopathology in a subject, the method consisting of administering, once or twice, an effective amount of a pharmaceutic composition consisting of ketamine to the subject, wherein the method consists of administering the pharmaceutic composition to the subject 1 week prior to the stressor.

2. The method of claim 1, wherein the pharmaceutic composition is administered to the subject once prior to a stressor.

3. The method of claim 1, wherein the pharmaceutic composition is administered orally, intravenously, intranasally, or via injection to the subject.

4. The method of claim 1, wherein the stress-induced affective disorder comprises major depressive disorder and/or posttraumatic stress disorder (PTSD).

5. The method of claim 1, wherein the stress-induced affective disorder is selected from the group consisting of: depressive-like behavior and associated affective disorders, anhedonic behavior and associated affective disorders, anxiety and associated affective disorders, cognitive impairments and deficits and associated disorders, fear, and combinations thereof.

6. The method of claim 1, wherein the stress-induced affective disorder comprises stress-induced psychopathology.

7. The method of claim 6, wherein the stress-induced psychopathology comprises depressive and/or anxious behavior.

8. The method of claim 1, wherein the subject is a mammal.

9. The method of claim 1, wherein the subject is a human.

* * * * *